(12) United States Patent
Yoshida et al.

(10) Patent No.: US 8,911,805 B2
(45) Date of Patent: Dec. 16, 2014

(54) CALCIUM PREPARATION AND METHOD OF PRODUCTION THEREOF

(71) Applicants: Tsutomu Yoshida, Tokyo (JP); Toshitaka Yasuda, Tokyo (JP); Manabu Shimojoh, Tokyo (JP); Kazuyoshi Masaki, Tokyo (JP)

(72) Inventors: Tsutomu Yoshida, Tokyo (JP); Toshitaka Yasuda, Tokyo (JP); Manabu Shimojoh, Tokyo (JP); Kazuyoshi Masaki, Tokyo (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 13/629,286

(22) Filed: Sep. 27, 2012

(65) Prior Publication Data

US 2013/0022733 A1  Jan. 24, 2013

Related U.S. Application Data

(63) Continuation of application No. PCT/JP2011/058347, filed on Mar. 31, 2011.

(30) Foreign Application Priority Data

Mar. 31, 2010  (JP) ................................ 2010-083190

(51) Int. Cl.

| | | |
|---|---|---|
| *A23L 1/304* | (2006.01) | |
| *A61K 31/19* | (2006.01) | |
| *A61K 33/06* | (2006.01) | |
| *A61K 9/00* | (2006.01) | |
| *A61K 33/42* | (2006.01) | |
| *A23L 2/52* | (2006.01) | |

(52) U.S. Cl.
CPC . *A23L 2/52* (2013.01); *A61K 31/19* (2013.01); *A61K 33/06* (2013.01); *A23L 1/304* (2013.01); *A61K 9/0095* (2013.01); *A61K 33/42* (2013.01)
USPC ........................................... 426/74; 426/590

(58) Field of Classification Search
CPC ......... A23L 1/304; A23L 1/3045; A23L 2/52; A23K 31/19; A23K 33/06; A61K 33/42; A61K 9/0095; A23V 2200/306; A23V 2200/312; A23V 2250/1578; A23V 2250/032; A23V 2250/046
USPC ................................................... 426/74, 590
See application file for complete search history.

(56) References Cited

U.S. PATENT DOCUMENTS 4,551,342 A  11/1985  Nakel et al.

(Continued)

FOREIGN PATENT DOCUMENTS

JP  56-97248 A  8/1981

(Continued)

OTHER PUBLICATIONS

Colloid—Wikipedia, p. 1, "IUPAC definition", http://en.wikipedia.org/wiki/Colloid, Oct. 11, 2013.*

(Continued)

*Primary Examiner* — Helen F Heggestad
(74) *Attorney, Agent, or Firm* — Holtz, Holtz, Goodman & Chick PC

(57) ABSTRACT

A stable Ca preparation in solution form even at high concentration is provided. The aqueous preparation of Ca includes water, Ca, compounds of Formula I and Formula II. Most of Ca is in non-ionic form and forms a complex. In the complex, Ca binds to the compound(s) of Formula I and/or Formula II in a state that basic structures of them are kept. At least partially, the complex forms colloidal particles. The aqueous preparation is transparent. pH is equal to or higher than that of slightly acid;

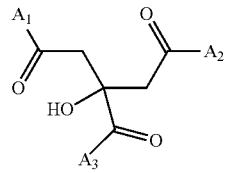

Formula I

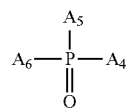

Formula II $[A_1, A_2, A_3, A_4, A_5$ and $A_6$ are independently $O^-$ or OX. X represents a monovalent or polyvalent cation].

22 Claims, 31 Drawing Sheets

1-2

(56) References Cited

U.S. PATENT DOCUMENTS

| | | | |
|---|---|---|---|
| 4,737,375 A | 4/1988 | Nakel et al. | |
| 5,153,005 A | 10/1992 | Grodberg | |
| 5,851,578 A * | 12/1998 | Gandhi | 426/590 |
| 6,248,376 B1 | 6/2001 | Buddemeyer et al. | |
| 2003/0118694 A1 | 6/2003 | Hojo et al. | |

FOREIGN PATENT DOCUMENTS

| | | |
|---|---|---|
| JP | 59-187768 A | 10/1984 |
| JP | 63-157964 A | 6/1988 |
| JP | 4-287660 A | 10/1992 |
| JP | 5-507692 A | 11/1993 |
| JP | 6-329557 A | 11/1994 |
| JP | 7-89852 A | 4/1995 |
| JP | 9-12811 A | 1/1997 |
| JP | 9-175994 A | 7/1997 |
| JP | 9-289877 A | 11/1997 |
| JP | 2002-525091 A | 8/2002 |
| JP | 2003-235466 A | 8/2003 |
| JP | 2004-534709 A | 11/2004 |
| JP | 2005-500231 A | 1/2005 |
| WO | WO 91/19692 A2 | 12/1991 |
| WO | WO 03/032752 A1 | 4/2003 |

OTHER PUBLICATIONS

International Preliminary Report on Patentability (IPRP) dated Nov. 22, 2012 (in English) issued in parent International Application No. PCT/JP2011/058347.

International Search Report and Written Opinion dated Apr. 26, 2011 (in English) in counterpart International Application No. PCT/JP2011/058347.

A. Lopez-Macipe et al; Nanosized Hydroxyapatite Precipitation From Homogenous Calcium/Citrate/Phosphate Solutions Using Microwave and Conventional Heating; 1998; Adv. Mater vol. 10, No. 1, pp. 49-53.

R. Gonzalez-McQuire et al; Synthesis and Characterization of Amino Acid-Functionalized Hydroxyapatite Nanorods; The Royal Society of Chemistry; 2004; pp. 2277-2281.

M. Martins et al; Hydroxyapatite Micro-and Nanoparticles: Nucleation and Growth Mechanisms in the Presence of Citrate Species; Journal of Colloid and Interface Science; 2008; pp. 210-216.

Japanese Office Action dated Sep. 9, 2014 issued in counterpart Japanese Application No. 2012-509615.

Graves, et al., "Transmission of Visible and Ultraviolet Light through Charge-Stabilized Nanoemulsions", J. Phys. Chem. C, 112, Jul. 29, 2008, pp. 12669-12676.

Saitoh, "Properties and Applications of Ultrafine Ceramic Powders", Powder and Industry; vol. 30, No. 3, 1998, pp. 35-40.

* cited by examiner

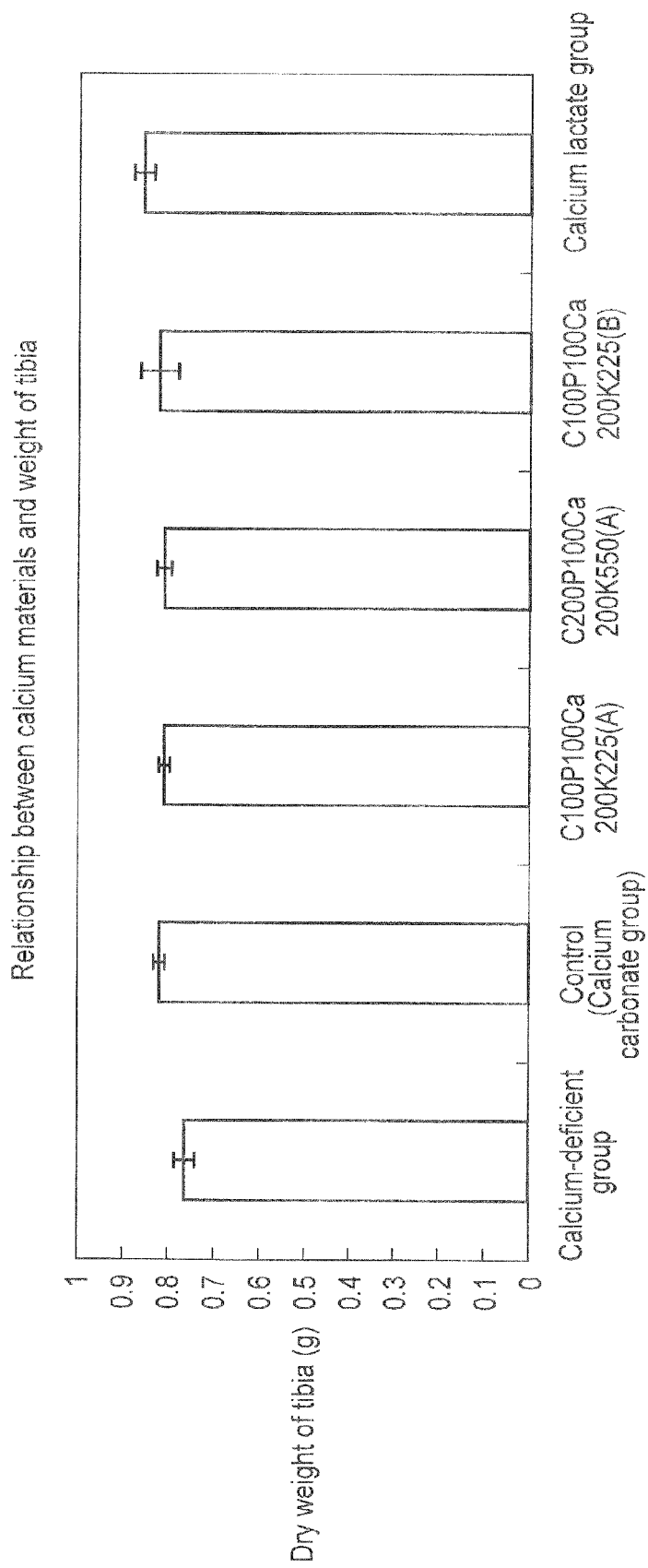
F I G. 6

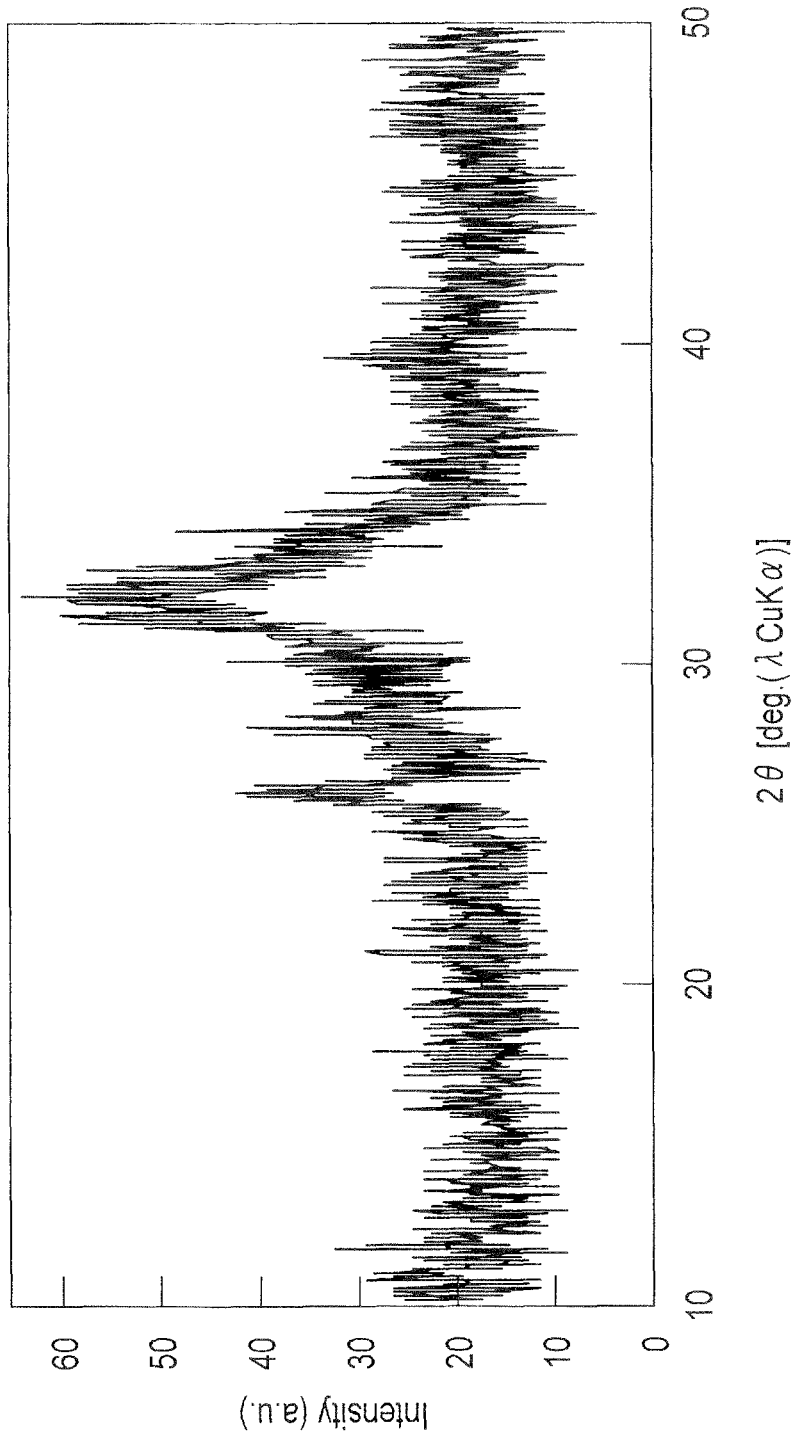

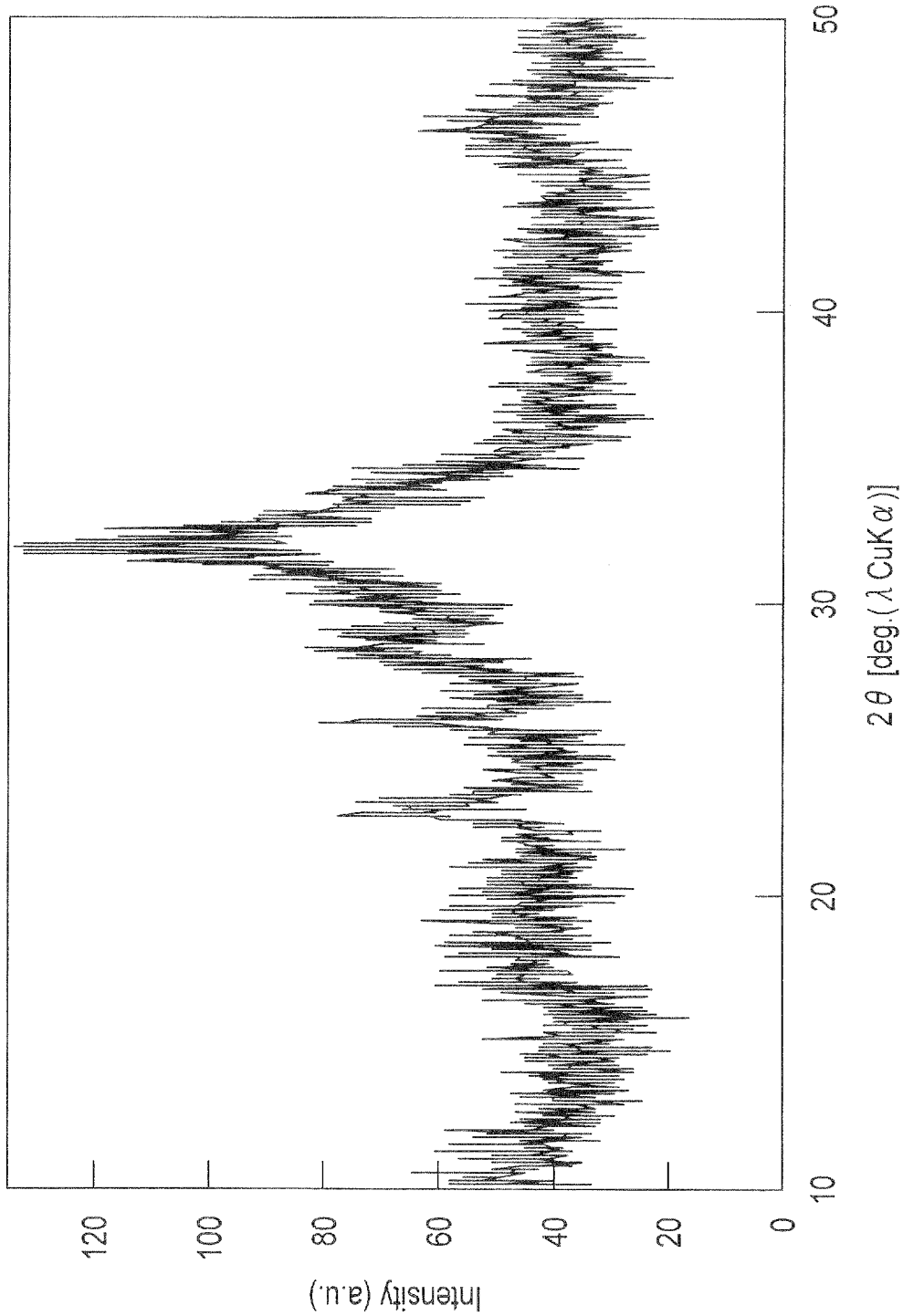
F I G. 8C

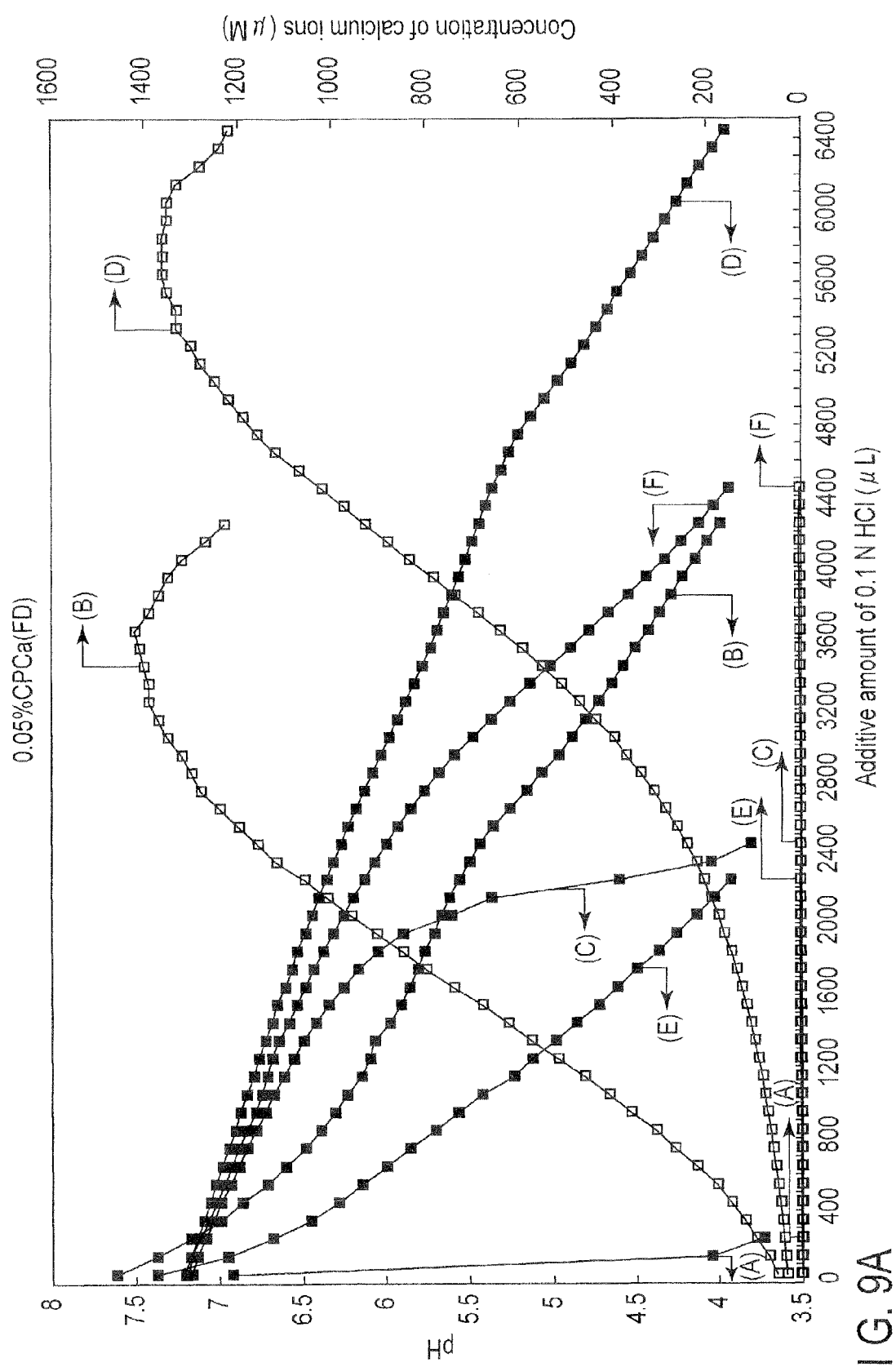
F I G. 9A

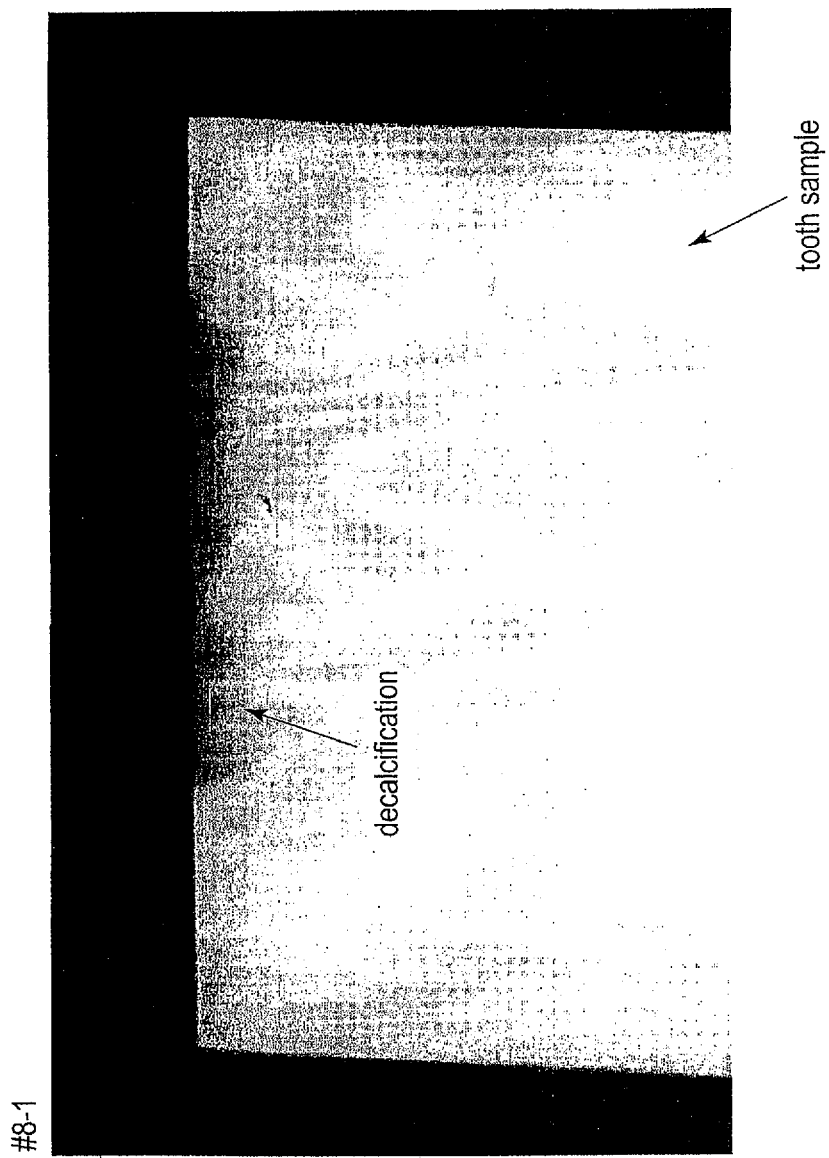
F I G. 13A

CALCIUM PREPARATION AND METHOD OF PRODUCTION THEREOF

CROSS REFERENCE TO RELATED APPLICATIONS

This application is a Continuation Application of PCT Application No. PCT/JP2011/058347, filed Mar. 31, 2011 and based upon and claiming the benefit of priority from prior Japanese Patent Application No. 2010-083190, filed Mar. 31, 2010, the entire contents of all of which are incorporated herein by reference.

BACKGROUND OF THE INVENTION

1. Field of the Invention

The present invention relates to a calcium preparation and a method of production thereof.

2. Description of the Related Art

A shortage of calcium intake of the Japanese is attributed to the fact that since the soils in Japan are mainly constituted of acidic soils, the amount of calcium in the soils is low as compared to that in Western countries and the amount of calcium taken from agricultural crops, water or the like is small. Further, it is attributed to the fact that the intake of dairy products of the Japanese is low as compared to that in Western countries.

In "the Japanese Dietary Reference Intake (2010)" presented by the Ministry of Health, Labour and Welfare as measures against lifestyle-related diseases, calcium is included in nutrients that the Japanese are encouraged to voluntarily increase taking. In the National Health and Nutrition Examination Survey (2008), the Japanese average ingestion of calcium is 511 mg. Thus, the result is below the recommended amount per adult per day, about 600 mg to about 700 mg. Calcium plays an important role to maintain the living body itself and its functions. Further, it is not only involved in the formation of bones and teeth but also is an indispensable element for physiological functions in many organs in the living body including blood, nerves, muscles; tissues, and cells as well as maintenance of homeostasis thereof.

On the other hand, supplements and nutrition fortified food are actively used to improve preventive medicine and improve the quality of life. However, calcium is a substance whose absorption from food is low. Additionally, the bitterness peculiar to calcium prevents a continuous oral ingestion of the calcium solution as a nutrient supplement.

Under such circumstances, there has been much development in the field of calcium, and many applications and reports exist.

Jpn. Pat, Appln. KOKAI Publication No. 56-97248 (Patent Literature 1) discloses a water-soluble calcium malate-calcium citrate complex wherein characteristics in that the rate of dissolution of poorly water-soluble calcium citrate is increased in the presence of calcium malate are used. Jpn. POT National Publication No. 5-507692 (Patent Literature 2) and Jpn. PCT National Publication No. 2002-525091 (Patent Literature 3) disclose a calcium citrate malate whose water solubility is improved. However, the solution disclosed in these literatures is a calcium solution which is poor in long-term stability.

Jpn. Pat, Appln. KOKAI Publication No. 7-89852 (Patent Literature 4) discloses a technique of obtaining water-soluble calcium powder by dissolving calcium oxide fired at high temperatures in an organic acid or an organic acid-containing liquid and drying it. The water-soluble calcium powder disclosed in the literature is acidic when dissolved in water.

Jpn. Pat. Appln. KOKAI Publication No. 2003-235466 (Patent Literature 5) discloses a water-soluble mixed feed composition prepared by mixing phosphoric acid calcium salt with organic acid. The obtained solution is acidic and a composition for feed use is disclosed.

Jpn. Pat. Appln. KOKAI Publication No. 9-289877 (Patent Literature 6) discloses a technique of surface-treating hydroxyapatite particles having a size of 800 nm or less with citric acid or a citrate containing liquid or protein or peptide as a calcium strengthening agent capable of being stably dispersed and suspended for a long time without being precipitated when adding water. Jpn. Pat, Appln. KOKAI Publication No. 6-329557 (Patent Literature 7) discloses a technique of surface-treating hydroxyapatite particles with albumin and/or polyvalent organic acid to stabilize a dispersion liquid. Although the hydroxyapatite dispersion liquid disclosed in these techniques is a stably dispersed liquid, the technique is mainly preformed under acid conditions. Further, the liquid is opaque and thus aggregation is easily caused.

Adv. Mater. 1998. 10. No. 1 49-53 (Non-Patent Literature 1) discloses a technique of obtaining nano-sized hydroxyapatite crystals by irradiating a mixture of citric acid, sodium phosphate, and calcium chloride or a mixed liquid of phosphoric acid/EDTA/calcium with microwaves or heating it at 100° C. J. Coll. in Sci. 318 (2008), 210-216 (Non-Patent Literature 2) discloses that citric acid and pH have an influence on the crystal size of hydroxyapatite. U.S. Pat. No. 6,248,376 (Patent Literature 8) discloses a method of obtaining a calcium-rich composition containing a phosphate ion source, a citrate ion source, and a calcium ion source, metal hydroxide, and water by heating a mixture of calcium hydroxide, phosphoric acid, citric acid, and potassium hydroxide in the water to 100° C. All of these techniques are methods for obtaining hydroxyapatite crystals.

Jpn. PCT National Publication No. 2004-534709 (Patent Literature 9) discloses a stable and water-soluble colloidal dispersion liquid of hydroxyapatite which contains amino acid as a stabilizer. Jpn. PCT National Publication No. 2005-500231 (Patent Literature 10) discloses a stable and water-soluble colloidal dispersion liquid of hydroxyapatite which contains a bifunctional stabilizer. J. Mater. Chem., 2004, 14, 2277-2281 (Non-Patent Literature 3) discloses a water-soluble colloid of hydroxyapatite which contains amino acid as a stabilizer. In any of the literatures, a dipolar ionic stabilizer is needed to produce the water-soluble colloid dispersion liquid of hydroxyapatite.

Jpn. Pat. Appln. KOKAI Publication No. 9-175994 (Patent Literature 11) discloses a technique of obtaining a large dissolution amount of a calcium liquid by dissolving the calcium source in citric acid and/or malic acid and lactic acid.

In order to provide a composition whose readily absorbable properties are improved, Jpn. Pat. Appln. KOKAI Publication No. 9-12811 (Patent Literature 12) discloses a technique of dissolving calcium salt in lactic acid and phosphoric acid.

There are many reports described above; however, a technique of obtaining a transparent calcium preparation which is less bitter and stable at high concentration has not been established. There is still a demand for the development of more excellent techniques.

CITATION LIST

Patent Literature

Patent Literature 1: Jpn. Pat, Appln. KOKAI Publication No. 56-97248
Patent Literature 2: Jpn. PCT National Publication No. 5-507692
Patent Literature 3: Jpn. PCT National Publication No. 2002-525091
Patent Literature 4: Jpn. Pat. Appln. KOKAI Publication No. 7-89852
Patent Literature 5: Jpn. Pat. Appln. KOKAI Publication No. 2003-235466
Patent Literature 6: Jpn. Pat. Appln. KOKAI Publication No. 9-289877
Patent Literature 7: Jpn. Pat. Appln. KOKAI Publication No. 6-329557
Patent Literature 8: U.S. Pat. No. 6,248,376
Patent Literature 9: Jpn. PCT National Publication No. 2004-534709
Patent Literature 10: Jpn. PCT National Publication No, 2005-500231
Patent Literature 11: Jpn. Pat. Appln. KOKAI Publication No. 9-175994
Patent Literature 12: Jpn. Pat, Appln. KOKAI Publication No, 9-12811

Non-Patent Literatures

Non-Patent Literature 1: Adv. Mater. 1998, 10, No. 1 49-53
Non-Patent Literature 2: J. Coll. int. Sci. 318 (2008). 210-216
Non-Patent Literature 3: J. Mater. Chem., 2004, 14, 2277-2281

BRIEF SUMMARY OF THE INVENTION

Technical Problem

An object of the present invention is to provide a stable calcium preparation in solution form even at high concentration, particularly a less-bitter calcium preparation which is stable in solution form even at high concentration in a wide pH range higher than that of slightly acid.

Solution to Problem

The present inventors have been dedicated to studies. As a result, they have completed the present invention for solving the problems.

One embodiment according to the present invention is an aqueous preparation of calcium comprising water, calcium, a compound of Formula I, and a compound of Formula II as constituent elements, wherein most of the calcium is in non-ionic calcium form and forms a complex, wherein in the complex, the calcium binds to the compound of Formula I and/or the compound of Formula II in a state that basic structures of these compounds are kept, and at least a part of the complex forms colloidal particles, and wherein the aqueous preparation of calcium is a transparent aqueous preparation having a pH equal to or higher than that of slightly acid;

[Chemical formula 1]

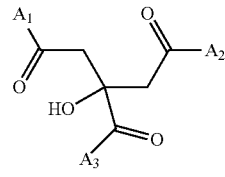

Formula I

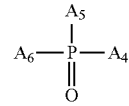

Formula II wherein, $A_1$, $A_2$, $A_3$, $A_4$, $A_5$ and $A_6$ are independently $O^-$ or OX, X represents a monovalent or polyvalent cation, and the Xs are the same or different when multiple OXs exist.

Further embodiment according to the present invention is a solid preparation of calcium obtained by drying the said aqueous preparation of calcium.

Further embodiment according to the present invention is a method of producing an aqueous preparation of calcium, the method characterized in mixing a calcium source ionized in water with a source of a compound of Formula I and a source of a compound of Formula II; and converting the obtained liquid from an opaque liquid to a transparent liquid under the condition where the pH of a final solution is equal or higher than that of slightly acid.

Further embodiment according to the present invention is a method of preventing the formation of precipitates derived from calcium in a calcium solution, the method characterized in; mixing calcium ionized in water with a compound of Formula I and a compound of Formula II; and converting the obtained liquid from an opaque liquid to a transparent liquid under the condition where the pH of a final solution is equal to or higher than that of slightly acid.

Advantageous Effects of Invention

According to the present invention, there is provided a stable calcium preparation in solution form even at high concentration.

BRIEF DESCRIPTION OF THE SEVERAL VIEWS OF THE DRAWING

FIG. 6 is a view showing the results of Example 14 of the present invention;
FIG. 7C is a view showing the results of Example 21 of the present invention;

FIG. 8C is a view showing the results of Example 21 of the present invention;

FIG. 9A is a view showing the evaluation results of the buffer capacity of the calcium preparation and the releasing capacity of calcium ions of the calcium preparation;

FIG. 13A is a photograph showing the evaluation results of the inhibitory effect of the calcium preparation on the decalcification of dentine;

DETAILED DESCRIPTION OF THE INVENTION

Figure 1:
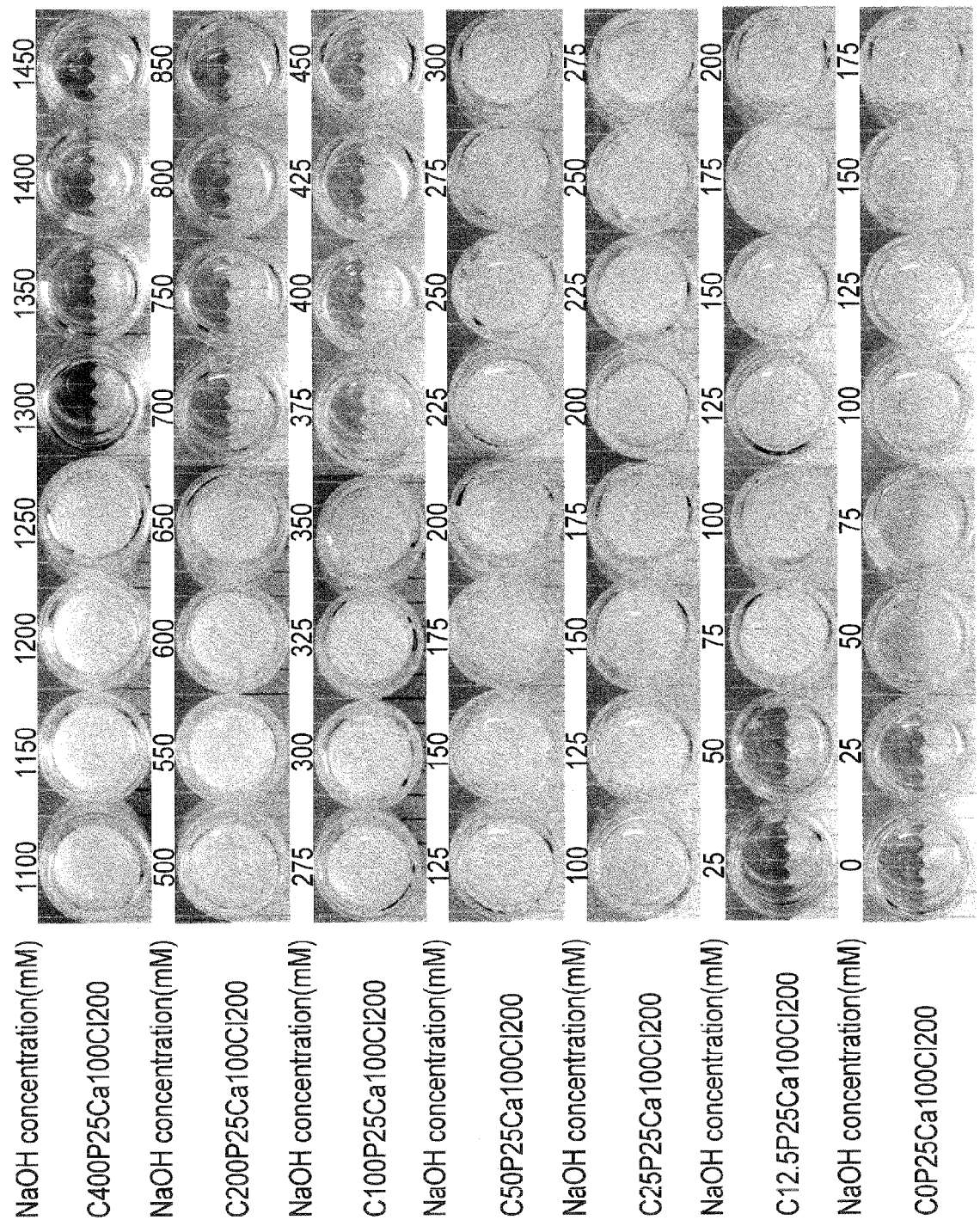
FIG. 1 is a view showing the results of Example 1 of the present invention.
Figure 2:
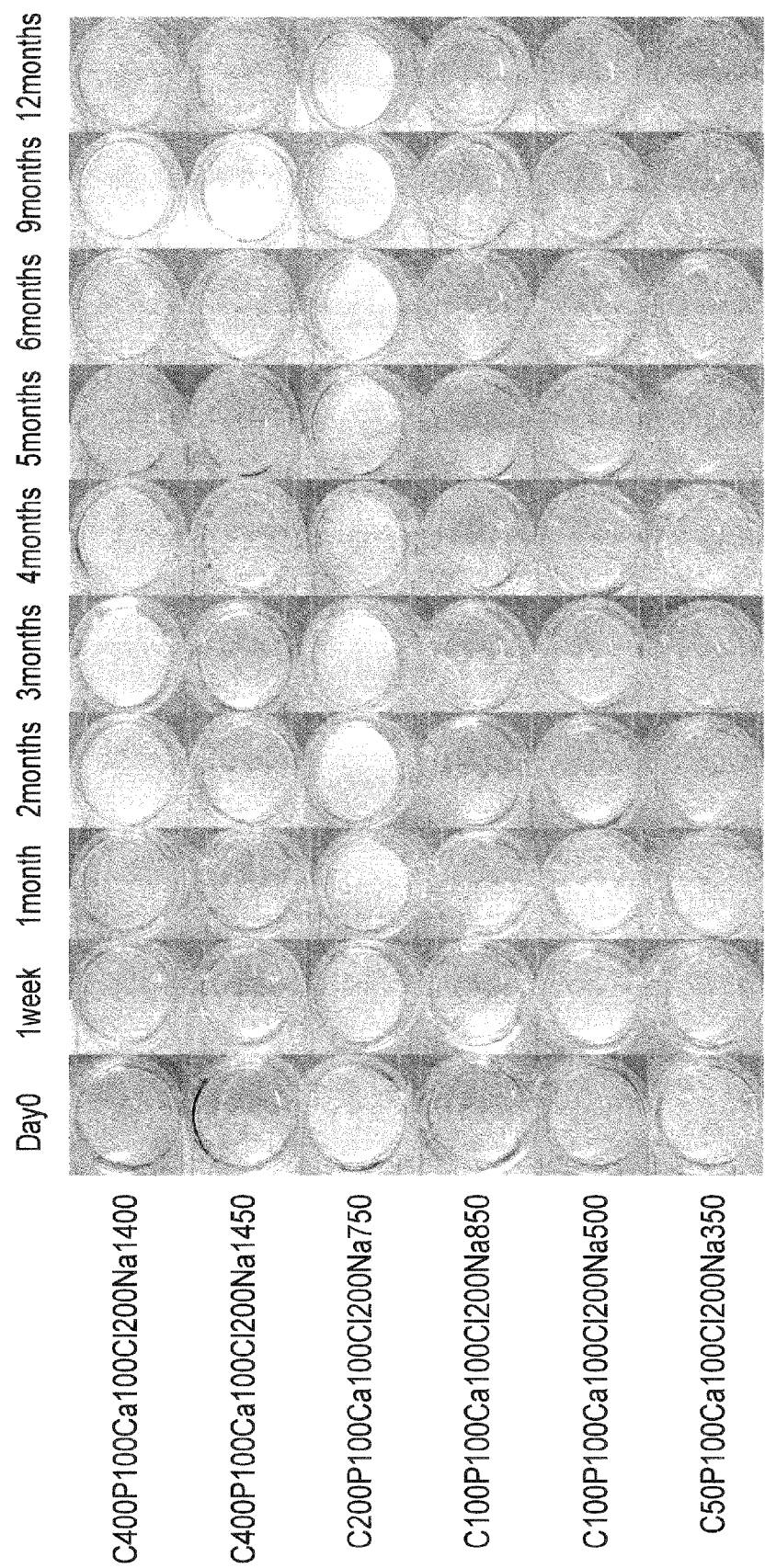
FIG. 2 is a view showing the results of Example 4 of the present invention.
Figure 3:
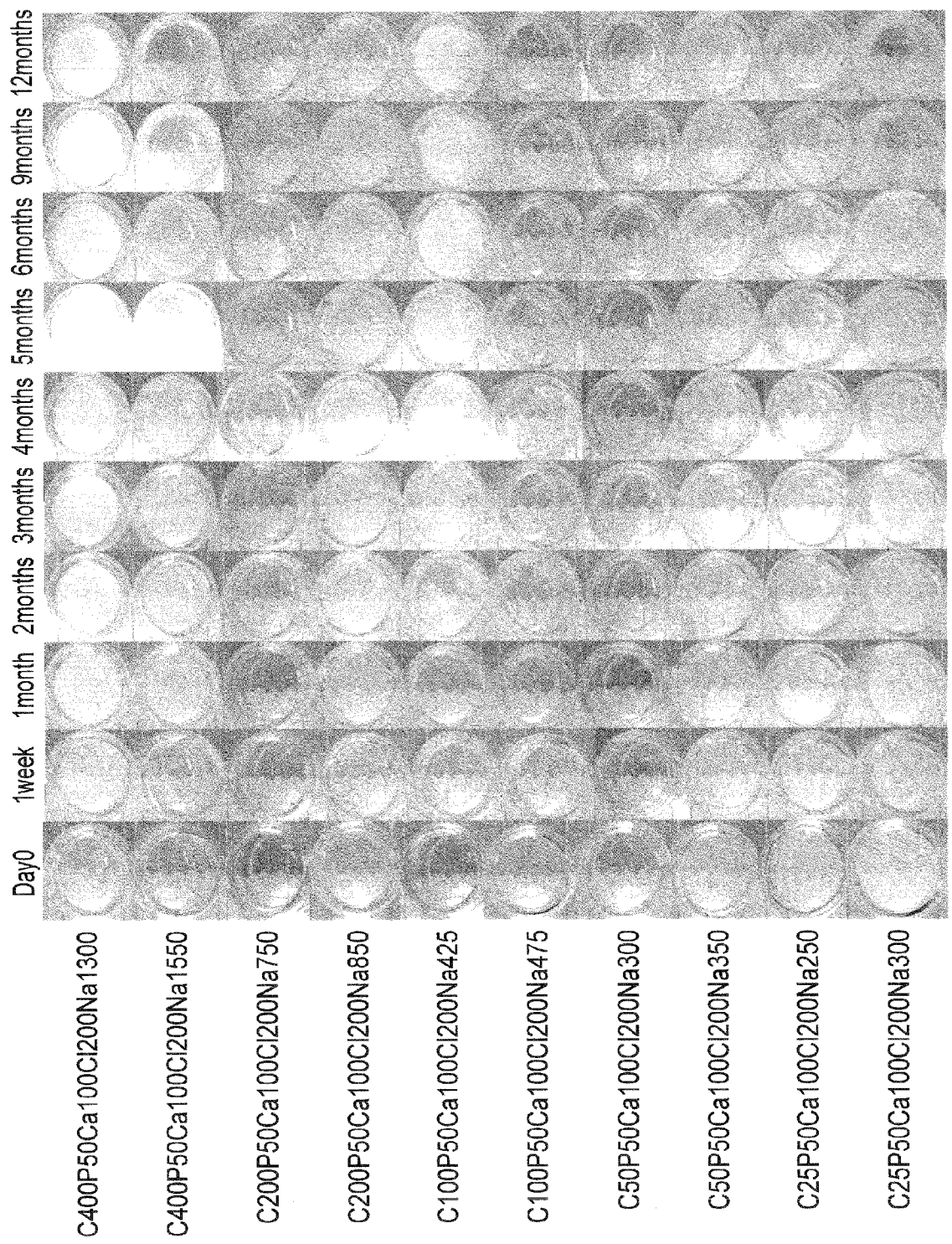
FIG. 3 is a view showing the results of Example 4 of the present invention.
Figure 4:
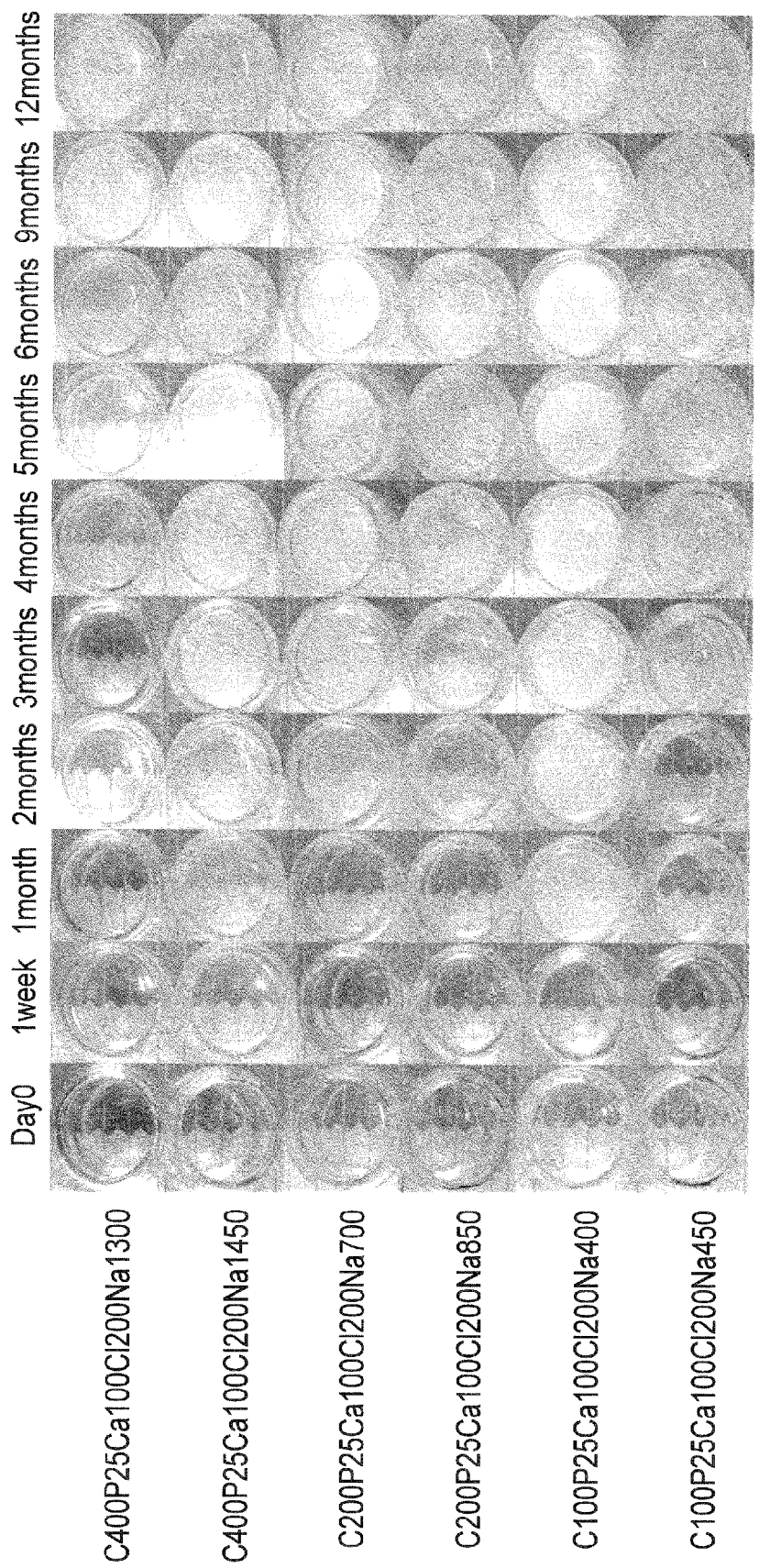
FIG. 4 is a view showing the results of Example 4 of the present invention.
Figure 5:
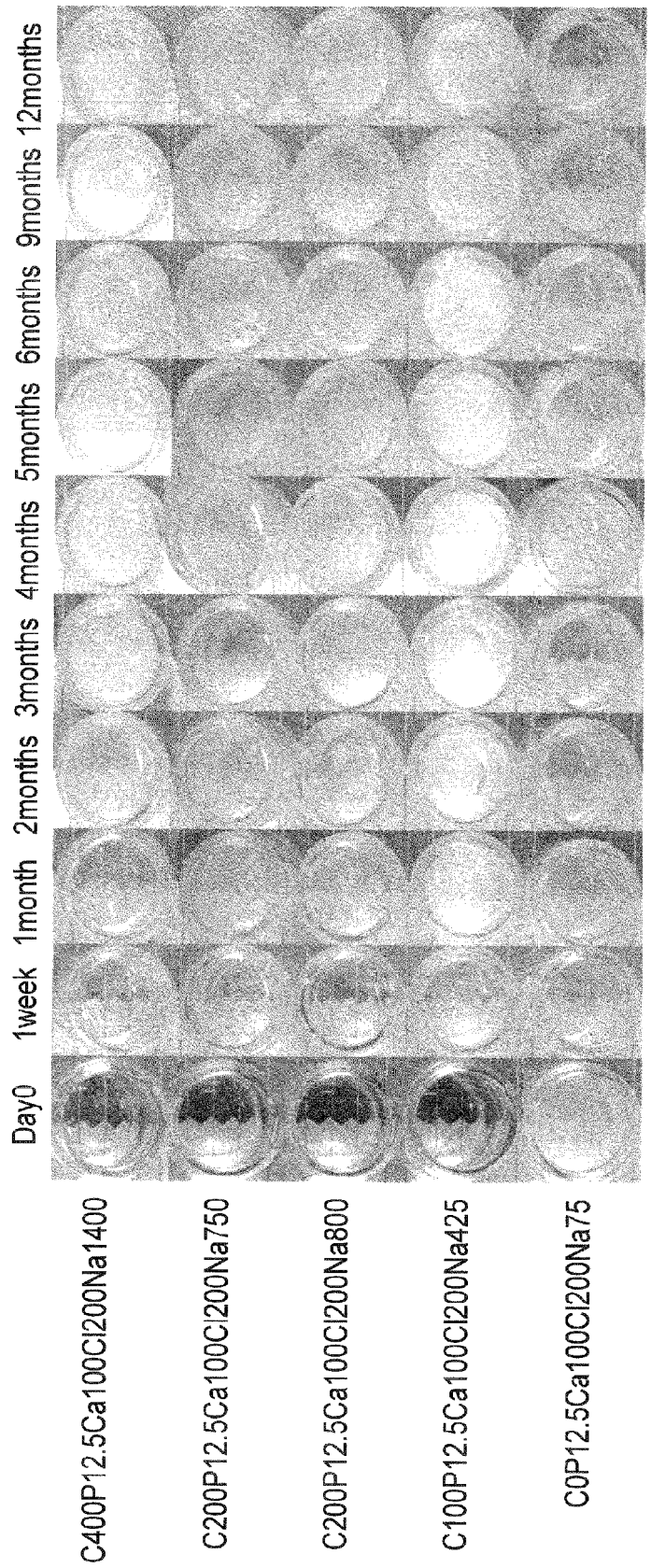
FIG. 5 is a view showing the results of Example 4 of the present invention.
Figure 7A:
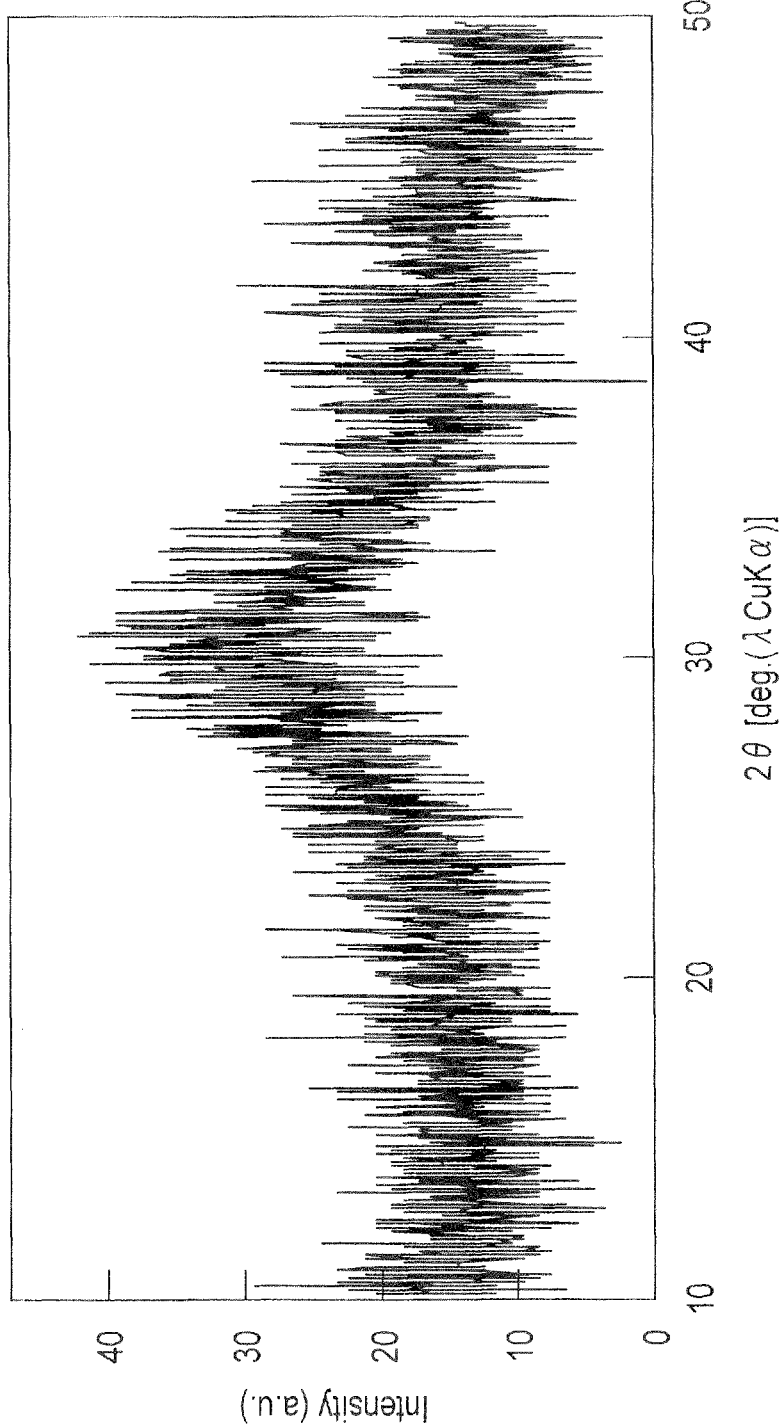
FIG. 7A is a view showing the results of Example 21 of the present invention.
Figure 7B:
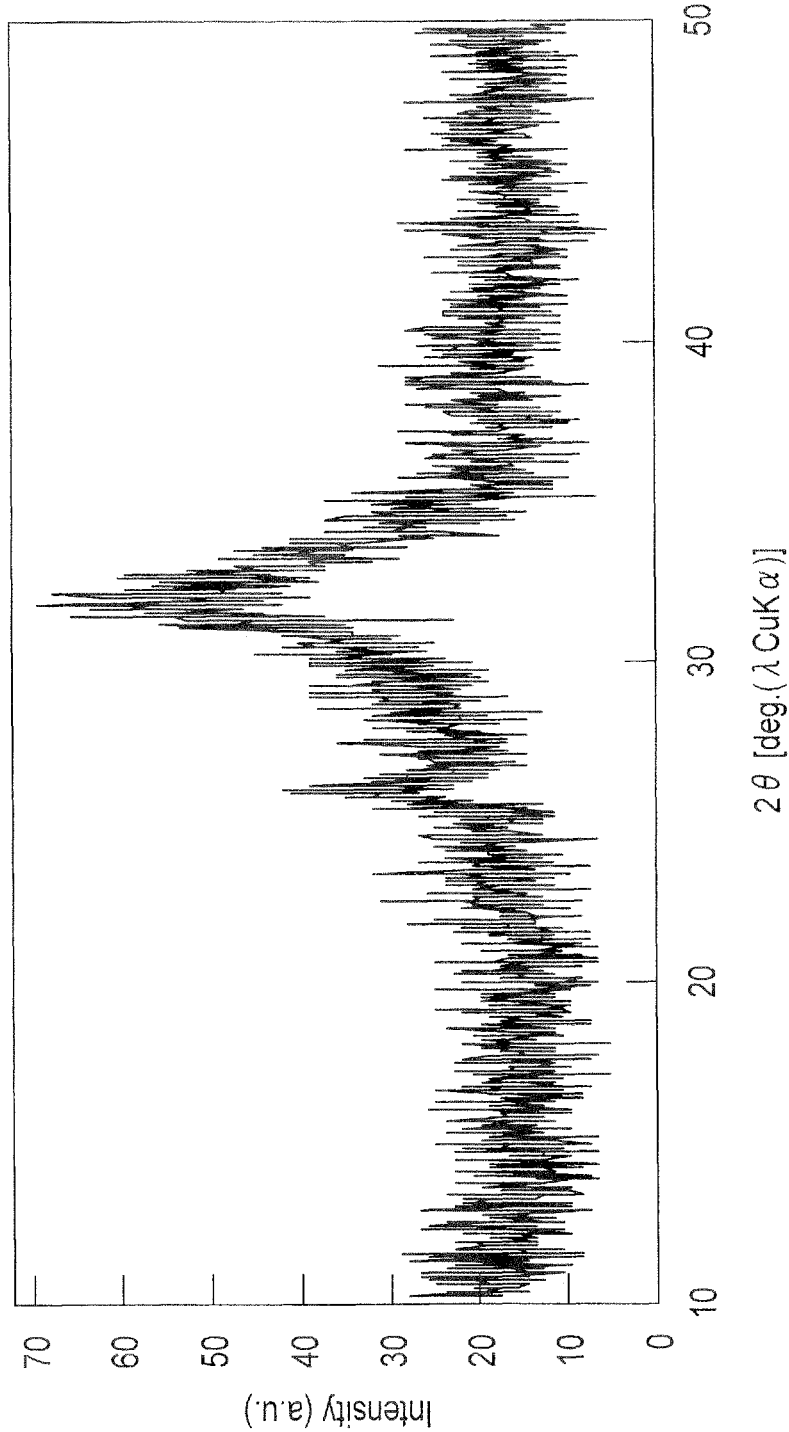
FIG. 7B is a view showing the results of Example 21 of the present invention.
Figure 7D:
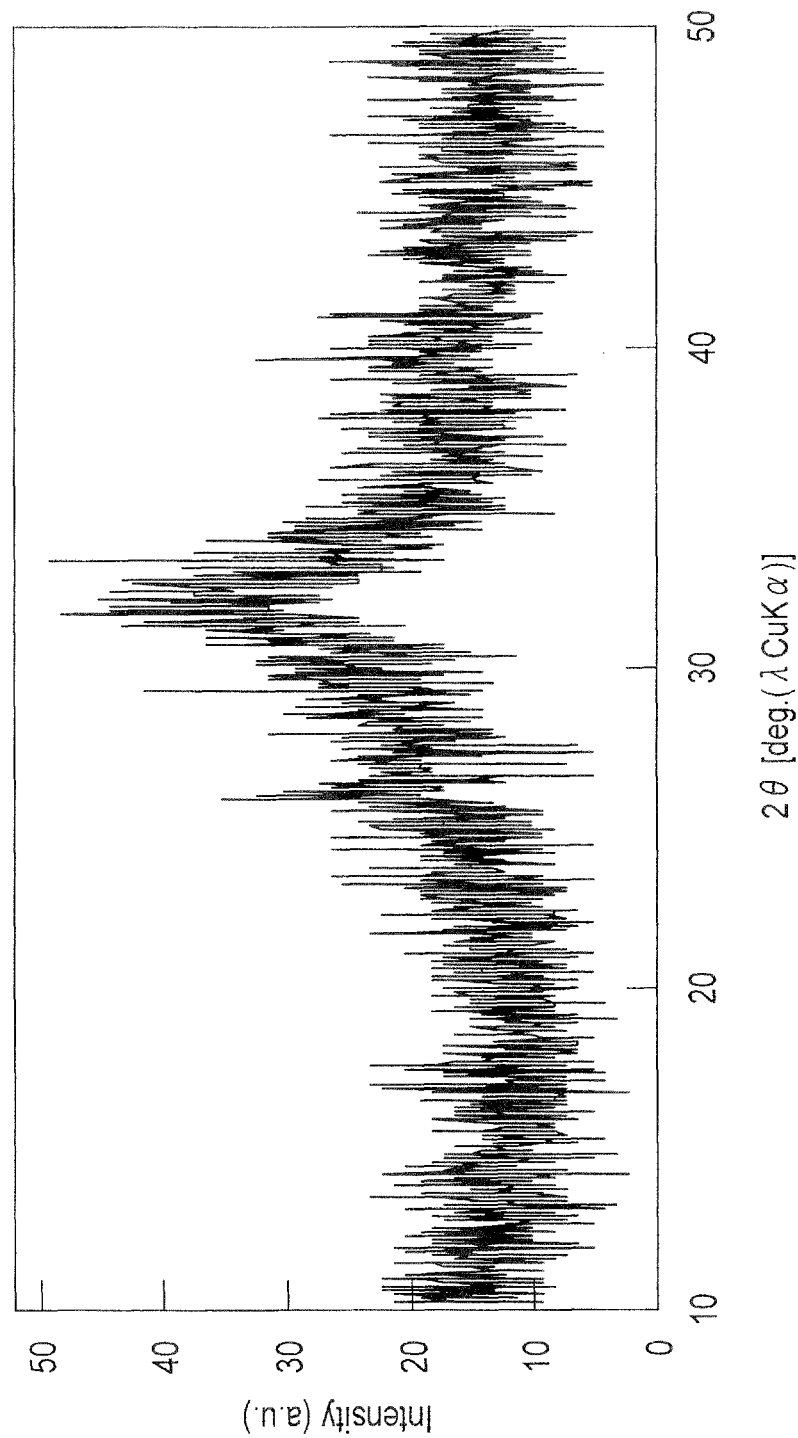
FIG. 7D is a view showing the results of Example 21 of the present invention.
Figure 8A:
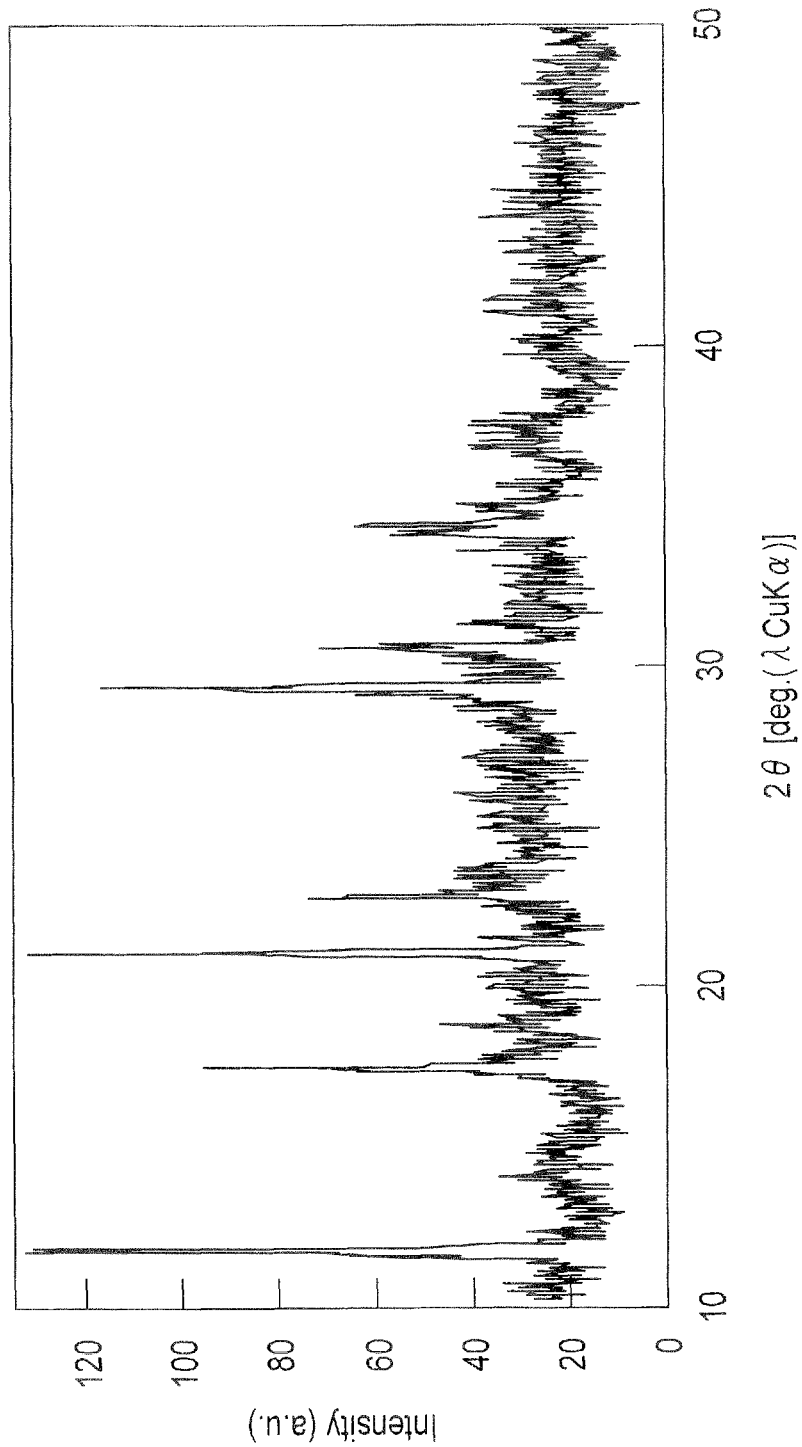
FIG. 8A is a view showing the results of Example 21 of the present invention.
Figure 8B:
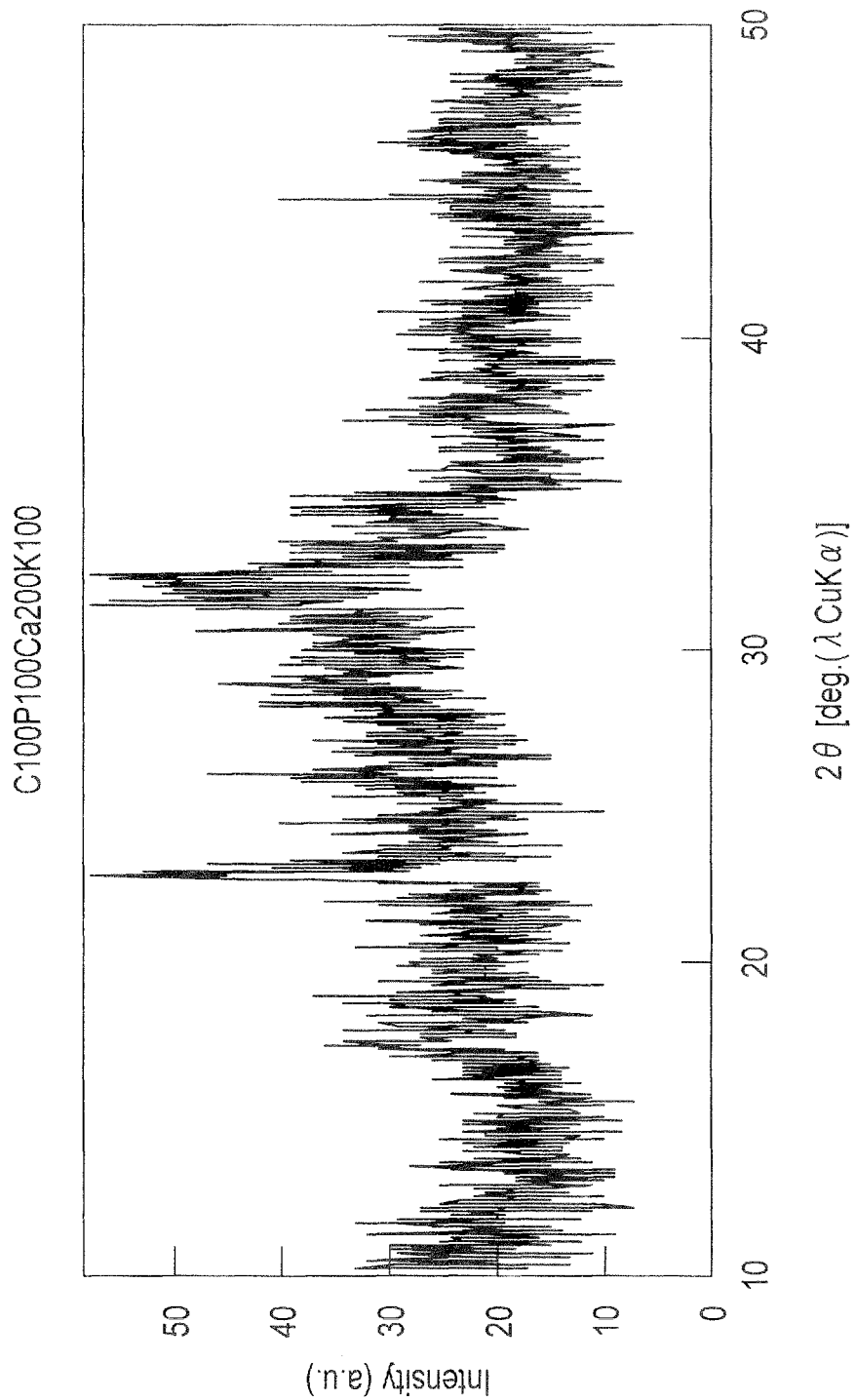
FIG. 8B is a view showing the results of Example 21 of the present invention.

Hereinafter, the embodiments of the invention will be described in detail.

1. CALCIUM PREPARATION

The calcium preparation of the present invention may be in solution form or may be in solid form obtained by drying the solution. In the case of the solution form, the calcium preparation is particularly referred to as "aqueous preparation of calcium". In the case of the solid form, the calcium preparation is particularly referred to as "solid preparation of calcium".

2. AQUEOUS PREPARATION OF CALCIUM

The aqueous preparation of calcium of the present invention is an aqueous preparation of calcium comprising water, calcium, a compound of Formula I, and a compound of Formula II as constituent elements, wherein most of the calcium is in non-ionic calcium form and forms a complex, wherein in the complex, the calcium binds to the compound of Formula I and/or the compound of Formula II in a state that basic structures of these compounds are kept, and at least a part of the complex forms colloidal particles, and wherein the aqueous preparation of calcium is a transparent aqueous preparation having a ph equal to or higher than that of slightly acid;

[Chemical formula 2]

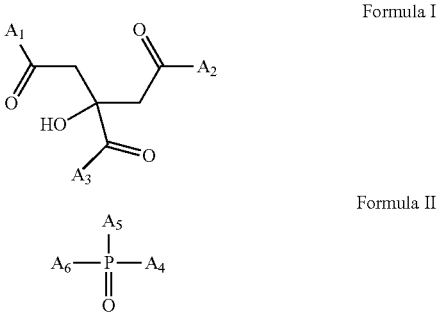

wherein, $A_1$, $A_2$, $A_3$, $A_4$, $A_5$ and $A_6$ are independently $O^-$ or OX, X represents a monovalent or polyvalent cation, and the Xs are the same or different when multiple OXs exist. Here, the "cation" may be a positive ion such as a hydrogen ion, a metal ion or an ammonium ion. In the aqueous preparation of calcium, X may be in a free state and/or non-free state.

Most of the calcium contained in the aqueous preparation of calcium is in non-ionic calcium form. The non-ionic calcium means calcium which is not detected by a calcium ion electrode, among all the calcium present in the solution.

When used as the non-ionic calcium contained in the aqueous preparation of calcium, the term "most" means that a ratio of the non-ionic calcium in all the calcium is about 98% or more, preferably about 99% or more, more preferably about 99.9% or more. For example, when the concentration of all the calcium is 100 mM, the ionic calcium detected is about 2 mM or less, preferably about 1 mM or less, more preferably about 0.1 mM or less.

The calcium present in non-ionic calcium form binds to the compound of Formula I and/or the compound of Formula II to form a complex. The compound of Formula I and/or the compound of Formula II contained in the complex binds to the calcium in a state that basic structures of these compounds are kept.

The aqueous preparation of calcium may further contain fluorine as a constituent element. When fluorine is contained, at least a part of the fluorine contained in the aqueous preparation of calcium is bound to the complex.

Unless otherwise described, the term "complex" used herein means a complex comprised of calcium and the compound of Formula I and/or the compound of Formula II, and also means a complex which is existing in situation that the complex is comprised of calcium and the compound Formula I and/or the compound of Formula II and then bound by fluorine, which is a subordinate concept.

At least a part of or the whole complex forms a colloid. The colloid can be confirmed by observing the Tyndall phenomenon which is a generally known means.

The aqueous preparation of calcium may further contain magnesium as a constituent element.

The term "compound of Formula I" is a generic term used to refer to "compound having a citric acid structure". Therefore, "citric acid", "citrate", and "citrate ion" are included in the compound of Formula I.

The term "compound of Formula II" is a generic term used to refer to a "compound having a phosphoric acid structure". Therefore, "phosphoric acid", "phosphate", and "phosphate ion" are included in the compound of Formula II.

The concentration of the compound of Formula I in the aqueous preparation of calcium may be, for example, about 25 mM or more based on 100 mM of calcium.

The concentration of the compound of Formula II in the aqueous preparation of calcium may be, for example, about 12.5 mM, preferably from about 25 to about 100 mM, more preferably about 50 mM based on 100 mM of calcium.

The transparency of the aqueous preparation of calcium can be determined based on, for example, the results of which the transparency is measured with visual and/or absorbance values. In the case of determining the transparency by visual judgment, it may be determined based on the absence of precipitates in the solution and the visibility level, in which a certain specific pattern (a figure such as a straight or wavy line, and a character) can be seen through the aqueous preparation of calcium. In the case of measuring it with absorbance values, for example, the absorbance value obtained by irradiating with light having a wavelength of 595 nm is about 0.3 or less when 100 µL of a solution is poured into a well of 96-well plates and measured with a microplate reader, if the solution has a calcium concentration of 100 mM. This value varies depending on the concentration of calcium and a measuring vessel.

The pH value of the aqueous preparation of calcium is equal to or higher than that of slightly acid. Here, the pH value equal to or higher than that of slightly acid means a pH value ranging from about 4 to about 13.

The average particle diameter of colloidal particles in the aqueous preparation of calcium is, for example, 100 nm or less, typically 50 nm or less. Further, the average particle diameter is, for example, 1 nm or more, typically 5 nm or more. Here, the term "average particle diameter" means a value measured by the dynamic light scattering method.

3. PRODUCTION METHOD

The production of the aqueous preparation of calcium may be performed by, for example, a method characterized in: mixing a calcium source ionized in water with a source of a compound of Formula I and a source of a compound of Formula II; and converting the obtained liquid from an opaque liquid to a transparent liquid under the condition where the pH of a final solution is equal to or higher than that of slightly acid.

The production method may be a method consisting of: ionizing a calcium source in water; mixing the calcium ionized with a source of a compound of Formula I and a source of a compound of Formula II; and converting the obtained liquid from an opaque liquid to a transparent liquid under the condition where the pH of a final solution is equal to or higher than that of slightly acid, a method comprising: ionizing a calcium source in water; mixing the ionized calcium with a source of a compound of Formula I and a source of a compound of Formula II; and converting the obtained liquid from an opaque liquid to a transparent liquid under the condition where the pH of a final solution is equal to or higher than that of slightly acid, or a method including or comprising the above steps.

The calcium source may be any calcium salt that is known. Examples thereof include calcium chloride, calcium hydroxide, calcium lactate, calcium nitrate, calcium sulfate, calcium carbonate, calcium oxide, calcium bis(dihydrogenphosphate), calcium hydrogenphosphate, calcium diphosphate, tricalcium phosphate, and calcium citrate. As the calcium source, one kind of calcium salt may be used or two or more kinds of calcium salts may be used. In addition, when particularly, the calcium preparation of the present invention is used for a food application, a calcined calcium which contains calcium oxide as a main component may be used as the calcium source.

Water may be selected from any water that is known, such as tap water, distilled water, ion exchange water, purified water, ultrapure water, and sterilized water for injection according to the application.

Examples of a source of the compound of Formula I include citric acid, potassium citrate monobasic, tripotassium citrate, calcium citrate, ferric citrate, and trisodium citrate. For example, a combination of one or two or more kinds of these sources may be used as a source of the compound of Formula I.

Examples of a source of the compound of Formula II include phosphoric acid, potassium dihydrogenphosphate, dipotassium hydrogen phosphate, tripotassium phosphate, sodium dihydrogenphosphate, disodium hydrogenphosphate, trisodium monophosphate, ammonium phosphate monobasic, diammonium phosphate, calcium hydrogenphosphate, and calcium diphosphate. A combination of one or two or more kinds of these sources may be used as a source of the compound of Formula II.

Ionization of the calcium source in water may be performed by a method of dissolving the calcium source in any of the above types of water. In the dissolving process, calcium salts have a low solubility in water depending on the kinds of calcium salts which are used as the calcium source. In such a case, it is necessary to ionize the calcium source by decreasing the pH value of water to be used so as to make it acidic. When a highly water-soluble calcium source is used, it may be ionized in water which is weakly acidic, neutral or basic.

The acid which is used to adjust the pH value when ionizing the calcium source may be any acid known itself in the art which is generally used to adjust the pH. According to the kind of calcium salt, the calcium source may be ionized using citric acid used as a compound of Formula I and/or phosphoric acid used as a source of a compound of Formula II.

The reaction of the ionized calcium source with the compound of Formula I and the compound of Formula II can be performed by allowing the ionized calcium source and the sources of the compound of Formula I and the compound of Formula II to coexist in water and to be in contact with each other. In this contact, it is desired that the sources of the compound of Formula I and the compound of Formula II are dissolved.

In order to bring the ionized calcium into contact with the sources of the compound of Formula I and the compound of Formula II, the sources of the compound of Formula I and the compound of Formula II may be added to the solution containing the ionized calcium, the sources of the compound of Formula I and the compound of Formula II contained in the solution may be added to the calcium source, or either of the sources of the compound of Formula I or the compound of Formula II contained in the solution is added to the calcium source, followed by addition of the remaining source. The source of the compound of Formula I and the source of the compound of Formula II may be added simultaneously. Alternatively, either of them is added and then the other may be added. The first contact of the calcium source with the source of the compound of Formula I and/or the source of the compound of Formula II may be performed simultaneously with the ionization of the calcium source, or may be performed after the calcium source is ionized. As a further addition, the calcium source, the source of the compound of Formula I and/or the source of the compound of Formula II may be added to a mixture formed by the first contact.

The source of the compound of Formula I and the source of the compound of Formula II to be added may be added to a solution containing the ionized calcium after being predissolved in water or may be dissolved after being added to the solution. Preferably, the sources are added to the solution containing the ionized calcium after being predissolved in water. When the source of the compound of Formula I and the source of the compound of Formula II are predissolved in water, the source of the compound of Formula I and the source of the compound of Formula II may be prepared as different solutions, or may be prepared as a solution containing the sources of the compound of Formula I and the compound of Formula II. Preferably, the sources are prepared as different solutions. The preparation may be performed by dissolving the source of the compound of Formula I into any of the above types of water or dissolving the source of the compound of Formula II into any of the above types of water.

When the aqueous preparation of calcium further contains fluorine or magnesium as constituent elements, the fluorine source or the magnesium source may be brought into contact with the calcium source simultaneously with, prior to, or subsequent to the contact of the calcium source with the source of the compound of Formula I and/or the source of the compound of Formula II. Preferably, after predissolving the fluorine source or the magnesium source in water to give a solution, the solution is simultaneously or sequentially mixed with a solution of the source of the compound of Formula I, a solution of the source of the compound of Formula II, and a solution of the calcium source which are similarly prepared by dissolving in water. However, the present invention is not limited thereto. Similarly to the source of the compound of Formula I and the source of the compound of Formula II, the contact of the calcium source with the fluorine source or the magnesium source may be achieved by any of the above methods.

The fluorine source may be a fluoride such as sodium fluoride, potassium fluoride, calcium fluoride or magnesium fluoride.

Examples of the magnesium source include magnesium chloride, magnesium hydroxide, magnesium lactate, magnesium nitrate, magnesium sulfate, magnesium carbonate, magnesium oxide, magnesium bis(dihydrogen phosphate), magnesium hydrogenphosphate, magnesium diphosphate, trimagnesium phosphate, and magnesium citrate.

The calcium source may be added to a solution of the source of the compound of Formula I and/or a solution of the source of the compound of Formula II and/or a solution of any fluorine source or magnesium source. In that case, it is necessary that the calcium source added to the solution is present in an ionized state before the start of the reaction.

The reaction of the ionized calcium source with sources of the compound of Formula I and the compound of Formula II is initiated by allowing them to coexist and bring them into contact with one another in water. The reaction solution may be stirred during the reaction or may be allowed to stand. When using the condition where the pH of a final solution is equal to or higher than that of slightly acid before the start of the reaction or during the reaction, the conversion from an opaque liquid to a transparent liquid proceeds.

The conversion from an opaque liquid to a transparent liquid of the obtained solution is also achieved by allowing the liquid to stand at room temperature.

The conversion from an opaque liquid to a transparent liquid is performed under the condition where the pH of a final solution is equal to or higher than that of slightly acid. Therefore, the condition may be satisfied by adjusting the pH so that the pH of a final solution is equal to or higher than that of slightly acid. For example, prior to the contact of the ionized calcium source, the source of the compound of Formula I, the source of the compound of Formula II, and any fluorine source and/or magnesium source, the pH of a solution containing at least one of these substances may be adjusted so that the pH of a final solution is equal to or higher than that of slightly acid. In the pH adjustment, any acid known itself and/or base may be used to adjust the pH. The pH adjustment may be performed using any adjusting liquid known itself, such as a sodium hydroxide solution, a potassium hydroxide solution, hydrochloric acid, sulfuric acid, and nitric acid.

In the pH adjustment, a predetermined amount of a basic solution and/or an acidic solution may be added at a stage of the opaque liquid so as to obtain a final appropriate pH value, namely, a pH equal to or higher than that of slightly acid. For example, it is necessary to adjust the pH value so that the pH value of the aqueous preparation of calcium to be finally obtained is about 4 or more, about 4 to about 13, about 5 to about 13, about 8 to about 13, about 10 to about 13, or about 12 to about 13.

As described above, the aqueous preparation of calcium of the present invention has a pH value equal to or higher than that of slightly acid. The pH of the reaction solution may be changed so that the aqueous preparation of calcium to be finally obtained has a pH value equal to or higher than that of slightly acid during reaction and/or during conversion from an opaque liquid to a transparent liquid.

Further, the conversion from an opaque liquid to a transparent liquid can be performed by allowing the solution to stand, for example, at about 4° C. to about 90° C. for about 3 hours to one week, preferably for about 12 hours to about one week. The time length of the conversion varies depending on the temperature. The conversion period is also referred to as "aging".

The conversion from en opaque liquid to a transparent liquid may be interpreted as the conversion from a non-colloidal liquid to a colloidal liquid.

The transparency of the aqueous preparation of calcium obtained by such a process is maintained without producing precipitates derived from calcium ions or calcium salts over a long period of time, for example, semi-permanently or at least six months, one month, three weeks, two weeks, one week or five days or 3 days or more.

It is possible to store the aqueous preparation of calcium at about −80° C. to about 90° C. and the transparency is maintained regardless of the storage temperature. The term "stable" used herein means a state in which the transparency of the solution is maintained without precipitates and white turbidity. The determination of the transparency can be derived from the results of which a solution is measured with visual judgment values and/or absorbance values. A specific pattern can be determined visually through the solution to be determined. When the white turbidity and precipitates are not observed, the solution is determined to "be transparent". In the case of the absorbance values, for example, when 100 μL of solution in 1 well of 96-well microplates is measured at 595 nm, the value is 0.3 or less. Further, when it is confirmed that precipitates are not observed visually, the solution may be determined to "be transparent". One of the visual determination and the determination with absorbance values may be performed or both of them may be used in combination.

The aqueous preparation of calcium according to the present invention can be obtained by the above method. The aqueous preparation of calcium to be obtained as a final product maintains all the components derived from the calcium source used in the production process, the source of the compound of Formula I, and the source of the compound of Formula II as constituents.

4. SOLID PREPARATION OF CALCIUM

The aqueous preparation of calcium described above (for example, the aqueous preparation of calcium produced by the above method) can be solidified by any drying means, such as freeze-drying, hot air drying, air-drying, or spray drying. The solidified solid preparation of calcium is stable over a long period of time. Moreover, when the solid preparation is dissolved in a solution, such as water, a salt solution or sugar solution, the aqueous preparation of calcium according to the present invention can be reconstituted.

For example, freeze-drying of the aqueous preparation of calcium may be performed by any freeze drying method known. For example, it is freezed at 0° C. to −80° C. and may be dried with any freeze dryer known.

5. APPLICATION

The calcium preparation according to the present invention (i.e., the aqueous preparation of calcium and the solid preparation of calcium) exhibits excellent stability over a long period of time. In other words, when the preparation is in solution form, precipitates derived from calcium ions or salts are not generated over a long period of time. Further, the preparation has very little bitterness that is characteristic of calcium and thus it is useful for oral ingestion. Even when the preparation is orally ingested, good absorbency can be expected.

The calcium preparation may be used alone or in combination with other active components and/or accessory component which may be used as drugs such as calcium preparations for applying calcium to a subject, quasi-drugs, supplements, and food additive for calcium-rich food products.

Other active components may be medically active drugs, nutritionally active components or components capable of exhibiting efficacy for other purposes.

The accessory component may be any known additive. Examples of the additive may include diluting agents, sweetening agents, flavoring agents, antiseptic agents, and/or preserving agents.

Even if the aqueous preparation of calcium or the solid preparation of calcium is mixed with other various types of solutions, it hardly precipitates. Therefore, the preparation can be mixed with other solutions to produce drugs of pharmaceutical solution form or quasi-drugs, cosmetics, supplements, drinks or the like.

Further, the calcium preparation can be mixed with any other solid to produce drugs, quasi-drugs, cosmetics, supplements, drinks, and food products. In that case, the calcium preparation to be used may be the aqueous preparation of calcium or the solid preparation of calcium. As described above, the aqueous preparation of calcium according to the present invention is transparent. In general, it is considered that a transparent calcium solution has good absorbency. Therefore, it is considered that drugs, quasi-drugs, and food products containing the calcium preparation according to the present invention contain calcium in an excellent absorptive form.

Further, the calcium solution may be used to efficiently apply calcium to a subject in fields such as agriculture, fishery, stock farming, and horticulture.

6. METHOD OF PREVENTING FORMATION OF PRECIPITATES IN CALCIUM SOLUTION

According to the present invention, the method of producing the above aqueous preparation of calcium may be provided as a method of preventing the formation of precipitates in a calcium solution. In that case, in order to prevent, the formation of precipitates derived from calcium in a calcium solution, the method may be a method characterized in: mixing the calcium which is ionized in water with a compound of Formula I and a compound of Formula II; and converting the obtained liquid from an opaque liquid to a transparent liquid under the condition where the pH of a final solution is equal to or higher than that of slightly acid. This method may be a method consisting of: ionizing a calcium source in water; mixing the ionized calcium with a compound of Formula I and a compound of Formula II; and converting the obtained liquid from an opaque liquid to a transparent liquid under the condition where the pH of a final solution is equal to or higher than that of slightly acid, or a method including the above steps.

Particularly, each process may be performed in the same manner as described in the above production method.

7. EXAMPLE

Example 1

Production of Aqueous Preparation of Calcium Using Calcium Chloride

A 2 M citric acid solution (4 M when the calcium concentration of the sample liquid to be finally prepared was 400 mM or more), a 2 M phosphoric acid solution, (4 M when the calcium concentration of the sample liquid to be finally prepared was 400 mM or more), a 5 M calcium chloride solution, and a 5 M sodium hydroxide solution (10 M when the calcium concentration of the sample liquid to be finally prepared was 400 mM or more) were prepared using distilled water. Subsequently, a citric acid solution, a phosphoric acid solution, a sodium hydroxide solution, and distilled water were mixed such that the concentration is a predetermined concentration so that a mixed liquid is obtained. A calcium chloride solution was added to the mixed liquid and mixed such that the concentration is a predetermined concentration. Thereafter, the mixture was allowed to stand at 37° C. for one week to obtain a sample liquid.

For example, 1000 μL of a 2 M citric acid solution, 250 μL of a 2 M phosphoric acid solution, 1100 μL of a 5 M sodium hydroxide solution, and 7250 μL of distilled water were mixed in a test tube in the case of the aqueous preparation of calcium of 200 mM citric acid, 50 mM phosphoric acid, 100 mM calcium, 200 mM chloride, and 550 mM sodium. Then, 200 μL of a 5 M calcium chloride solution was added to a 15 mL-volume snap vial and 4800 μL of the mixed liquid was added thereto, and then was mixed. Thereafter, the mixture was allowed to stand at 37° C. for one week to obtain a sample liquid.

As for the obtained solution, the pH (pH/ION METER F-53, Electrode 9610-100, HORIBA, Ltd.), calcium ion concentration (pH/ION METER F-53, Ion cluster electrode 6583-10C, Chip electrode #7683, HORIBA, Ltd.), and absorbance value (100 μL per well of 96-well plates, O.D. 595 nm, BioTek Instruments plate reader, EL312e) were measured. The sample liquid in the glass container was irradiated with laser light from the side surface, and the Tyndall phenomenon was observed in the dark.

The concentration and analysis value as for each component of the obtained solution are shown in the Tables and the information of transparency is shown by the lightness of the background of each cell in the Table.

A typical reading of the Table is shown in Table 1.

TABLE 1

|  | pH | Ca (μM) | pH | Ca (μM) | pH | Ca (μM) |
|---|---|---|---|---|---|---|
| NaOH concentration (mM) |  | 1450 |  | 1550 |  | 1600 |
| C400P100Ca100Cl1200 | 7.63 | 2.43 | 12.27 | 0.29 | 12.64 | 0.47 |
| Transparency |  | A |  | D |  | D |
| NaOH concentration (mM) |  | 850[1] |  | 950 |  | 1000 |
| C200P100Ca100Cl1200[2] | 7.23[3] | 5.17[4] | 12.31 | 0.09 | 12.64 | 0.13 |
| Transparency |  | A[5] |  | D[5] |  | D[5] |

[1]Concentration of sodium hydroxide (value obtained by converting the additive amount of each component to a final concentration of the sample liquid (mM))
[2]C200: Concentration of citric acid (value obtained by converting the additive amount of each component to a final concentration of the sample liquid (mM))
P100: Concentration of phosphoric acid (value obtained by converting the additive amount of each component to a final concentration of the sample liquid (mM))
Ca100: Concentration of calcium (value obtained by converting the additive amount of each component to a final concentration of the sample liquid (mM))
Cl1200: Concentration of chloride (value obtained by converting the additive amount of each component to a final concentration of the sample liquid (mM))
[3]pH
[4]Concentration of calcium ions (measurement value: μm)
[5]Range of transparency of the present invention:

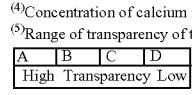

As for the symbols in the Table, C represents citric acid, P represents phosphoric acid, Ca represents calcium, and Cl represents chlorine. Further, each numerical value represents a value obtained by converting the additive amount of each component to a final concentration of the sample liquid (mM). For example, the description of "C400P200Ca100Cl1200" represents a solution of 400 mM citric acid, 200 mM phosphoric acid, 100 mM calcium, and 200 mM chlorine.

The transparency of the sample liquid was evaluated in four stages: "A"; "B"; "C"; and "D" in descending order of transparency. Among them, the sample whose transparency is evaluated as "A", "B", or "C" corresponds to the aqueous preparation of calcium of the present invention.

Information about each sample liquid is represented by, for example, one cell arranged in the column of "Concentration of NaOH (mM)" in Table 1 and one cell just below the cell, i.e., one cell arranged in the column of "C400P100Ca100Cl1200". In this case, the numerical value included in the upper cell represents a value obtained by converting the additive amount of sodium hydroxide to the sample liquid to a final concentration of the sample liquid. As for the numerical value just below the cell, i.e., the numerical value included in the lower cell, the value on the left represents a pH value of a final sample liquid and the value on the right represents the concentration of free calcium ions (μM) of a final sample liquid.

Further, the information about sodium fluoride was also shown in Table 11-1 described in Example 6. In each cell arranged in the column of "Concentration of NaF (mM)", a value obtained by converting the additive amount of sodium fluoride to the sample liquid to a final concentration of the sample liquid (mM) is shown. For example, in each cell included in the column of each sample liquid shown by the description of "C100P100Ca200NaOH100", the pH value of a final sample liquid is given on the left, the concentration of free calcium ions (μM) of a final sample liquid is given at the center, and further the concentration of free fluoride ions of a final sample liquid (μM) is given on the right.

The information about magnesium is also shown in each table described in Example 18. Specifically, the calcium concentration (additive amount; mM), magnesium concentration (additive amount; mM), and chloride concentration (additive amount; mM) are shown, starting from the left, in the line of "Concentration of Ca:Mq:Cl (mM)".

The absorbance values about the sample liquids having each condition are shown in Table 2-2.

Regarding the table, when the table number includes a subdivision and this is omitted in the description, it is intended that tables corresponding to all the subdivisions included in the described table numbers are collectively referred to as a series. For example, "Table 2-1" collectively means "Table 2-1-1", "Table 2-1-2", "Table 2-1-3", "Table 2-1-4", "Table 2-1-5", and "Table 2-1-6".

The results of Example 1 above are shown in Table 2. Table 2 shows the results when the concentration of calcium was fixed at 100 mM, citric acid was modified at a concentration of 0 to 400 mM, and phosphoric acid was modified at a concentration of 0 to 200 mM.

TABLE 2-1

|  |  | pH | Ca (μM) | pH | Ca (μM) | pH | Ca (μM) | pH | Ca (μM) | pH | Ca (μM) |
|---|---|---|---|---|---|---|---|---|---|---|---|
| P200 | Concentration of NaOH (mM) | 1300 |  | 1400 |  | 1500 |  | 1600 |  | 1700 |  |
|  | C400P200Ca100Cl200 | 5.47 | — | 5.93 | — | 6.33 | — | 6.93 | 6.06 | 9.97 | 0.34 |
|  | Transparency | D |  | D |  | D |  | D |  | D |  |

TABLE 2-1-continued

|  |  |  |  |  |  |  |  |  |  |  |
|---|---|---|---|---|---|---|---|---|---|---|
|  | Concentration of NaOH (mM) | 850 |  | 900 |  | 950 |  | 1000 |  | 1050 |  |
|  | C200P200Ca100Cl200 | 5.92 | — | 6.04 | 48.8 | 6.35 | 18.6 | 6.78 | 7.28 | 7.51 | 1.8 |
|  | Transparency | D |  | D |  | D |  | D |  | D |  |
|  | Concentration of NaOH (mM) | 500 |  | 550 |  | 600 |  | 650 |  | 700 |  |
|  | C100P200Ca100Cl200 | 5.28 | — | 5.41 | 346 | 5.72 | 117 | 6.22 | 28.3 | 6.67 | 12.4 |
|  | Transparency | D |  | D |  | D |  | D |  | D |  |
|  | Concentration of NaOH (mM) | 400 |  | 450 |  | 500 |  | 550 |  | 600 |  |
|  | C50P200Ca100Cl200 | 5.2 | — | 5.48 | 261 | 6.09 | 41.1 | 6.65 | 13 | 7.54 | 2.75 |
|  | Transparency | D |  | D |  | D |  | D |  | D |  |
|  | Concentration of NaOH (mM) | 350 |  | 400 |  | 450 |  | 500 |  | 550 |  |
|  | C25P200Ca100Cl200 | 5.06 | — | 5.6 | 138 | 6.34 | 26.1 | 6.98 | 7.13 | 9.52 | 0.33 |
|  | Transparency | D |  | D |  | D |  | D |  | D |  |
|  | Concentration of NaOH (mM) | 300 |  | 350 |  | 400 |  | 450 |  | 500 |  |
|  | C12.5P200Ca100Cl200 | 4.27 | — | 5.07 | 738 | 6.13 | 54.6 | 6.82 | 12 | 7.76 | 2.6 |
|  | Transparency | D |  | D |  | D |  | D |  | D |  |
|  | Concentration of NaOH (mM) | 250 |  | 300 |  | 350 |  | 400 |  | 450 |  |
|  | C0P200Ca100Cl200 | 3.31 | — | 5.26 | — | 5.92 | 112 | 6.65 | 22.7 | 7.53 | 4.27 |
|  | Transparency | D |  | D |  | D |  | D |  | D |  |
| P100 | Concentration of NaOH (mM) | 1250 |  | 1300 |  | 1350 |  | 1400 |  | 1450 |  |
|  | C400P100Ca100Cl200 | 5.84 | — | 6.23 | — | 6.65 | — | 6.82 | 11 | 7.63 | 2.43 |
|  | Transparency | D |  | D |  | D |  | B |  | A |  |
|  | Concentration of NaOH (mM) | 650 |  | 700 |  | 750 |  | 800 |  | 850 |  |
|  | C200P100Ca100Cl200 | 5.51 | — | 5.9 | — | 6.04 | 67.4 | 6.43 | 22.9 | 7.23 | 5.17 |
|  | Transparency | D |  | D |  | B |  | B |  | A |  |
|  | Concentration of NaOH (mM) | 350 |  | 400 |  | 450 |  | 500 |  | 550 |  |
|  | C100P100Ca100Cl200 | 4.37 | — | 5.57 | — | 5.58 | — | 6.01 | 70 | 7 | 7.53 |
|  | Transparency | D |  | D |  | D |  | B |  | C |  |
|  | Concentration of NaOH (mM) | 200 |  | 250 |  | 300 |  | 350 |  | 400 |  |
|  | C50P100Ca100Cl200 | 3.49 | — | 4.07 | — | 5.29 | — | 5.67 | 234 | 6.74 | 17.6 |
|  | Transparency | D |  | D |  | D |  | C |  | D |  |
|  | Concentration of NaOH (mM) | 150 |  | 200 |  | 250 |  | 300 |  | 350 |  |
|  | C25P100Ca100Cl200 | 3.74 | — | 4.03 | — | 15.05 | — | 6.06 | 160 | 9.35 | 0.7 |
|  | Transparency | D |  | D |  | D |  | D |  | D |  |
|  | Concentration of NaOH (mM) | 50 |  | 100 |  | 150 |  | 200 |  | 250 |  |
|  | C12.5P100Ca100Cl200 | 1.95 | — | 2.83 | — | 3.74 | — | 4.65 | — | 5.33 | 610 |
|  | Transparency | A |  | A |  | D |  | D |  | D |  |
|  | Concentration of NaOH (mM) | 0 |  | 50 |  | 100 |  | 150 |  | 200 |  |
|  | C0P100Ca100Cl200 | 1.38 | — | 1.93 | — | 3.17 | — | 3.87 | — | 5 | — |
|  | Transparency | A |  | A |  | D |  | D |  | D |  |
| P50 | Concentration of NaOH (mM) | 1200 |  | 1250 |  | 1300 |  | 1350 |  | 1400 |  |
|  | C400P50Ca100Cl200 | 5.97 | — | 6.5 | — | 6.9 | 21.4 | 8.75 | 4.27 | 12.17 | 0.51 |
|  | Transparency | D |  | D |  | A |  | A |  | A |  |
|  | Concentration of NaOH (mM) | 550 |  | 600 |  | 650 |  | 700 |  | 750 |  |
|  | C200P50Ca100Cl200 | 5.16 | — | 5.32 | — | 5.88 | — | 6.22 | — | 7.07 | 39.1 |
|  | Transparency | D |  | D |  | D |  | D |  | A |  |
|  | Concentration of NaOH (mM) | 325 |  | 350 |  | 375 |  | 400 |  | 425 |  |
|  | C100P50Ca100Cl200 | 4.98 | — | 5.65 | — | 5.9 | — | 6.04 | — | 6.16 | 268 |
|  | Transparency | D |  | D |  | D |  | D |  | A |  |
|  | Concentration of NaOH (mM) | 175 |  | 200 |  | 225 |  | 250 |  | 275 |  |
|  | C50P50Ca100Cl200 | 3.65 | — | 4.28 | — | 4.9 | — | 5.46 | — | 5.9 | — |
|  | Transparency | D |  | D |  | D |  | D |  | D |  |
|  | Concentration of NaOH (mM) | 150 |  | 175 |  | 200 |  | 225 |  | 250 |  |
|  | C25P50Ca100Cl200 | 4.39 | — | 4.7 | — | 5.28 | — | 6.08 | 1340 | 10.61 | 64.6 |
|  | Transparency | D |  | D |  | D |  | D |  | A |  |
|  | Concentration of NaOH (mM) | 125 |  | 150 |  | 175 |  | 200 |  | 225 |  |
|  | C12.5P50Ca100Cl200 | 4.82 | — | 4.95 | 19300 | 5.22 | 10200 | 6.6 | 1960 | 11.54 | 42.5 |
|  | Transparency | D |  | D |  | D |  | D |  | D |  |
|  | Concentration of NaOH (mM) | 50 |  | 75 |  | 100 |  | 125 |  | 150 |  |
|  | C0P50Ca100Cl200 | 3.57 | — | 3.98 | — | 4.43 | — | 4.6 | — | 4.98 | 14900 |
|  | Transparency | A |  | D |  | D |  | D |  | D |  |
| P25 | Concentration of NaOH (mM) | 1100 |  | 1150 |  | 1200 |  | 1250 |  | 1300 |  |
|  | C400P25Ca100Cl200 | 5.53 | — | 5.71 | — | 6.25 | — | 7.12 | — | 11.78 | 12 |
|  | Transparency | D |  | D |  | D |  | D |  | A |  |
|  | Concentration of NaOH (mM) | 500 |  | 550 |  | 600 |  | 650 |  | 700 |  |
|  | C200P25Ca100Cl200 | 5.08 | — | 5.26 | — | 5.88 | — | 6.72 | — | 11.84 | 39.8 |
|  | Transparency | D |  | D |  | D |  | D |  | A |  |
|  | Concentration of NaOH (mM) | 275 |  | 300 |  | 325 |  | 350 |  | 375 |  |
|  | C100P25Ca100Cl200 | 4.49 | — | 5.08 | — | 5.93 | — | 6.21 | — | 8.44 | — |
|  | Transparency | D |  | D |  | D |  | D |  | D |  |
|  | Concentration of NaOH (mM) | 125 |  | 150 |  | 175 |  | 200 |  | 225 |  |
|  | C50P25Ca100Cl200 | 3.36 | — | 3.55 | — | 4.47 | — | 4.97 | — | 7.33 | — |
|  | Transparency | D |  | D |  | D |  | D |  | D |  |
|  | Concentration of NaOH (mM) | 100 |  | 125 |  | 150 |  | 175 |  | 200 |  |
|  | C25P25Ca100Cl200 | 3.5 | — | 4.27 | — | 4.54 | — | 5.83 | 1340 | 11.46 | — |
|  | Transparency | D |  | D |  | D |  | D |  | D |  |
|  | Concentration of NaOH (mM) | 25 |  | 50 |  | 75 |  | 100 |  | 125 |  |
|  | C12.5P25Ca100Cl200 | 2.59 | — | 3.81 | — | 4.27 | — | 4.62 | — | 9.52 | 23000 |
|  | Transparency | A |  | D |  | D |  | D |  | D |  |

TABLE 2-1-continued

|  |  | | | | | | | | | |
|---|---|---|---|---|---|---|---|---|---|---|
|  | Concentration of NaOH (mM) | 0 |  | 25 |  | 50 |  | 75 |  | 100 |  |
|  | C0P25Ca100Cl200 | 1.83 | — | 3.68 | — | 4.15 | — | 4.64 | — | 10.82 | 32000 |
|  | Transparency | A |  | D |  | D |  | D |  | D |  |
| P12.5 | Concentration of NaOH (mM) | 1050 |  | 1100 |  | 1150 |  | 1200 |  | 1250 |  |
|  | C400P12.5Ca100Cl200 | 5.31 | — | 5.53 | — | 5.86 | — | 6.53 | — | 11.2 | — |
|  | Transparency | D |  | D |  | D |  | D |  | D |  |
|  | Concentration of NaOH (mM) | 450 |  | 500 |  | 550 |  | 600 |  | 650 |  |
|  | C200P12.5Ca100Cl200 | 4.67 | — | 5.19 | — | 5.43 | — | 6.52 | — | 11.9 | — |
|  | Transparency | D |  | D |  | D |  | D |  | D |  |
|  | Concentration of NaOH (mM) | 250 |  | 275 |  | 300 |  | 325 |  | 350 |  |
|  | C100P12.5Ca100Cl200 | 4.08 | — | 4.84 | — | 5.74 | — | 6.62 | — | 11.53 | — |
|  | Transparency | D |  | D |  | D |  | D |  | D |  |
|  | Concentration of NaOH (mM) | 100 |  | 125 |  | 150 |  | 175 |  | 200 |  |
|  | C50P12.5Ca100Cl200 | 3.3 | — | 3.48 | — | 3.85 | — | 5 | — | 11.1 | — |
|  | Transparency | D |  | D |  | D |  | D |  | D |  |
|  | Concentration of NaOH (mM) | 75 |  | 100 |  | 125 |  | 150 |  | 175 |  |
|  | C25P12.5Ca100Cl200 | 3.7 | — | 4.6 | — | 10.76 | — | 11.83 | — | 12.13 | — |
|  | Transparency | D |  | D |  | D |  | D |  | D |  |
|  | Concentration of NaOH (mM) | 25 |  | 50 |  | 75 |  | 100 |  | 125 |  |
|  | C12.5P12.5Ca100Cl200 | 3.19 | — | 4.3 | — | 5.26 | — | 11.5 | 31200 | 12.04 | 29600 |
|  | Transparency | A |  | D |  | D |  | D |  | D |  |
|  | Concentration of NaOH (mM) | 0 |  | 125 |  | 50 |  | 75 |  | 100 |  |
|  | C0P12.5Ca100Cl200 | 2.06 | — | 4.1 | — | 18.43 | 52200 | 11.83 | 48100 | 12.06 | 43500 |
|  | Transparency | A |  | C |  | C |  | C |  | C |  |
| P0 | Concentration of NaOH (mM) | 1000 |  | 1050 |  | 1100 |  | 1150 |  | 1200 |  |
|  | C400P0Ca100Cl200 | 5.25 | — | 5.35 | — | 5.6 | — | 8.86 | — | 11.13 | — |
|  | Transparency | D |  | D |  | D |  | D |  | D |  |
|  | Concentration of NaOH (mM) | 500 |  | 550 |  | 600 |  | 650 |  | 700 |  |
|  | C200P0Ca100Cl200 | 5.49 | — | 5.75 | — | 11.39 | — | 12.36 | — | 12.58 | — |
|  | Transparency | D |  | D |  | D |  | D |  | D |  |
|  | Concentration of NaOH (mM) | 250 |  | 275 |  | 300 |  | 325 |  | 350 |  |
|  | C100P0Ca100Cl200 | 4.5 | — | 5.4 | — | 10.82 | — | 12.05 | — | 12.09 | — |
|  | Transparency | D |  | D |  | D |  | D |  | D |  |
|  | Concentration of NaOH (mM) | 125 |  | 138 |  | 150 |  | 163 |  | 175 |  |
|  | C50P0Ca100Cl200 | 3.82 | — | 4.04 | — | 9.88 | — | 11.8 | — | 11.84 | — |
|  | Transparency | D |  | D |  | D |  | D |  | D |  |
|  | Concentration of NaOH (mM) | 63 |  | 69 |  | 75 |  | 81 |  | 88 |  |
|  | C25P0Ca100Cl200 | 3.83 | — | 4.03 | — | 8.2 | — | 11.16 | — | 11.49 | — |
|  | Transparency | D |  | D |  | D |  | D |  | D |  |
|  | Concentration of NaOH (mM) | 31 |  | 34 |  | 38 |  | 41 |  | 44 |  |
|  | C12.5P0Ca100Cl200 | 4.1 | — | 4.2 | — | 5.81 | — | 10.58 | — | 11.18 | — |
|  | Transparency | D |  | D |  | D |  | D |  | D |  |

|  |  |  | pH | Ca (μM) | pH | Ca (μM) | pH | Ca (μM) |
|---|---|---|---|---|---|---|---|---|
| P200 |  | Concentration of NaOH (mM) | 1800 |  | 1900 |  | 2000 |  |
|  |  | C400P200Ca100Cl200 | 11.8 | 0.29 | 12.75 | 0.43 | 13 | 1.03 |
|  |  | Transparency | D |  | D |  | D |  |
|  |  | Concentration of NaOH (mM) | 1100 |  | 1150 |  | 1200 |  |
|  |  | C200P200Ca100Cl200 | 10.64 | 0.18 | 11.24 | 0.18 | 12 | 0.2 |
|  |  | Transparency | D |  | D |  | D |  |
|  |  | Concentration of NaOH (mM) | 750 |  | 800 |  | 850 |  |
|  |  | C100P200Ca100Cl200 | 7.41 | 2098 | 10.68 | 0.16 | 11.38 | 0.14 |
|  |  | Transparency | D |  | D |  | D |  |
|  |  | Concentration of NaOH (mM) | 650 |  | 700 |  | 750 |  |
|  |  | C50P200Ca100Cl200 | 10.74 | 0.15 | 11.39 | 0.14 | 11.88 | 0.15 |
|  |  | Transparency | D |  | D |  | D |  |
|  |  | Concentration of NaOH (mM) | 600 |  | 650 |  | 700 |  |
|  |  | C25P200Ca100Cl200 | 11.12 | 0.14 | 11.65 | 0.14 | 12.09 | 0.17 |
|  |  | Transparency | D |  | D |  | D |  |
|  |  | Concentration of NaOH (mM) | 550 |  | 600 |  | 650 |  |
|  |  | C12.5P200Ca100Cl200 | 11.01 | 0.16 | 11.31 | 0.15 | 12.05 | 0.15 |
|  |  | Transparency | D |  | D |  | D |  |
|  |  | Concentration of NaOH (mM) | 500 |  | 550 |  | 600 |  |
|  |  | C0P200Ca100Cl200 | 10.45 | 10.21 | 11.35 | 0.14 | 11.86 | 0.14 |
|  |  | Transparency | D |  | D |  | D |  |
| P100 |  | Concentration of NaOH (mM) | 1500 |  | 1550 |  | 1600 |  |
|  |  | C400P100Ca100Cl200 | 11.13 | 0.26 | 12.27 | 0.29 | 12.64 | 0.47 |
|  |  | Transparency | D |  | D |  | E |  |
|  |  | Concentration of NaOH (mM) | 900 |  | 950 |  | 1000 |  |
|  |  | C200P100Ca100Cl200 | 11.29 | 0.08 | 12.31 | 0.09 | 12.64 | 0.13 |
|  |  | Transparency | D |  | D |  | D |  |
|  |  | Concentration of NaOH (mM) | 600 |  | 650 |  | 700 |  |
|  |  | C100P100Ca100Cl200 | 11.38 | 0.06 | 12.25 | 0.08 | 12.58 | 0.13 |
|  |  | Transparency | D |  | D |  | D |  |
|  |  | Concentration of NaOH (mM) | 450 |  | 500 |  | 550 |  |
|  |  | C50P100Ca100Cl200 | 11.29 | 0.07 | 12.22 | 0.08 | 12.59 | 0.13 |
|  |  | Transparency | D |  | D |  | D |  |
|  |  | Concentration of NaOH (mM) | 400 |  | 450 |  | 500 |  |

TABLE 2-1-continued

| | | | | | | | |
|---|---|---|---|---|---|---|---|
| | C25P100Ca100Cl200 | 12 | 0.07 | 12.53 | 0.12 | 12.74 | 0.18 |
| | Transparency | D | | D | | D | |
| | Concentration of NaOH (mM) | 300 | | 350 | | 400 | |
| | C12.5P100Ca100Cl200 | 7.47 | 5.87 | 11.7 | 0.08 | 12.35 | 0.08 |
| | Transparency | D | | D | | D | |
| | Concentration of NaOH (mM) | 250 | | 300 | | 350 | |
| | C0P100Ca100Cl200 | 6.66 | 30.4 | 11.5 | 0.1 | 12.29 | 0.09 |
| | Transparency | D | | D | | D | |
| P50 | Concentration of NaOH (mM) | 1450 | | 1500 | | 1550 | |
| | C400P50Ca100Cl200 | 12.6 | 0.61 | 12.79 | 0.92 | 12.88 | 1.3 |
| | Transparency | A | | A | | A | |
| | Concentration of NaOH (mM) | 800 | | 850 | | 900 | |
| | C200P50Ca100Cl200 | 11.83 | 3.31 | 12.39 | 1.16 | 12.62 | 0.94 |
| | Transparency | A | | A | | A | |
| | Concentration of NaOH (mM) | 450 | | 475 | | 500 | |
| | C100P50Ca100Cl200 | 6.7 | 108 | 9.66 | 17.9 | 11.8 | 4.5 |
| | Transparency | A | | A | | A | |
| | Concentration of NaOH (mM) | 300 | | 325 | | 350 | |
| | C50P50Ca100Cl200 | 6.48 | 313 | 8.23 | 65.4 | 11.86 | 8.16 |
| | Transparency | A | | A | | B | |
| | Concentration of NaOH (mM) | 275 | | 300 | | 325 | |
| | C25P50Ca100Cl200 | 11.88 | 12.8 | 12.24 | 6.22 | 12.43 | 5.11 |
| | Transparency | B | | B | | 1 B | |
| | Concentration of NaOH (mM) | 250 | | 275 | | 300 | |
| | C12.5P50Ca100Cl200 | 12.12 | 14.6 | 12.34 | 7.46 | 12.5 | 6.29 |
| | Transparency | D | | D | | D | |
| | Concentration of NaOH (mM) | 175 | | 200 | | 225 | |
| | C0P50Ca100Cl200 | 7.16 | 5800 | 11.5 | 673 | 12.18 | 98.2 |
| | Transparency | D | | D | | D | |
| P25 | Concentration of NaOH (mM) | 1350 | | 1400 | | 1450 | |
| | C400P25Ca100Cl200 | 12.47 | 13.4 | 12.7 | 25.3 | 12.85 | 36.8 |
| | Transparency | A | | A | | A | |
| | Concentration of NaOH (mM) | 750 | | 800 | | 850 | |
| | C200P25Ca100Cl200 | 12.52 | 51.3 | 12.76 | 73.2 | 12.88 | 92.3 |
| | Transparency | A | | A | | A | |
| | Concentration of NaOH (mM) | 400 | | 425 | | 450 | |
| | C100P25Ca100Cl200 | 11.73 | 211 | 12.22 | 229 | 12.44 | 271 |
| | Transparency | A | | A | | A | |
| | Concentration of NaOH (mM) | 250 | | 275 | | 300 | |
| | C50P25Ca100Cl200 | 11.67 | — | 12.16 | 12100 | 12.4 | 12900 |
| | Transparency | D | | D | | D | |
| | Concentration of NaOH (mM) | 225 | | 250 | | 275 | |
| | C25P25Ca100Cl200 | 12.07 | 75700 | 12.3 | 66200 | 12.48 | 57500 |
| | Transparency | D | | D | | D | |
| | Concentration of NaOH (mM) | 150 | | 175 | | 200 | |
| | C12.5P25Ca100Cl200 | 11.84 | 18600 | 12.22 | 18000 | 12.44 | 15900 |
| | Transparency | D | | D | | D | |
| | Concentration of NaOH (mM) | 125 | | 150 | | 175 | |
| | C0P25Ca100Cl200 | 12 | 30300 | 12.23 | 27400 | 12.31 | 20600 |
| | Transparency | D | | D | | D | |
| P12.5 | Concentration of NaOH (mM) | 1300 | | 1350 | | 1400 | |
| | C400P12.5Ca100Cl200 | 12.39 | — | 12.7 | — | 12.84 | 95.3 |
| | Transparency | D | | D | | A | |
| | Concentration of NaOH (mM) | 700 | | 750 | | 800 | |
| | C200P12.5Ca100Cl200 | 12.5 | — | 12.74 | 182 | 12.85 | 209 |
| | Transparency | D | | A | | A | |
| | Concentration of NaOH (mM) | 375 | | 400 | | 425 | |
| | C100P12.5Ca100Cl200 | 12.16 | — | 12.32 | — | 12.45 | 669 |
| | Transparency | D | | D | | A | |
| | Concentration of NaOH (mM) | 225 | | 250 | | 275 | |
| | C50P12.5Ca100Cl200 | 12.08 | — | 12.19 | — | 12.39 | — |
| | Transparency | D | | D | | D | |
| | Concentration of NaOH (mM) | 200 | | 225 | | 250 | |
| | C25P12.5Ca100Cl200 | 12.31 | — | 12.43 | — | 12.54 | — |
| | Transparency | D | | D | | D | |
| | Concentration of NaOH (mM) | 150 | | 175 | | 200 | |
| | C12.5P12.5Ca100Cl200 | 12.24 | 29100 | 12.38 | 26000 | 12.4 | 19600 |
| | Transparency | D | | D | | D | |
| | Concentration of NaOH (mM) | 125 | | 150 | | 175 | |
| | C0P12.5Ca100Cl200 | 12.12 | 32800 | 12.19 | 24600 | 12.25 | 19600 |
| | Transparency | C | | D | | D | |
| P0 | Concentration of NaOH (mM) | 1250 | | 1300 | | 1350 | |
| | C400P0Ca100Cl200 | 12.45 | — | 12.69 | — | 12.81 | — |
| | Transparency | D | | D | | D | |
| | Concentration of NaOH (mM) | 750 | | | | | |
| | C200P0Ca100Cl200 | 12.65 | — | | | | |
| | Transparency | D | | | | | |
| | Concentration of NaOH (mM) | 375 | | | | | |
| | C100P0Ca100Cl200 | 12.24 | — | | | | |
| | Transparency | D | | | | | |

TABLE 2-1-continued

| | | |
|---|---|---|
| Concentration of NaOH (mM) | 188 | |
| C50P0Ca100Cl200 | 11.85 | — |
| Transparency | D | |
| Concentration of NaOH (mM) | 94 | |
| C25P0Ca100Cl200 | 11.47 | — |
| Transparency | D | |
| Concentration of NaOH (mM) | 47 | |
| C12.5P0Ca100Cl200 | 11.36 | — |
| Transparency | D | |

TABLE 2-2

| | | Absorbance values | | | | | | | |
|---|---|---|---|---|---|---|---|---|---|
| P200 | Concentration of NaOH (mM) | 1300 | 1400 | 1500 | 1600 | 1700 | 1800 | 1900 | 2000 |
| | C400P200Ca100Cl200 | 1.732 | 1.660 | 1.345 | 0.445 | 0.432 | 0.665 | 0.905 | 0.860 |
| | Transparency | D | D | D | D | D | D | D | D |
| | Concentration of NaOH (mM) | 850 | 900 | 950 | 1000 | 1050 | 1100 | 1150 | 1200 |
| | C200P200Ca100Cl200 | 0.958 | 0.602 | 0.815 | 0.532 | 0.538 | 0.718 | 0.737 | 0.815 |
| | Transparency | D | D | D | D | D | D | D | D |
| | Concentration of NaOH (mM) | 500 | 550 | 600 | 650 | 700 | 750 | 800 | 850 |
| | C100P200Ca100Cl200 | 1.819 | 0.504 | 0.632 | 0.564 | 0.670 | 0.608 | 0.736 | 0.783 |
| | Transparency | D | D | D | D | D | D | D | D |
| | Concentration of NaOH (mM) | 400 | 450 | 500 | 550 | 600 | 650 | 700 | 750 |
| | C50P200Ca100Cl200 | 1.127 | 0.632 | 0.618 | 0.698 | 0.703 | 0.763 | 0.744 | 0.728 |
| | Transparency | D | D | D | D | D | D | D | D |
| | Concentration of NaOH (mM) | 350 | 400 | 450 | 500 | 550 | 600 | 650 | 700 |
| | C25P200Ca100Cl200 | 0.337 | 0.743 | 0.787 | 0.752 | 0.714 | 0.765 | 0.705 | 0.796 |
| | Transparency | D | D | D | D | D | D | D | D |
| | Concentration of NaOH (mM) | 300 | 350 | 400 | 450 | 500 | 550 | 600 | 650 |
| | C12.5P200Ca100Cl200 | 0.645 | 0.745 | 0.784 | 0.725 | 0.679 | 0.662 | 0.650 | 0.772 |
| | Transparency | D | D | D | D | D | D | D | D |
| | Concentration of NaOH (mM) | 250 | 300 | 350 | 400 | 450 | 500 | 550 | 600 |
| | C0P200Ca100Cl200 | 0.925 | 0.092 | 0.699 | 0.777 | 0.678 | 0.656 | 0.614 | 0.771 |
| | Transparency | D | D | D | D | D | D | D | D |
| P100 | Concentration of NaOH (mM) | 1250 | 1300 | 1350 | 1400 | 1450 | 1500 | 1550 | 1600 |
| | C400P100Ca100Cl200 | 1.802 | 1.636 | 1.637 | 0.065 | 0.028 | 0.472 | 0.566 | 0.583 |
| | Transparency | D | D | D | B | A | D | D | D |
| | Concentration of NaOH (mM) | 650 | 700 | 750 | 800 | 850 | 900 | 950 | 1000 |
| | C200P100Ca100Cl200 | 1.660 | 1.807 | 0.593 | 0.090 | 0.047 | 0.502 | 0.633 | 0.649 |
| | Transparency | D | D | B | B | A | D | D | D |
| | Concentration of NaOH (mM) | 350 | 400 | 450 | 500 | 550 | 600 | 650 | 700 |
| | C100P100Ca100Cl200 | 1.911 | 1.925 | 0.982 | 0.110 | 0.164 | 0.543 | 0.591 | 0.672 |
| | Transparency | D | D | D | B | C | D | D | D |
| | Concentration of NaOH (mM) | 200 | 250 | 300 | 350 | 400 | 450 | 500 | 550 |
| | C50P100Ca100Cl200 | 1.535 | 1.508 | 1.697 | 0.151 | 0.448 | 0.538 | 0.611 | 0.563 |
| | Transparency | D | D | D | C | D | D | D | D |
| | Concentration of NaOH (mM) | 150 | 200 | 250 | 300 | 350 | 400 | 450 | 500 |
| | C25P100Ca100Cl200 | 0.756 | 0.975 | 1.265 | 0.413 | 0.505 | 0.537 | 0.571 | 0.592 |
| | Transparency | D | D | D | D | D | D | D | D |
| | Concentration of NaOH (mM) | 50 | 100 | 150 | 200 | 250 | 300 | 350 | 400 |
| | C12.5P100Ca100Cl200 | −0.002 | 0.001 | 0.120 | 0.256 | 0.702 | 0.535 | 0.521 | 0.554 |
| | Transparency | A | A | D | D | D | D | D | D |
| | Concentration of NaOH (mM) | 0.0 | 50.0 | 100.0 | 150.0 | 200.0 | 250 | 300 | 350 |
| | C0P100Ca100Cl200 | −0.001 | 0.000 | 0.003 | 0.093 | 0.291 | 0.545 | 0.510 | 0.540 |
| | Transparency | A | A | D | D | D | D | D | D |
| P50 | Concentration of NaOH (mM) | 1200 | 1250 | 1300 | 1350 | 1400 | 1450 | 1500 | 1550 |
| | C400P50Ca100Cl200 | 1.767 | 1.791 | 0.055 | 0.017 | 0.019 | 0.022 | 0.030 | 0.031 |
| | Transparency | D | D | A | A | A | A | A | A |
| | Concentration of NaOH (mM) | 550 | 600 | 650 | 700 | 750 | 800 | 850 | 900 |
| | C200P50Ca100Cl200 | 1.887 | 1.872 | 1.632 | 1.590 | 0.008 | 0.011 | 0.016 | 0.022 |
| | Transparency | D | D | D | D | A | A | A | A |
| | Concentration of NaOH (mM) | 325 | 350 | 375 | 400 | 425 | 450 | 475 | 500 |
| | C100P50Ca100Cl200 | 1.928 | 1.899 | 1.908 | 0.391 | 0.010 | 0.003 | 0.012 | 0.025 |
| | Transparency | D | D | D | D | A | A | A | A |
| | Concentration of NaOH (mM) | 175 | 200 | 225 | 250 | 275 | 300 | 325 | 350 |
| | C50P50Ca100Cl200 | 1.343 | 0.913 | 1.340 | 1.563 | 0.139 | 0.007 | 0.033 | 0.053 |
| | Transparency | D | D | D | D | D | A | A | B |
| | Concentration of NaOH (mM) | 150 | 175 | 200 | 225 | 250 | 275 | 300 | 325 |
| | C25P50Ca100Cl200 | 1.355 | 0.648 | 0.388 | 0.111 | 0.080 | 0.137 | 0.192 | 0.269 |
| | Transparency | D | D | D | D | A | B | B | B |
| | Concentration of NaOH (mM) | 125 | 150 | 175 | 200 | 225 | 250 | 275 | 300 |
| | C12.5P50Ca100Cl200 | 0.557 | 0.233 | 0.309 | 0.523 | 0.432 | 0.438 | 0.459 | 0.492 |
| | Transparency | D | D | D | D | D | D | D | D |
| | Concentration of NaOH (mM) | 50 | 75 | 100 | 125 | 150 | 175 | 200 | 225 |

TABLE 2-2-continued

| | | Absorbance values | | | | | | | |
|---|---|---|---|---|---|---|---|---|---|
| | C0P50Ca100Cl200 | −0.006 | 0.007 | 0.081 | 0.259 | 0.303 | 0.306 | 0.605 | 0.578 |
| | Transparency | A | D | D | D | D | D | D | D |
| P25 | Concentration of NaOH (mM) | 1100 | 1150 | 1200 | 1250 | 1300 | 1350 | 1400 | 1450 |
| | C400P25Ca100Cl200 | 1.806 | 1.839 | 1.788 | 1.357 | 0.011 | 0.012 | 0.016 | 0.023 |
| | Transparency | D | D | D | D | A | A | A | A |
| | Concentration of NaOH (mM) | 500 | 550 | 600 | 650 | 700 | 750 | 800 | 850 |
| | C200P25Ca100Cl200 | 1.768 | 1.958 | 1.604 | 1.692 | 0.059 | 0.120 | 0.247 | 0.337 |
| | Transparency | D | D | D | D | A | A | A | A |
| | Concentration of NaOH (mM) | 275 | 300 | 325 | 350 | 375 | 400 | 425 | 450 |
| | C100P25Ca100Cl200 | 1.890 | 1.875 | 1.926 | 1.102 | 0.511 | 0.019 | 0.123 | 0.524 |
| | Transparency | D | D | D | D | D | A | A | A |
| | Concentration of NaOH (mM) | 125 | 150 | 175 | 200 | 225 | 250 | 275 | 300 |
| | C50P25Ca100Cl200 | 1.495 | 1.162 | 1.091 | 1.703 | 1.246 | 0.594 | 0.380 | 0.601 |
| | Transparency | D | D | D | D | D | D | D | D |
| | Concentration of NaOH (mM) | 100 | 125 | 150 | 175 | 200 | 225 | 250 | 275 |
| | C25P25Ca100Cl200 | 0.664 | 0.921 | 0.859 | 0.866 | 0.764 | 1.172 | 0.869 | 0.770 |
| | Transparency | D | D | D | D | D | D | D | D |
| | Concentration of NaOH (mM) | 25 | 50 | 75 | 100 | 125 | 150 | 175 | 200 |
| | C12.5P25Ca100Cl200 | 0.005 | 0.243 | 1.282 | 0.498 | 0.467 | 0.482 | 0.547 | 0.587 |
| | Transparency | A | D | D | D | D | D | D | D |
| | Concentration of NaOH (mM) | 0 | 25 | 50 | 75 | 100 | 125 | 150 | 175 |
| | C0P25Ca100Cl200 | 0.004 | 0.009 | 0.094 | 0.154 | 0.254 | 0.267 | 0.295 | 0.401 |
| | Transparency | A | D | D | D | D | D | D | D |
| P12.5 | Concentration of NaOH (mM) | 1050 | 1100 | 1150 | 1200 | 1250 | 1300 | 1350 | 1400 |
| | C400P12.5Ca100Cl200 | 1.741 | 1.711 | 1.718 | 1.640 | 0.100 | 0.027 | 0.020 | 0.015 |
| | Transparency | D | D | D | D | D | D | D | A |
| | Concentration of NaOH (mM) | 450 | 500 | 550 | 600 | 650 | 700 | 750 | 800 |
| | C200P12.5Ca100Cl200 | 1.728 | 1.911 | 1.837 | 1.579 | 1.433 | 1.256 | 0.010 | 0.007 |
| | Transparency | D | D | D | D | D | D | A | A |
| | Concentration of NaOH (mM) | 250 | 275 | 300 | 325 | 350 | 375 | 400 | 425 |
| | C100P12.5Ca100Cl200 | 1.679 | 1.777 | 1.895 | 1.303 | 0.916 | 1.375 | 0.075 | 0.140 |
| | Transparency | D | D | D | D | D | D | D | A |
| | Concentration of NaOH (mM) | 100 | 125 | 150 | 175 | 200 | 225 | 250 | 275 |
| | C50P12.5Ca100Cl200 | 0.797 | 1.100 | 0.457 | 1.406 | 1.571 | 0.963 | 1.030 | 1.158 |
| | Transparency | D | D | D | D | D | D | C | D |
| | Concentration of NaOH (mM) | 75 | 100 | 125 | 150 | 175 | 200 | 225 | 250 |
| | C25P12.5Ca100Cl200 | 1.027 | 0.799 | 0.735 | 0.663 | 0.926 | 0.949 | 1.231 | 1.176 |
| | Transparency | D | D | D | D | D | D | D | D |
| | Concentration of NaOH (mM) | 25 | 50 | 75 | 100 | 125 | 150 | 175 | 200 |
| | C12.5P12.5Ca100Cl200 | 0.000 | 0.610 | 0.332 | 0.250 | 0.476 | 0.588 | 0.645 | 0.594 |
| | Transparency | A | D | D | D | 1D | D | D | D |
| | Concentration of NaOH (mM) | 0 | 25 | 50 | 75 | 100 | 125 | 150 | 175 |
| | C0P12.5Ca100Cl200 | 0.000 | 0.047 | 0.135 | 0.123 | 0.138 | 0.187 | 0.451 | 0.478 |
| | Transparency | A | C | C | C | C | C | D | D |
| P0 | Concentration of NaOH (mM) | 1000 | 1050 | 1100 | 1150 | 1200 | 1250 | 1300 | 1350 |
| | C400P0Ca100Cl200 | 1.808 | 1.766 | 1.79 | 1.826 | 1.786 | 1.814 | 1.773 | 1.697 |
| | Transparency | D | D | D | D | D | D | D | D |
| | Concentration of NaOH (mM) | 500 | 550 | 600 | 650 | 700 | 750 | | |
| | C200P0Ca100Cl200 | 1.955 | 1.67 | 1.635 | 1.405 | 0.343 | 0.528 | | |
| | Transparency | D | D | D | D | D | D | | |
| | Concentration of NaOH (mM) | 250 | 275 | 300 | 325 | 350 | 375 | | |
| | C100P0Ca100Cl200 | 1.715 | 1.91 | 1.841 | 1.562 | 1.422 | 1.242 | | |
| | Transparency | D | D | D | D | D | D | | |
| | Concentration of NaOH (mM) | 125 | 138 | 150 | 163 | 175 | 188 | | |
| | C50P0Ca100Cl200 | 1.398 | 0.699 | 0.734 | 0.719 | 1.192 | 1.539 | | |
| | Transparency | D | D | D | D | D | D | | |
| | Concentration of NaOH (mM) | 63 | 69 | 75 | 81 | 88 | 94 | | |
| | C25P0Ca100Cl200 | 1.179 | 0.228 | 0.766 | 0.054 | 0.542 | 0.881 | | |
| | Transparency | D | D | D | D | D | D | | |
| | Concentration of NaOH (mM) | 31 | 34 | 38 | 41 | 44 | 47 | | |
| | C12.5P0Ca100Cl200 | 0.577 | 0.181 | 0.43 | 0.816 | 0.71 | −0.02 | | |
| | Transparency | D | D | D | D | D | D | | |

When the concentration of citric acid was in the range of 25 mM to 400 mM, the aqueous preparation of calcium of the present invention was obtained. When the concentration of phosphoric acid was in a range of 12.5 to 200 mM, the aqueous preparation of calcium of the present invention was obtained. When the concentration of phosphoric acid was 50 mM, the solubilization range was the widest. The pH range in which the aqueous preparation of calcium of the present invention was obtained was from 5.67 to 12.88. That is, the aqueous preparation of calcium of the present invention is obtained under the conditions where the concentration of citric acid is from 25 mM to 400 mM, the concentration of phosphoric acid is from 12.5 mM to 200 mM, and the pH range is from 5.67 to 12.88.

The results when the concentration of calcium was fixed to 200 mM, citric acid was modified at a concentration of 0 to 400 mM, and phosphoric acid was modified at a concentration of 50 to 200 mM are shown in Table 3.

TABLE 3-1

| | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|
| Concentration of NaOH (mM) | 1450 | | 1500 | | 1550 | | 1600 | | 1650 | | 1700 | |
| C400P200Ca200Cl400 | 6.08 | — | 6.16 | — | 6.28 | — | 6.46 | 23 | 6.8 | 10.5 | 8.06 | 0.48 |
| Transparency | D | | D | | D | | C | | C | | C | |
| Concentration of NaOH (mM) | 800 | | 850 | | 900 | | 950 | | 1000 | | 1050 | |
| C200P200Ca200Cl400 | 5.43 | — | 5.48 | — | 5.49 | — | 5.65 | — | 5.83 | 168 | 6.17 | 88.1 |
| Transparency | D | | D | | D | | D | | C | | C | |
| Concentration of NaOH (mM) | 400 | | 425 | | 450 | | 475 | | 500 | | 525 | |
| C100P200Ca200Cl400 | 3.77 | — | 4.61 | — | 5.3 | — | 5.45 | — | 5.57 | — | 6.06 | — |
| Transparency | D | | D | | D | | D | | D | | D | |
| Concentration of NaOH (mM) | 400 | | 450 | | 500 | | 550 | | 600 | | 650 | |
| C50P200Ca200Cl400 | 3.64 | — | 4.17 | — | 5.02 | — | 5.15 | — | 5.84 | — | 6.6 | — |
| Transparency | D | | D | | D | | D | | D | | D | |
| Concentration of NaOH (mM) | 250 | | 300 | | 350 | | 1400 | | 450 | | 500 | |
| C0P200Ca200Cl400 | 3.19 | — | 3.08 | — | 4.24 | — | 5.1 | 6930 | 5.49 | 1520 | 6.6 | 60.3 |
| Transparency | D | | D | | D | | D | | D | | D | |

| | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 1750 | | 1800 | | 1850 | | 1900 | | | |
| C400P200Ca200Cl400 | 10.92 | 0.15 | 11.96 | 0.14 | 12.62 | 0.17 | 12.85 | 0.21 | | |
| Transparency | D | | D | | D | | D | | | |
| Concentration of NaOH (mM) | 1100 | | 1150 | | 1200 | | 1250 | | 1300 | |
| C200P200Ca200Cl400 | 6.7 | 35.8 | 8.63 | — | 11.21 | — | 11.73 | — | 12.83 | — |
| Transparency | C | | D | | D | | D | | D | |
| Concentration of NaOH (mM) | 550 | | 575 | | 600 | | | | | |
| C100P200Ca200Cl400 | 6.62 | — | 8.74 | — | 11.47 | — | | | | |
| Transparency | D | | D | | D | | | | | |
| Concentration of NaOH (mM) | 700 | | 750 | | 800 | | | | | |
| C50P200Ca200Cl400 | 9.96 | — | 11.59 | — | 12.41 | — | | | | |
| Transparency | D | | D | | D | | | | | |
| Concentration of NaOH (mM) | 550 | | 600 | | 650 | | 700 | | | |
| C0P200Ca200Cl400 | 10.31 | 0.17 | 11.58 | 0.07 | 12.32 | 0.08 | 12.64 | 0.12 | | |
| Transparency | D | | D | | D | | D | | | |

| | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|
| Concentration of NaOH (mM) | 1100 | | 1150 | | 1200 | | 1250 | | 1300 | | 1350 | |
| C400P100Ca200Cl400 | 5.26 | — | 5.29 | — | 5.43 | — | 5.82 | — | 6.29 | — | 6.38 | — |
| Transparency | D | | D | | D | | D | | D | | D | |
| Concentration of NaOH (mM) | 650 | | 700 | | 750 | | 800 | | 850 | | 900 | |
| C200P100Ca200Cl400 | 5.02 | — | 5.59 | — | 5.67 | — | 5.78 | — | 6.06 | — | 6.91 | 158 |
| Transparency | D | | D | | D | | D | | D | | B | |
| Concentration of NaOH (mM) | 350 | | 400 | | 450 | | 500 | | 550 | | 600 | |
| C100P100Ca200Cl400 | 3.44 | — | 3.89 | — | 4.89 | — | 5.43 | — | 5.83 | — | 6.59 | 267 |
| Transparency | D | | D | | D | | D | | D | | A | |
| Concentration of NaOH (mM) | 250 | | 300 | | 350 | | 400 | | 450 | | 500 | |
| C50P100Ca200Cl400 | 3.53 | — | 3.88 | — | 4.55 | — | 5.01 | — | 6.3 | 1230 | 11.74 | — |
| Transparency | D | | D | | D | | D | | A | | B | |
| Concentration of NaOH (mM) | 50 | | 100 | | 150 | | 200 | | 250 | | 300 | |
| C0P100Ca200Cl400 | 1.79 | — | 3.14 | — | 3.59 | — | 4.55 | — | 4.58 | 64200 | 5.3 | 36700 |
| Transparency | A | | D | | D | | D | | D | | D | |

| | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 1400 | | 1450 | | 1500 | | 1550 | | | |
| C400P100Ca200Cl400 | 6.67 | — | 7.24 | 26.8 | 11.56 | 2.4 | 12.36 | 0.71 | | |
| Transparency | D | | B | | A | | A | | | |
| Concentration of NaOH (mM) | 950 | | 1000 | | | | | | | |
| C200P100Ca200Cl400 | 11.84 | — | 12.66 | — | | | | | | |
| Transparency | B | | B | | | | | | | |
| Concentration of NaOH (mM) | 650 | | 700 | | | | | | | |
| C100P100Ca200Cl400 | 11.12 | — | 12.69 | — | | | | | | |
| Transparency | B | | B | | | | | | | |
| Concentration of NaOH (mM) | | | | | | | | | | |
| C50P100Ca200Cl400 | | | | | | | | | | |
| Transparency | | | | | | | | | | |
| Concentration of NaOH (mM) | 350 | | 400 | | 450 | | 500 | | | |
| C0P100Ca200Cl400 | 9.92 | 13600 | 12.17 | 1090 | 12.64 | 114 | 12.87 | 62 | | |
| Transparency | D | | D | | D | | D | | | |

TABLE 3-1-continued

|  | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|
| Concentration of NaOH (mM) | 1000 |  | 1050 |  | 1100 |  | 1150 |  | 1200 |  | 1250 |  |
| C400P50Ca200Cl400 | 5.05 | — | 5.3 | — | 5.29 | — | 5.47 | — | 5.94 | — | 6.68 | — |
| Transparency | D |  | D |  | D |  | D |  | D |  | D |  |
| Concentration of NaOH (mM) | 550 |  | 600 |  | 650 |  | 700 |  | 750 |  | 800 |  |
| C200P50Ca200Cl400 | 4.37 | — | 5 | — | 5.92 | — | 6.19 | — | 7.4 | — | 12.3 | — |
| Transparency | D |  | D |  | D |  | D |  | D |  | D |  |
| Concentration of NaOH (mM) | 300 |  | 350 |  | 400 |  | 450 |  | 500 |  |  |  |
| C100P50Ca200Cl400 | 3.38 | — | 4.26 | — | 5.06 | — | 6.92 | — | 12.18 | — |  |  |
| Transparency | D |  | D |  | D |  | D |  | D |  |  |  |
| Concentration of NaOH (mM) | 150 |  | 200 |  | 250 |  | 300 |  | 350 |  |  |  |
| C50P50Ca200Cl400 | 3.22 | — | 3.77 | — | 4.47 | — | 5.96 | — | 11.94 | — |  |  |
| Transparency | D |  | D |  | D |  | D |  | D |  |  |  |
| Concentration of NaOH (mM) | 50 |  | 100 |  | 150 |  | 200 |  | 250 |  | 300 |  |
| C0P50Ca200Cl400 | 3.45 | — | 4.17 | — | 4.83 | 130000 | 11.21 | 87700 | 12.13 | 70600 | 12.27 | 51100 |
| Transparency | D |  | D |  | C |  | D |  | D |  | D |  |

|  | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 1300 |  | 1350 |  | 1400 |  | 1401 |  |  |  |
| C400P50Ca200Cl400 | 7.22 | — | 11.57 | — | 12.41 | — | 12.73 | — |  |  |
| Transparency | D |  | D |  | D |  | D |  |  |  |
| Concentration of NaOH (mM) |  |  |  |  |  |  |  |  |  |  |
| C200P50Ca200Cl400 |  |  |  |  |  |  |  |  |  |  |
| Transparency |  |  |  |  |  |  |  |  |  |  |
| Concentration of NaOH (mM) |  |  |  |  |  |  |  |  |  |  |
| C100P50Ca200Cl400 |  |  |  |  |  |  |  |  |  |  |
| Transparency |  |  |  |  |  |  |  |  |  |  |
| Concentration of NaOH (mM) |  |  |  |  |  |  |  |  |  |  |
| C50P50Ca200Cl400 |  |  |  |  |  |  |  |  |  |  |
| Transparency |  |  |  |  |  |  |  |  |  |  |
| Concentration of NaOH (mM) | 350 |  | 400 |  |  |  |  |  |  |  |
| C0P50Ca200Cl400 | 12.37 | 33900 | 12.54 | 20000 |  |  |  |  |  |  |
| Transparency | D |  | D |  |  |  |  |  |  |  |

TABLE 3-2

| | Absorbance values | | | | | |
|---|---|---|---|---|---|---|
| Concentration of NaOH (mM) | 1450 | 1500 | 1550 | 1600 | 1650 | 1700 |
| C400P200Ca200Cl400 | 2.133 | 2.028 | 1.353 | 0.141 | 0.128 | 0.114 |
| Transparency | D | D | D | C | C | C |
| Concentration of NaOH (mM) | 800 | 850 | 900 | 950 | 1000 | 1050 |
| C200P200Ca200Cl400 | 2.030 | 2.150 | 1.980 | 1.690 | 0.250 | 0.210 |
| Transparency | D | D | D | D | C | C |
| Concentration of NaOH (mM) | 500 | 550 | 600 | 650 | 700 | 750 |
| C100P200Ca200Cl400 | 1.670 | 1.880 | 1.970 | 0.990 | 0.500 | 0.360 |
| Transparency | D | D | D | D | D | D |
| Concentration of NaOH (mM) | 400 | 450 | 500 | 550 | 600 | 650 |
| C50P200Ca200Cl400 | 1.576 | 1.565 | 1.474 | 0.882 | 0.767 | 0.976 |
| Transparency | D | D | D | D | D | D |
| Concentration of NaOH (mM) | 250 | 300 | 350 | 400 | 450 | 500 |
| C0P200Ca200Cl400 | 0.694 | 1.551 | 1.515 | 0.972 | 1.097 | 1.189 |
| Transparency | D | D | D | D | D | D |
| Concentration of NaOH (mM) | 1100 | 1150 | 1200 | 1250 | 1300 | 1350 |
| C400P100Ca200Cl400 | 2.272 | 2.141 | 2.129 | 2.141 | 2.124 | 2.116 |
| Transparency | D | D | D | D | D | D |
| Concentration of NaOH (mM) | 650 | 700 | 750 | 800 | 850 | 900 |
| C200P100Ca200Cl400 | 2.067 | 2.133 | 2.054 | 2 | 1.758 | 0.038 |
| Transparency | D | D | D | D | D | B |
| Concentration of NaOH (mM) | 350 | 400 | 450 | 500 | 550 | 600 |
| C100P100Ca200Cl400 | 1.248 | 1.547 | 1.872 | 2.047 | 0.26 | 0.044 |
| Transparency | D | D | D | D | A | B |
| Concentration of NaOH (mM) | 250 | 300 | 350 | 400 | 450 | 500 |
| C50P100Ca200Cl400 | 0.678 | 0.865 | 1.73 | 1.095 | 0.064 | 0.118 |
| Transparency | D | D | D | D | A | B |
| Concentration of NaOH (mM) | 50 | 100 | 150 | 200 | 250 | 300 |
| C0P100Ca200Cl400 | 0.043 | 0.059 | 0.243 | 0.218 | 0.772 | 0.878 |
| Transparency | A | D | D | D | D | D |
| Concentration of NaOH (mM) | 1000 | 1050 | 1100 | 1150 | 1200 | 1250 |
| C400P50Ca200Cl400 | 2.342 | 2.284 | 2.222 | 2.182 | 2.212 | 2.192 |
| Transparency | D | D | D | D | D | D |
| Concentration of NaOH (mM) | 550 | 600 | 650 | 700 | 750 | 800 |
| C200P50Ca200Cl400 | 1.683 | 2.056 | 2.157 | 2.114 | 2.016 | 1.923 |

TABLE 3-2-continued

| | | | | | | |
|---|---|---|---|---|---|---|
| Transparency | D | D | D | D | D | D |
| Concentration of NaOH (mM) | 300 | 350 | 400 | 450 | 500 | |
| C100P50Ca200Cl400 | 1.067 | 1.379 | 1.743 | 1.877 | 1.512 | |
| Transparency | D | D | D | D | D | |
| Concentration of NaOH (mM) | 150 | 200 | 250 | 300 | 350 | |
| C50P50Ca200Cl400 | 1.238 | 0.554 | 0.766 | 1.024 | 0.95 | |
| Transparency | D | D | D | D | D | |
| Concentration of NaOH (mM) | 50 | 100 | 150 | 200 | 250 | 300 |
| C0P50Ca200Cl400 | 0.053 | 0.164 | 0.457 | 0.52 | 0.881 | 1.228 |
| Transparency | D | D | C | D | D | D |

| | Absorbance values | | | | |
|---|---|---|---|---|---|
| Concentration of NaOH (mM) | 1750 | 1800 | 1850 | 1900 | |
| C400P200Ca200Cl400 | 0.855 | 0.972 | 1.097 | | |
| Transparency | D | D | D | D | |
| Concentration of NaOH (mM) | 1100 | 1150 | 1200 | 1250 | 1300 |
| C200P200Ca200Cl400 | 0.170 | 0.770 | 0.900 | 0.920 | 1.11 |
| Transparency | C | D | D | D | D |
| Concentration of NaOH (mM) | 800 | 850 | 900 | | |
| C100P200Ca200Cl400 | 0.740 | 0.890 | 0.940 | | |
| Transparency | D | D | D | | |
| Concentration of NaOH (mM) | 700 | 750 | 800 | | |
| C50P200Ca200Cl400 | 0.927 | 0.971 | 0.974 | | |
| Transparency | D | D | D | | |
| Concentration of NaOH (mM) | 550 | 600 | 650 | 700 | |
| C0P200Ca200Cl400 | 1.017 | 1.174 | 1272 | 1.348 | |
| Transparency | D | D | D | D | |
| Concentration of NaOH (mM) | 1400 | 1450 | 1500 | 1550 | |
| C400P100Ca200Cl400 | 1.932 | 0.068 | 0.016 | 0.020 | |
| Transparency | D | B | A | A | |
| Concentration of NaOH (mM) | 950 | 1000 | | | |
| C200P100Ca200Cl400 | 0.037 | 0.049 | | | |
| Transparency | B | B | | | |
| Concentration of NaOH (mM) | 650 | 700 | | | |
| C100P100Ca200Cl400 | 0.071 | 0.071 | | | |
| Transparency | B | B | | | |
| Concentration of NaOH (mM) | | | | | |
| C50P100Ca200Cl400 | | | | | |
| Transparency | | | | | |
| Concentration of NaOH (mM) | 350 | 400 | 450 | 500 | |
| C0P100Ca200Cl400 | 0.983 | 1.266 | 1.288 | 1.333 | |
| Transparency | D | D | D | D | |
| Concentration of NaOH (mM) | 1300 | 1350 | 1400 | 1450 | |
| C400P50Ca200Cl400 | 2.088 | 1.836 | 1.702 | 1.294 | |
| Transparency | D | D | D | D | |
| Concentration of NaOH (mM) | | | | | |
| C200P50Ca200Cl400 | | | | | |
| Transparency | | | | | |
| Concentration of NaOH (mM) | | | | | |
| C100P50Ca200Cl400 | | | | | |
| Transparency | | | | | |
| Concentration of NaOH (mM) | | | | | |
| C50P50Ca200Cl400 | | | | | |
| Transparency | | | | | |
| Concentration of NaOH (mM) | 350 | 400 | | | |
| C0P50Ca200Cl400 | 1.228 | 1.604 | | | |
| Transparency | D | D | | | |

When the concentration of citric acid was from 200 to 400 mM based on 200 mM of phosphoric acid and the concentration of citric acid was from 50 to 400 mM based on 100 mM of phosphoric acid, the aqueous preparation of calcium of the present invention was obtained. The pH range in which the aqueous preparation of calcium of the present invention was obtained was from 5.83 to 12.69.

The results when the concentration of calcium was fixed to 400 mM, citric acid was modified at a concentration of 100 to 800 mM, and phosphoric acid was modified at a concentration of 100 to 400 mM are shown in Table 4.

TABLE 4-1

| | pH | Ca (µM) | pH | Ca (µM) | pH | Ca (µM) | pH | Ca (µM) | pH | Ca (µM) |
|---|---|---|---|---|---|---|---|---|---|---|
| Concentration of NaOH (mM) | 2600 | | 2800 | | 3000 | | 3200 | | 3400 | |
| C800P400Ca400Cl800 | 4.92 | 99.4 | 5.62 | 54.3 | 6.17 | 48 | 6.35 | 30.1 | 7.22 | 7.26 |
| Transparency | D | | D | | D | | D | | B | |
| Concentration of NaOH (mM) | 1400 | | 1600 | | 1800 | | 2000 | | 2200 | |

TABLE 4-1-continued

| Sample | pH | Ca (μM) | pH | Ca (μM) | pH | Ca (μM) | pH | Ca (μM) | pH | Ca (μM) |
|---|---|---|---|---|---|---|---|---|---|---|
| C400P400Ca400Cl800 | 3.67 | 33200 | 4.97 | 388 | 5.49 | 245 | 5.83 | 100 | 6.7 | 21.7 |
| Transparency | D | | D | | D | | D | | D | |
| Concentration of NaOH (mM) | 800 | | 1000 | | 1200 | | 1400 | | 1600 | |
| C200P400Ca400Cl800 | 2.59 | 47000 | 3.08 | 28900 | 4.89 | 931 | 5.35 | 424 | 6.35 | 48.1 |
| Transparency | D | | D | | D | | D | | D | |
| Concentration of NaOH (mM) | 600 | | 800 | | 1000 | | 1200 | | 1400 | |
| C100P400Ca400Cl800 | 2.32 | 69600 | 2.92 | 44500 | 4.8 | 2740 | 5.45 | 447 | 8.48 | 2.01 |
| Transparency | D | | D | | D | | D | | D | |
| Concentration of NaOH (mM) | 2200 | | 2400 | | 2600 | | 2800 | | 3000 | |
| C800P200Ca400Cl800 | 4.83 | 135 | 5 | 89.6 | 6 | 44.4 | 6.61 | 36.7 | 10.33 | 23.6 |
| Transparency | D | | D | | D | | D | | A | |
| Concentration of NaOH (mM) | 1300 | | 1400 | | 1500 | | 1600 | | 1700 | |
| C400P200Ca400Cl800 | 5.09 | 1420 | 4.92 | 1670 | 5.36 | 566 | 5.71 | 227 | 6.11 | 128 |
| Transparency | D | | D | | D | | D | | D | |
| Concentration of NaOH (mM) | 700 | | 800 | | 900 | | 1000 | | 1100 | |
| C200P200Ca400Cl800 | 2.92 | 86000 | 3.21 | 46000 | 4.15 | 9800 | 5.28 | 1840 | 5.33 | 1590 |
| Transparency | D | | D | | D | | D | | D | |
| Concentration of NaOH (mM) | 600 | | 700 | | 800 | | 900 | | 1000 | |
| C100P200Ca400Cl800 | 3.34 | 138000 | 4.84 | 56900 | 4.54 | 25400 | 6.46 | 7090 | 11.53 | 250 |
| Transparency | D | | D | | D | | D | | B | |
| Concentration of NaOH (mM) | 2000 | | 2200 | | 2400 | | 2600 | | 2800 | |
| C800P100Ca400Cl800 | 4.7 | 112 | 4.81 | 83.2 | 5.52 | 55.9 | 6.8 | 41.6 | 12.59 | 25.4 |
| Transparency | D | | D | | D | | D | | D | |
| Concentration of NaOH (mM) | 1100 | | 1200 | | 1300 | | 1400 | | 1500 | |
| C400P100Ca400Cl800 | 4.35 | 7250 | 5.22 | 1300 | 5.28 | 1390 | 5.71 | 422 | 7.1 | 209 |
| Transparency | D | | D | | D | | D | | D | |
| Concentration of NaOH (mM) | 500 | | 600 | | 700 | | 800 | | 900 | |
| C200P100Ca400Cl800 | 2.64 | 99800 | 2.87 | 82100 | 3.4 | 64700 | 4.46 | 25100 | 7.34 | 24400 |
| Transparency | D | | D | | D | | D | | D | |
| Concentration of NaOH (mM) | 400 | | 500 | | 600 | | 700 | | 800 | |
| C100P100Ca400Cl800 | 3.16 | 195000 | 4.01 | 143000 | 5.88 | 93600 | 11.49 | 46700 | 12.18 | 24800 |
| Transparency | D | | D | | D | | D | | D | |

| | pH | Ca (μM) | pH | Ca (μM) | pH | Ca (μM) |
|---|---|---|---|---|---|---|
| Concentration of NaOH (mM) | 3600 | | 3800 | | 4000 | |
| C800P400Ca400Cl800 | 11.19 | 2.15 | 12.84 | 3.15 | 13.07 | 5.39 |
| Transparency | D | | D | | D | |
| Concentration of NaOH (mM) | 2400 | | 2600 | | 2800 | |
| C400P400Ca400Cl800 | 11.26 | 1.43 | 12.72 | 2.21 | 12.99 | 3.66 |
| Transparency | D | | D | | D | |
| Concentration of NaOH (mM) | 1800 | | 2000 | | 2200 | |
| C200P400Ca400Cl800 | 11.94 | 1.19 | 12.56 | 1.57 | 12.92 | 3.02 |
| Transparency | D | | D | | D | |
| Concentration of NaOH (mM) | 1600 | | 1800 | | 2000 | |
| C100P400Ca400Cl800 | 12.15 | 1.28 | 12.78 | 2.14 | 13.05 | 4.5 |
| Transparency | D | | D | | D | |
| Concentration of NaOH (mM) | 3200 | | 3400 | | 3600 | |
| C800P200Ca400Cl800 | 12.78 | 3.52 | 13.06 | 5.22 | 13.18 | 8.3 |
| Transparency | A | | A | | D | |
| Concentration of NaOH (mM) | 1800 | | 1900 | | 2000 | |
| C400P200Ca400Cl800 | 7.14 | 91.7 | 11.6 | 28.9 | 12.48 | 11.4 |
| Transparency | D | | A | | A | |
| Concentration of NaOH (mM) | 1200 | | 1300 | | 1400 | |
| C200P200Ca400Cl800 | 6.62 | 473 | 11.53 | 76.5 | 12.46 | 23 |
| Transparency | D | | A | | A | |
| Concentration of NaOH (mM) | 1100 | | 1200 | | 1300 | |
| C100P200Ca400Cl800 | 12.51 | 50.4 | 12.82 | 26.8 | 12.98 | 21.5 |
| Transparency | B | | B | | B | |
| Concentration of NaOH (mM) | 3000 | | 3200 | | 3400 | |
| C800P100Ca400Cl800 | 13.12 | 41.2 | 13.23 | 83 | 13.37 | 80.8 |
| Transparency | D | | A | | A | |
| Concentration of NaOH (mM) | 1600 | | 1700 | | 1800 | |
| C400P100Ca400Cl800 | 12.19 | 117 | 12.7 | 129 | 12.93 | 168 |
| Transparency | D | | D | | D | |
| Concentration of NaOH (mM) | 1000 | | 1100 | | 1200 | |
| C200P100Ca400Cl800 | 12.05 | 1020 | 12.36 | 1800 | 12.6 | 1400 |
| Transparency | D | | D | | D | |
| Concentration of NaOH (mM) | 900 | | 1000 | | 1100 | |
| C100P100Ca400Cl800 | 12.54 | 11800 | 12.74 | 16350 | 12.87 | 3800 |
| Transparency | D | | D | | D | |

TABLE 4-2

| | Absorbance values | | | | | | | |
|---|---|---|---|---|---|---|---|---|
| Concentration of NaOH (mM) | 2000 | 2200 | 2400 | 2600 | 2800 | 3000 | 3200 | 3400 |
| C800P400Ca400Cl800 | 2.264 | 2.423 | 2.391 | 2.215 | 0.063 | 0.833 | 1.200 | 1.353 |
| Transparency | D | D | D | D | B | D | D | D |
| Concentration of NaOH (mM) | 1100 | 1200 | 1300 | 1400 | 1500 | 1600 | 1700 | 1800 |
| C400P400Ca400Cl800 | 1.562 | 2.399 | 2.064 | 2.086 | 0.234 | 1.519 | 1.640 | 1.720 |
| Transparency | D | D | D | D | D | D | D | D |
| Concentration of NaOH (mM) | 500 | 600 | 700 | 800 | 900 | 1000 | 1100 | 1200 |
| C200P400Ca400Cl800 | 1.621 | 1.733 | 2.122 | 1.972 | 1.358 | 1.731 | 1.688 | 1.768 |
| Transparency | D | D | D | D | D | D | D | D |
| Concentration of NaOH (mM) | 400 | 500 | 600 | 700 | 800 | 900 | 1000 | 1100 |
| C100P400Ca400Cl800 | 0.194 | 1.644 | 1.990 | 1.552 | 1.600 | 1.640 | 1.761 | 1.870 |
| Transparency | D | D | D | D | D | D | D | D |
| Concentration of NaOH (mM) | 2200 | 2400 | 2600 | 2800 | 3000 | 3200 | 3400 | 3600 |
| C800P200Ca400Cl800 | 2.386 | 2.349 | 2.434 | 2.409 | 0.025 | 0.026 | 0.031 | 0.365 |
| Transparency | D | D | D | D | A | A | A | D |
| Concentration of NaOH (mM) | 1300 | 1400 | 1500 | 1600 | 1700 | 1800 | 1900 | 2000 |
| C400P200Ca400Cl800 | 2.222 | 2.434 | 2.469 | 2.401 | 2.371 | 1.805 | 0.059 | 0.072 |
| Transparency | D | D | D | D | D | D | A | A |
| Concentration of NaOH (mM) | 700 | 800 | 900 | 1000 | 1100 | 1200 | 1300 | 1400 |
| C200P200Ca400Cl800 | 1.980 | 1.854 | 1.761 | 2.197 | 2.178 | 1.901 | 0.067 | 0.073 |
| Transparency | D | D | D | D | D | D | A | A |
| Concentration of NaOH (mM) | 600 | 700 | 800 | 900 | 1000 | 1100 | 1200 | 1300 |
| C100P200Ca400Cl800 | 1.488 | 2.005 | 1.992 | 1.103 | 0.178 | 0.136 | 0.158 | 0.199 |
| Transparency | D | D | D | D | B | B | B | B |
| Concentration of NaOH (mM) | 2000 | 2200 | 2400 | 2600 | 2800 | 3000 | 3200 | 3400 |
| C800P100Ca400Cl800 | 2.363 | 2.261 | 2.378 | 2.409 | 2.141 | 1.911 | 0.021 | 0.015 |
| Transparency | D | D | D | D | D | D | A | A |
| Concentration of NaOH (mM) | 1100 | 1200 | 1300 | 1400 | 1500 | 1600 | 1700 | 1800 |
| C400P100Ca400Cl800 | 1.943 | 2.222 | 2.409 | 2.417 | 2.261 | 2.233 | 2.159 | 2.129 |
| Transparency | D | D | D | D | D | D | D | D |
| Concentration of NaOH (mM) | 500 | 600 | 700 | 800 | 900 | 1000 | 1100 | 1200 |
| C200P100Ca400Cl800 | 1.723 | 1.983 | 2.034 | 2.034 | 2.002 | 2.045 | 1.921 | 1.705 |
| Transparency | D | D | D | D | D | D | D | D |
| Concentration of NaOH (mM) | 400 | 500 | 600 | 700 | 800 | 900 | 1000 | 1100 |
| C100P100Ca400Cl800 | 1.479 | 1.639 | 1.886 | 1.840 | 1.948 | 1.927 | 1.898 | 1.851 |
| Transparency | D | D | D | D | D | D | D | D |

When the concentration of citric acid was 800 mM based on 100 or 400 mM of phosphoric acid and the concentration of citric acid was from 100 to 800 mM based on 200 mM of phosphoric acid, the aqueous preparation of calcium of the present invention was obtained. The pH range in which the aqueous preparation of calcium of the present invention was obtained was from 7.22 to 13.37.

The results when the concentration of calcium was fixed to 600 mM, citric acid was modified at a concentration of 150 to 1200 mM, and phosphoric acid was modified at a concentration of 300 mM are shown in Table 5.

TABLE 5

| | pH | Ca (µM) | pH | Ca (µM) | pH | Ca (µM) | pH | Ca (µM) | pH | Ca (µM) |
|---|---|---|---|---|---|---|---|---|---|---|
| Concentration of NaOH (mM) | 3300 | | 3600 | | 3900 | | 4200 | | 4500 | |
| C1200P300Ca600Cl1200 | 4.32 | 227 | 4.95 | 67.7 | 5.93 | 28.4 | 6.76 | 25.5 | 11.7 | 12.6 |
| Transparency | D | | D | | D | | D | | D | |
| Concentration of NaOH (mM) | 1950 | | 2100 | | 2250 | | 2400 | | 2550 | |
| C600P300Ca600Cl1200 | 4.86 | 827 | 4.69 | 1300 | 5.47 | 339 | 5.81 | 133 | 6.31 | 77.7 |
| Transparency | D | | D | | D | | D | | D | |
| Concentration of NaOH (mM) | 1050 | | 1200 | | 1350 | | 1500 | | 1650 | |
| C300P300Ca600Cl1200 | 2.73 | 161000 | 3.05 | 83200 | 4.34 | 9510 | 4.98 | 4800 | 5.53 | 1360 |
| Transparency | D | | D | | D | | D | | D | |
| Concentration of NaOH (mM) | 900 | | 1050 | | 1200 | | 1350 | | 1500 | |
| C150P300Ca600Cl1200 | 3.04 | 182000 | 4.52 | 97700 | 4.45 | 32500 | 7.2 | 6650 | 11.8 | 161 |
| Transparency | D | | D | | D | | D | | D | |

| | pH | Ca (µM) | pH | Ca (µM) | pH | Ca (µM) |
|---|---|---|---|---|---|---|
| Concentration of NaOH (mM) | 4800 | | 5100 | | 5400 | |
| C1200P300Ca600Cl1200 | 13.02 | 8.54 | 13.32 | 10.7 | 13.46 | 18 |
| Transparency | A | | A | | A | |
| Concentration of NaOH (mM) | 2700 | | 2850 | | 3000 | |
| C600P300Ca600Cl1200 | 8.86 | 59.9 | 12.18 | 19.1 | 12.72 | 10.4 |
| Transparency | D | | A | | A | |
| Concentration of NaOH (mM) | 1800 | | 1950 | | 2100 | |
| C300P300Ca600Cl1200 | 7.74 | 390 | 12.06 | 91.1 | 12.74 | 31.1 |

TABLE 5-continued

| | | | | | | |
|---|---|---|---|---|---|---|
| Transparency | | D | | A | | A |
| Concentration of NaOH (mM) | | 1650 | | 1800 | | 1950 |
| C150P300Ca600Cl1200 | | 12.61 | 40.8 | 12.86 | 23.3 | 13.02 | 26 |
| Transparency | | D | | D | | D |

| Absorbance values |
|---|

| | | | | | | | | |
|---|---|---|---|---|---|---|---|---|
| Concentration of NaOH (mM) | 3300 | 3600 | 3900 | 4200 | 4500 | 4800 | 5100 | 5400 |
| C1200P300Ca600Cl1200 | 2.550 | 2.550 | 2.363 | 2.451 | 0.573 | 0.021 | 0.016 | 0.023 |
| Transparency | D | D | D | D | D | A | A | A |
| Concentration of NaOH (mM) | 1950 | 2100 | 2250 | 2400 | 2550 | 2700 | 2850 | 3000 |
| C600P300Ca600Cl1200 | 2.508 | 2.488 | 2.508 | 2.335 | 2.255 | 1.784 | 0.033 | 0.032 |
| Transparency | D | D | D | D | D | D | A | A |
| Concentration of NaOH (mM) | 1050 | 1200 | 1350 | 1500 | 1650 | 1800 | 1950 | 2100 |
| C300P300Ca600Cl1200 | 2.048 | 2.222 | 2.266 | 2.342 | 2.322 | 1.992 | 0.083 | 0.081 |
| Transparency | D | D | D | D | D | D | A | A |
| Concentration of NaOH (mM) | 900 | 1050 | 1200 | 1350 | 1500 | 1650 | 1800 | 1950 |
| C150P300Ca600Cl1200 | 1.666 | 1.664 | 2.112 | 1.851 | 0.589 | 0.366 | 0.498 | 1.921 |
| Transparency | D | D | D | D | D | D | D | D |

When the concentration of citric acid was from 300 to 1200 mM based on 300 mM of phosphoric acid, the aqueous preparation of calcium of the present invention was obtained. The pH range in which the aqueous preparation of calcium of the present invention was obtained was from 12.06 to 13.46.

Further, the ratio of citric acid:phosphoric acid:calcium was fixed to 1:1:2 and transparent solutions at concentrations of low to high were produced. The results are shown in Table 6.

TABLE 6

| | pH | Ca (μM) | pH | Ca (μM) | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|---|---|---|---|
| Concentration of NaOH (mM) | 2100 | | 2400 | | 2700 | | 3000 | | 3300 | | 3600 | | 3900 | | 4200 | |
| C600P600Ca1200Cl2400 | 2.07 | — | 2.51 | — | 4.79 | — | 4.81 | — | 5.87 | — | 9.76 | — | 12.49 | — | 12.95 | — |
| Transparency | D | | D | | D | | D | | D | | D | | D | | D | |
| Concentration of NaOH (mM) | 1400 | | 1600 | | 1800 | | 2000 | | 2200 | | 2400 | | 2600 | | 2800 | |
| C400P400Ca800Cl1600 | 2.38 | — | 2.83 | — | 4.52 | — | 4.57 | — | 5.69 | — | 8.86 | — | 12.28 | 35.4 | 12.75 | 16 |
| Transparency | D | | D | | D | | D | | D | | D | | B | | B | |
| Concentration of NaOH (mM) | 700 | | 800 | | 900 | | 1000 | | 1100 | | 1200 | | 1300 | | 1400 | |
| C200P200Ca400Cl800 | 3.14 | — | 3.43 | — | 4.84 | — | 5.27 | — | 5.56 | — | 6.61 | — | 11.76 | — | 12.95 | — |
| Transparency | D | | D | | D | | D | | D | | D | | B | | B | |
| Concentration of NaOH (mM) | 350 | | 400 | | 450 | | 500 | | 550 | | 600 | | 650 | | 700 | |
| C100P100Ca200Cl400 | 3.44 | — | 3.89 | — | 4.89 | — | 5.43 | — | 5.83 | — | 6.52 | 67 | 11.12 | — | 12.69 | — |
| Transparency | D | | D | | D | | D | | D | | A | | B | | B | |
| Concentration of NaOH (mM) | 175 | | 200 | | 225 | | 250 | | 275 | | 300 | | 325 | | 350 | |
| C50P50Ca100Cl200 | 3.65 | — | 4.28 | — | 4.9 | — | 5.46 | — | 5.9 | — | 6.48 | 13 | 8.23 | 65.4 | 11.86 | 8.16 |
| Transparency | D | | D | | D | | D | | D | | A | | B | | B | |
| Concentration of NaOH (mM) | 35 | | 40 | | 45 | | 50 | | 55 | | 60 | | 65 | | 70 | |
| C10P10Ca20Cl40 | 4.78 | — | 5.46 | — | 5.6 | — | 5.75 | — | 6.15 | 532 | 7.01 | 137 | 9.91 | 23.8 | 11.63 | — |
| Transparency | A | | D | | D | | D | | B | | A | | B | | B | |

| Absorbance values |
|---|

| | | | | | | | | |
|---|---|---|---|---|---|---|---|---|
| Concentration of NaOH (mM) | 2100 | 2400 | 2700 | 3000 | 3300 | 3600 | 3900 | 4200 |
| C600P600Ca1200Cl2400 | 2.219 | 2.2 | 2.471 | 2.484 | 2.403 | 2.167 | 1.972 | 1.848 |
| Transparency | D | D | D | D | D | D | D | D |
| Concentration of NaOH (mM) | 1400 | 1600 | 1800 | 2000 | 2200 | 2400 | 2600 | 2800 |
| C400P400Ca800Cl1600 | 2.213 | 2.26 | 2.214 | 2.132 | 2.403 | 1.678 | 0.041 | 0.046 |
| Transparency | D | D | D | D | D | D | B | B |
| Concentration of NaOH (mM) | 700 | 800 | 900 | 1000 | 1100 | 1200 | 1300 | 1400 |
| C200P200Ca400Cl800 | 1.853 | 1.873 | 2.168 | 2.232 | 2.027 | 1.347 | 0.071 | 0.071 |
| Transparency | D | D | D | D | D | D | B | B |
| Concentration of NaOH (mM) | 350 | 400 | 450 | 500 | 550 | 600 | 650 | 700 |
| C100P100Ca200Cl400 | 1.248 | 1.547 | 1.872 | 2.047 | 0.26 | 0.044 | 0.071 | 0.071 |
| Transparency | D | D | D | D | D | A | B | B |
| Concentration of NaOH (mM) | 175 | 200 | 225 | 250 | 275 | 300 | 325 | 350 |
| C50P50Ca100Cl200 | 1.343 | 0.913 | 1.34 | 1.563 | 0.139 | 0.007 | 0.033 | 0.053 |

TABLE 6-continued

| Transparency | D | D | D | D | D | A | B | B |
|---|---|---|---|---|---|---|---|---|
| Concentration of NaOH (mM) | 35 | 40 | 45 | 50 | 55 | 60 | 65 | 70 |
| C10P10Ca20Cl40 | 0.014 | 0.029 | 0.186 | 0.137 | 0.029 | 0.009 | 0.027 | 0.041 |
| Transparency | A | D | D | D | B | A | B | B |

When the ratio of citric acid:phosphoric acid:calcium was 1:1:2, the aqueous preparation of calcium of the present invention could be produced in a calcium concentration range of 20 to 800 mM.

Based on the results of Tables 2 to 6, higher concentrations of calcium tended to result in a narrower composition range for producing the aqueous preparation of calcium of the present invention, while lower concentrations of calcium tended to result in a wider composition range thereof.

The additive amount ratio of calcium and phosphoric acid was about 2:1, and the composition range for the aqueous preparation of calcium of the present invention tended to be wider.

Therefore, it is considered that when the concentration is as low as 100 mM or less, the aqueous preparation of calcium of the present invention can be obtained in a range wider than the conditions shown in this example. It is considered that the aqueous preparation of calcium of the present invention can be obtained even at a high concentration of 800 mM or more by adjusting the composition ratio of citric acid and the pH condition.

FIG. 1 is a view showing the results of Example 1 of the present invention. FIG. 1 shows a relationship among the composition and the concentration of NaOH of the aqueous preparation of calcium and the transparency of the aqueous preparation of calcium. When there is no precipitate in the aqueous preparation of calcium and the wavy line arranged in the rear surface can be visually recognized through the solution, the solution agent can be determined to be sufficiently transparent.

Example 2

Production of Aqueous Preparation of Calcium Using Calcium Hydroxide

A 2 M citric acid solution, a 2 M phosphoric acid solution, a 5 M sodium hydroxide solution were prepared using distilled water. Subsequently, calcium hydroxide was suspended in distilled water such that the solution was at a predetermined concentration so that a suspension was obtained. A citric acid solution and a phosphoric acid solution were mixed with the calcium hydroxide suspension such that the solution was at a predetermined concentration so that a mixed liquid was obtained. A sodium hydroxide solution was added to the mixed liquid and mixed such that the solution was at a predetermined concentration. The mixture was allowed to stand at 37° C. for one week to obtain a sample liquid. As for the obtained solution, the pH (pH/ION METER F-53, Electrode 9610-100, HORIBA, Ltd.), calcium ion concentration, (pH/ION METER F-53, Ion cluster electrode 6583-10C, Chip electrode #7683, HORIBA, Ltd.) and absorbance value (100 μL per well of 96-well plates, O.D. 595 nm, BioTek Instruments plate reader, EL312e) were measured.

The results are shown in Table 7.

TABLE 7-1

| | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|
| Concentration of NaOH (mM) | 400 | | 450 | | 500 | | 550 | | 600 | | 650 | |
| C200P200Ca200 | 5.64 | — | 5.74 | — | 5.76 | — | 5.83 | — | 5.94 | 245 | 6.28 | 147 |
| Transparency | D | | D | | D | | D | | A | | A | |
| Concentration of NaOH (mM) | 200 | | 250 | | 300 | | 350 | | 400 | | 450 | |
| C100P200Ca200 | 5.54 | — | 5.62 | — | 5.68 | 428 | 6.12 | 172 | 6.66 | 82.3 | 7.88 | 22 |
| Transparency | D | | D | | B | | B | | D | | D | |
| Concentration of NaOH (mM) | 100 | | 150 | | 200 | | 250 | | 300 | | 350 | |
| C50P200Ca200 | 5.8 | — | 5.5 | 889 | 6.04 | 224 | 6.76 | 69 | 8.32 | 14.2 | 11.18 | — |
| Transparency | D | | D | | D | | D | | D | | D | |
| Concentration of NaOH (mM) | 300 | | 350 | | 400 | | 450 | | 500 | | 550 | |
| C200P100Ca200 | 5.92 | — | 5.93 | — | 6.03 | — | 6.18 | 380 | 6.82 | 214 | 10.16 | 617 |
| Transparency | D | | D | | D | | D | | A | | A | |
| Concentration of NaOH (mM) | 50 | | 100 | | 150 | | 200 | | 250 | | 300 | |
| C100P100Ca200 | 4.69 | — | 5.82 | — | 6.05 | — | 6.48 | 333 | 8.42 | 116 | 12.17 | — |
| Transparency | D | | D | | D | | A | | A | | A | |
| Concentration of NaOH (mM) | 0 | | 50 | | 100 | | 150 | | 200 | | | |
| C50P100Ca200 | 5.28 | — | 6.68 | — | 9.95 | 93 | 12.15 | — | 12.53 | — | | |
| Transparency | D | | D | | D | | D | | D | | | |
| Concentration of NaOH (mM) | 200 | | 250 | | 300 | | 350 | | 400 | | 450 | |
| C200P50Ca200 | 5.19 | — | 6.04 | — | 6.41 | — | 6.83 | — | 11.52 | — | 12.38 | — |
| Transparency | D | | D | | D | | D | | D | | B | |
| Concentration of NaOH (mM) | 0 | | 50 | | 100 | | 150 | | 200 | | 250 | |
| C100P50Ca200 | 4.86 | — | 6.87 | — | 11.3 | — | 12.29 | — | 12.52 | — | 12.7 | — |
| Transparency | D | | D | | D | | D | | D | | D | |

TABLE 7-1-continued

| Concentration of NaOH (mM) | 0 | | 50 | | 100 | |
|---|---|---|---|---|---|---|
| C50P50Ca200 | 12.12 | — | 12.36 | — | 12.61 | — |
| Transparency | D | | D | | D | |

| | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 700 | | 750 | | 800 | | 850 | | 900 | |
| C200P200Ca200 | 6.93 | 61 | 7.93 | 18 | 11.23 | — | 11.52 | — | 12.43 | — |
| Transparency | C | | D | | D | | D | | D | |
| Concentration of NaOH (mM) | 500 | | 550 | | 600 | | | | | |
| C100P200Ca200 | 11.1 | — | 11.95 | — | 12.42 | — | | | | |
| Transparency | D | | D | | D | | | | | |
| Concentration of NaOH (mM) | 400 | | 450 | | | | | | | |
| C50P200Ca200 | 11.9 | — | 12.31 | — | | | | | | |
| Transparency | D | | D | | | | | | | |
| Concentration of NaOH (mM) | 600 | | 650 | | 700 | | | | | |
| C200P100Ca200 | 12.21 | — | 12.6 | — | 12.79 | — | | | | |
| Transparency | A | | A | | A | | | | | |
| Concentration of NaOH (mM) | 350 | | 400 | | | | | | | |
| C100P100Ca200 | 12.56 | — | 12.72 | — | | | | | | |
| Transparency | A | | A | | | | | | | |
| Concentration of NaOH (mM) | | | | | | | | | | |
| C50P100Ca200 | | | | | | | | | | |
| Transparency | | | | | | | | | | |
| Concentration of NaOH (mM) | 500 | | 550 | | 600 | | | | | |
| C200P50Ca200 | 12.59 | — | 12.75 | — | 12.85 | — | | | | |
| Transparency | A | | A | | A | | | | | |
| Concentration of NaOH (mM) | 300 | | | | | | | | | |
| C100P50Ca200 | 12.82 | — | | | | | | | | |
| Transparency | D | | | | | | | | | |
| Concentration of NaOH (mM) | | | | | | | | | | |
| C50P50Ca200 | | | | | | | | | | |
| Transparency | | | | | | | | | | |

TABLE 7-2

| Absorbance values | | | | | | | | | | |
|---|---|---|---|---|---|---|---|---|---|---|
| Concentration of NaOH (mM) | 400 | 450 | 500 | 550 | 600 | 650 | 700 | 750 | 800 | 850 | 900 |
| C200P200Ca200 | 2.110 | 2.080 | 1.900 | 1.360 | 0.094 | 0.092 | 0.133 | 0.455 | 0.772 | 0.847 | 0.906 |
| Transparency | D | D | D | D | A | A | C | D | D | D | D |
| Concentration of NaOH (mM) | 200 | 250 | 300 | 350 | 400 | 450 | 500 | 550 | 600 | | |
| C100P200Ca200 | 1.920 | 0.567 | 0.105 | 0.098 | 0.226 | 0.619 | 0.766 | 0.816 | 0.919 | | |
| Transparency | D | D | B | B | D | D | D | D | D | | |
| Concentration of NaOH (mM) | 100 | 150 | 200 | 250 | 300 | 350 | 400 | 450 | | | |
| C50P200Ca200 | 1.580 | 0.833 | 0.603 | 0.761 | 0.980 | 1.010 | 1.080 | 1.070 | | | |
| Transparency | D | D | D | D | D | D | D | D | | | |
| Concentration of NaOH (mM) | 300 | 350 | 400 | 450 | 500 | 550 | 600 | 650 | 700 | | |
| C200P100Ca200 | 2.120 | 1.990 | 1.340 | 0.042 | 0.046 | 0.048 | 0.069 | 0.068 | 0.068 | | |
| Transparency | D | D | D | A | A | A | A | A | A | | |
| Concentration of NaOH (mM) | 50 | 100 | 150 | 200 | 250 | 300 | 350 | 400 | | | |
| C100P100Ca200 | 1.780 | 2.080 | 0.647 | 0.036 | 0.063 | 0.086 | 0.101 | 0.097 | | | |
| Transparency | D | D | D | A | A | A | A | A | | | |
| Concentration of NaOH (mM) | 0 | 50 | 100 | 150 | 200 | | | | | | |
| C50P100Ca200 | 1.770 | 1.380 | 0.366 | 0.399 | 0.925 | | | | | | |
| Transparency | D | D | D | D | D | | | | | | |
| Concentration of NaOH (mM) | 200 | 250 | 300 | 350 | 400 | 450 | 500 | 550 | 600 | | |
| C200P50Ca200 | 2.050 | 2.150 | 2.020 | 1.440 | 0.143 | 0.117 | 0.119 | 0.093 | 0.085 | | |
| Transparency | D | D | D | D | B | B | B | A | A | | |
| Concentration of NaOH (mM) | 0 | 50 | 100 | 150 | 200 | 250 | 300 | | | | |
| C100P50Ca200 | 1.660 | 1.810 | 1.170 | 1.160 | 0.751 | 0.681 | 0.338 | | | | |
| Transparency | D | D | D | D | D | D | D | | | | |
| Concentration of NaOH (mM) | 0 | 50 | 100 | | | | | | | | |
| C50P50Ca200 | 1.960 | 1.730 | 1.810 | | | | | | | | |
| Transparency | D | D | D | | | | | | | | |

Even if calcium hydroxide was used, the aqueous preparation of calcium of the present invention could be produced by employing a method of dissolving calcium salt in citric acid and phosphoric acid, similarly to the case of calcium chloride (see Table 3). When calcium hydroxide was used, a chloride was not added. Thus, the aqueous preparation of calcium of the present invention could be produced with the minimum components such as citric acid, phosphoric acid, calcium, and an adjuster for making the pH alkaline.

Example 3

Production of Aqueous Preparation of Calcium Using Potassium Hydroxide as pH Adjuster The results when the sodium hydroxide solution used as a pH adjuster in the method of Example 2 was replaced with a potassium hydroxide solution are shown in Table 8.

TABLE 8-1

| | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|
| Concentration of KOH (mM) | 500 | | 550 | | 600 | | 650 | | 700 | | 750 | |
| C200P200Ca200 | 5.83 | — | 5.99 | — | 6.08 | — | 6.07 | 5.66 | 6.15 | 1.4 | 6.49 | 0.5 |
| Transparency | D | | D | | D | | D | | A | | A | |
| Concentration of KOH (mM) | 300 | | 350 | | 400 | | 450 | | 500 | | 550 | |
| C100P200Ca200 | 5.83 | — | 5.95 | 15.7 | 6.24 | 2.8 | 6.66 | 0.84 | 7.54 | 0.13 | 10.42 | 0 |
| Transparency | D | | D | | A | | B | | D | | D | |
| Concentration of KOH (mM) | 200 | | 250 | | 300 | | 350 | | 400 | | 450 | |
| C50P200Ca200 | 13.6 | — | 13.6 | — | 13.62 | — | 13.6 | — | 13.6 | — | 13.6 | — |
| Transparency | D | | D | | D | | D | | D | | D | |
| Concentration of KOH (mM) | 350 | | 400 | | 450 | | 500 | | 550 | | 600 | |
| C200P100Ca200 | 5.94 | — | 6.16 | — | 6.22 | — | 6.35 | — | 6.51 | 3.18 | 7.47 | 1.04 |
| Transparency | D | | D | | D | | D | | A | | A | |
| Concentration of KOH (mM) | 50 | | 100 | | 150 | | 200 | | 250 | | 300 | |
| C100P100Ca200 | 4.44 | — | 5.83 | — | 6.24 | — | 6.38 | — | 7.8 | 3.5 | 11.66 | 0.26 |
| Transparency | D | | D | | D | | D | | A | | A | |
| Concentration of KOH (mM) | 0 | | 50 | | 100 | | 150 | | 200 | | 250 | |
| C50P100Ca200 | 5.33 | — | 6.65 | — | 8.23 | 4.57 | 12.09 | — | 12.64 | — | 12.92 | — |
| Transparency | D | | D | | D | | D | | D | | D | |
| Concentration of KOH (mM) | 200 | | 250 | | 300 | | 350 | | 400 | | 450 | |
| C200P50Ca200 | 4.81 | — | 5.5 | — | 6.31 | — | 6.66 | — | 7.02 | — | 10.31 | — |
| Transparency | D | | D | | D | | D | | D | | D | |
| Concentration of KOH (mM) | 0 | | 50 | | 100 | | 150 | | 200 | | 250 | |
| C100P50Ca200 | 5.19 | — | 6.75 | — | 11.6 | — | 12.39 | — | 12.67 | — | 12.86 | — |
| Transparency | D | | D | | D | | D | | D | | D | |
| Concentration of KOH (mM) | 0 | | 50 | | 100 | | 150 | | | | | |
| C50P50Ca200 | 12.28 | — | 12.59 | — | 12.8 | — | 12.94 | — | | | | |
| Transparency | D | | D | | D | | D | | | | | |

| | pH | Ca (μM) | pH | Ca (μM) | pH | Ca (μM) | pH | Ca (μM) | pH | Ca (μM) |
|---|---|---|---|---|---|---|---|---|---|---|
| Concentration of KOH (mM) | 800 | | 850 | | 900 | | 950 | | 1000 | |
| C200P200Ca200 | 6.91 | 0.17 | 7.5 | 0.04 | 10.49 | 0 | 11.68 | 0 | 12.31 | 0 |
| Transparency | B | | C | | D | | D | | D | |
| Concentration of KOH (mM) | 600 | | 650 | | 700 | | | | | |
| C100P200Ca200 | 11.57 | 0 | 12.21 | 0 | 12.68 | 0 | | | | |
| Transparency | D | | D | | D | | | | | |
| Concentration of KOH (mM) | 500 | | | | | | | | | |
| C50P200Ca200 | 13.75 | — | | | | | | | | |
| Transparency | D | | | | | | | | | |
| Concentration of KOH (mM) | 650 | | 700 | | 750 | | 800 | | | |
| C200P100Ca200 | 10.59 | 0.12 | 12.5 | 0.02 | 12.84 | — | 13.07 | — | | |
| Transparency | A | | A | | A | | B | | | |
| Concentration of KOH (mM) | 350 | | 400 | | 450 | | | | | |
| C100P100Ca200 | 12.63 | 0.2 | 12.87 | — | 13.07 | — | | | | |
| Transparency | A | | A | | B | | | | | |
| Concentration of KOH (mM) | | | | | | | | | | |
| C50P100Ca200 | | | | | | | | | | |
| Transparency | | | | | | | | | | |

TABLE 8-1-continued

| Concentration of KOH (mM) | 500 | 550 | 600 | 650 | 700 |
|---|---|---|---|---|---|
| C200P50Ca200 | 12.33 | 12.74 | 12.99 | 13.13 | 13.24 |
| Transparency | D | D | D | A | A |
| Concentration of KOH (mM) | 300 | | | | |
| C100P50Ca200 | 13.02 | | | | |
| Transparency | D | | | | |
| Concentration of KOH (mM) | | | | | |
| C50P50Ca200 | | | | | |
| Transparency | | | | | |

TABLE 8-2

| | Absorbance values | | | | | | | | | | |
|---|---|---|---|---|---|---|---|---|---|---|---|
| Concentration of KOH (mM) | 500 | 550 | 600 | 650 | 700 | 750 | 800 | 850 | 900 | 950 | 1000 |
| C200P200Ca200 | 1.998 | 1.510 | 0.583 | 0.296 | 0.055 | 0.056 | 0.078 | 0.113 | 0.552 | 0.612 | 0.673 |
| Transparency | D | D | D | A | A | B | C | D | D | D | |
| Concentration of KOH (mM) | 300 | 350 | 400 | 450 | 500 | 550 | 600 | 650 | 700 | | |
| C100P200Ca200 | 0.657 | 0.199 | 0.088 | 0.119 | 0.500 | 0.733 | 0.721 | 0.746 | 0.792 | | |
| Transparency | D | D | A | B | D | D | D | D | D | | |
| Concentration of KOH (mM) | 200 | 250 | 300 | 350 | 400 | 450 | 500 | | | | |
| C50P200Ca200 | 1.773 | 1.784 | 1.770 | 1.787 | 1.806 | 1.835 | 1.795 | | | | |
| Transparency | D | D | D | D | D | D | D | | | | |
| Concentration of KOH (mM) | 350 | 400 | 450 | 500 | 550 | 600 | 650 | 700 | 750 | 800 | |
| C200P100Ca200 | 2.070 | 2.072 | 1.912 | 0.308 | 0.048 | 0.047 | 0.060 | 0.057 | 0.067 | 0.062 | |
| Transparency | D | D | D | D | A | A | A | A | A | B | |
| Concentration of KOH (mM) | 50 | 100 | 150 | 200 | 250 | 300 | 350 | 400 | 450 | | |
| C100P100Ca200 | 1.775 | 1.971 | 1.373 | 0.033 | 0.056 | 0.077 | 0.081 | 0.090 | 0.115 | | |
| Transparency | D | D | D | A | A | A | A | B | | | |
| Concentration of KOH (mM) | 0 | 50 | 100 | 150 | 200 | 250 | | | | | |
| C50P100Ca200 | 1.546 | 1.503 | 0.285 | 0.284 | 0.730 | 1.069 | | | | | |
| Transparency | D | D | D | D | D | D | | | | | |
| Concentration of KOH (mM) | 200 | 250 | 300 | 350 | 400 | 450 | 500 | 550 | 600 | 650 | 700 |
| C200P50Ca200 | 1.523 | 2.053 | 2.100 | 2.067 | 1.619 | 0.677 | 0.692 | 0.720 | 0.170 | 0.087 | 0.055 |
| Transparency | D | D | D | D | D | D | D | D | D | A | A |
| Concentration of KOH (mM) | 0 | 50 | 100 | 150 | 200 | 250 | 300 | | | | |
| C100P50Ca200 | 1.476 | 1.910 | 1.666 | 1.023 | 0.346 | 0.159 | 0.144 | | | | |
| Transparency | D | D | D | D | D | D | D | | | | |
| Concentration of KOH (mM) | 0 | 50 | 100 | 150 | | | | | | | |
| C50P50Ca200 | 1.755 | 1.779 | 1.676 | 1.650 | | | | | | | |
| Transparency | D | D | D | D | | | | | | | |

Even if sodium hydroxide (see Table 7) as the pH adjuster to be used was replaced with potassium hydroxide, the aqueous preparation of calcium of the present invention could be produced similarly. From the viewpoint of the nutritional absorption of calcium, it is considered that it is more desirable to produce the aqueous preparation using potassium in place of sodium.

Example 4

Storage Test

Twenty-seven specimens of the aqueous preparation of calcium obtained from the experimental plot with a calcium concentration of 100 mM in Example 1 were allowed to stand at 37° C. The results when changes over time of the transparency, pH, and calcium ion concentration during storage were observed are shown in Table 9.

TABLE 9-1

| | Day 0 | | 1 week | | 1 month | | 2 months | | 3 months | |
|---|---|---|---|---|---|---|---|---|---|---|
| | pH | Ca (µM) | pH | Ca (µM) | pH | Ca (µM) | pH | Ca (µM) | pH | Ca (µM) |
| C400P100Ca100Cl200Na1400 | 6.82 | 11 | 6.85 | 36.4 | 6.76 | 9.22 | 6.73 | 16.7 | 6.81 | 10.1 |
| Transparency | B | | C | | C | | C | | C | |
| C400P100Ca100Cl200Na1450 | 7.63 | 2.43 | 7.68 | 8.87 | 7.62 | 1.5 | 7.61 | 3.38 | 7.67 | 2.14 |
| Transparency | A | | A | | A | | B | | B | |
| C200P100Ca100Cl200Na750 | 6.04 | 67.4 | 6.06 | 101 | 6.13 | 128 | 6.21 | 37.6 | 6.21 | 83.5 |
| Transparency | C | | C | | D | | D | | D | |
| C200P100Ca100Cl200Na850 | 7.23 | 5.17 | 7.2 | 8.72 | 7.24 | 20.8 | 7.22 | 3.3 | 7.33 | 8.62 |
| Transparency | A | | A | | A | | B | | B | |
| C100P100Ca100Cl200Na500 | 6.01 | 70 | 6.04 | 93.9 | 6.04 | 159 | 6.03 | 50.9 | 6.07 | 109 |
| Transparency | B | | B | | B | | B | | B | |

TABLE 9-1-continued

| | | | | | | | | |
|---|---|---|---|---|---|---|---|---|
| C50P100Ca100Cl200Na350 | 5.67 | 160 | 5.7 | 281 | 5.71 | 396 | 5.77 | 175 | 5.75 | 364 |
| Transparency | | C | | C | | B | | B | | B |
| C400P50Ca100Cl200Na1300 | 6.9 | 21.4 | 6.97 | 55.2 | 6.82 | 19.8 | 6.85 | 20.2 | 6.87 | 10.3 |
| Transparency | | B | | D | | D | | D | | D |
| C400P50Ca100Cl200Na1550 | 12.88 | 1.3 | 13.11 | 3.25 | 12.94 | 0.15 | 12.9 | 0.6 | 12.69 | 0.22 |
| Transparency | | A | | A | | C | | D | | D |
| C200P50Ca100Cl200Na750 | 7.07 | 39.1 | 7.2 | 34.1 | 7.13 | 111 | 7.2 | 25.1 | 7.2 | 13 |
| Transparency | | A | | A | | A | | A | | A |
| C200P50Ca100Cl200Na850 | 12.39 | 1.16 | 12.43 | 0.73 | 12.43 | 3.84 | 12.35 | 0.27 | 12.8 | 0.14 |
| Transparency | | A | | A | | B | | C | | C |
| C100P50Ca100Cl200Na425 | 6.16 | 268 | 6.19 | 192 | 6.09 | 472 | 6.12 | 242 | 6.17 | 93.5 |
| Transparency | | A | | A | | A | | D | | D |
| C100P50Ca100Cl200Na475 | 9.66 | 17.9 | 9.35 | 192 | 9.19 | 54.3 | 8.82 | 13.8 | 8.55 | 8.2 |
| Transparency | | A | | A | | A | | A | | A |
| C50P50Ca100Cl200Na300 | 6.48 | 313 | 6.59 | 176 | 6.47 | 482 | 6.51 | 261 | 6.58 | 114 |
| Transparency | | A | | A | | A | | A | | A |
| C50P50Ca100Cl200Na350 | 11.86 | 8.16 | 11.8 | 4.23 | 11.69 | 24.9 | 11.64 | 3.12 | 11.51 | 1.63 |
| Transparency | | B | | B | | B | | B | | B |
| C25P50Ca100Cl200Na250 | 10.61 | 64.6 | 1.046 | 10.46 | 10.66 | 130 | 9.86 | 42 | 9.5 | 18.4 |
| Transparency | | B | | B | | B | | B | | B |
| C25P50Ca100Cl200Na300 | 12.24 | 6.22 | 12.27 | 12.27 | 12.22 | 12.8 | 12.16 | 1.3 | 12 | 0.78 |
| Transparency | | B | | B | | B | | D | | D |

| | 4 months | | 5 months | | 6 months | | 9 months | | 12 months | |
|---|---|---|---|---|---|---|---|---|---|---|
| | pH | Ca (μM) | pH | Ca(μM) | pH | Ca (μM) | pH | Ca (μM) | pH | Ca (μM) |
| C400P100Ca100Cl200Na1400 | 6.69 | 11.7 | 6.61 | 14.3 | 6.62 | 13.3 | 6.6 | 6.81 | 6.61 | 44.7 |
| Transparency | | C | | C | | C | | C | | C |
| C400P100Ca100Cl200Na1450 | 7.57 | 2.34 | 7.45 | 3.06 | 7.48 | 2.44 | 7.45 | 1.04 | 7.5 | 8.47 |
| Transparency | | B | | B | | B | | B | | B |
| C200P100Ca100Cl200Na750 | 6.19 | 86.4 | 6.1 | 67.6 | 6.19 | 58.8 | 6.14 | 59 | 6.14 | 94.6 |
| Transparency | | D | | D | | D | | D | | D |
| C200P100Ca100Cl200Na850 | 7.27 | 8.54 | 7.18 | 7.98 | 7.2 | 7.91 | 7.14 | 5.65 | 7.17 | 11.2 |
| Transparency | | B | | B | | B | | B | | B |
| C100P100Ca100Cl200Na500 | 6.05 | 114 | 5.95 | 81.5 | 6.01 | 96.4 | 5.97 | 73.5 | 5.98 | 118 |
| Transparency | | B | | B | | B | | B | | B |
| C50P100Ca100Cl200Na350 | 5.74 | 349 | 5.66 | 227 | 5.72 | 266 | 5.66 | 190 | 5.68 | 257 |
| Transparency | | B | | B | | B | | B | | B |
| C400P50Ca100Cl200Na1300 | 6.83 | 14.3 | 6.7 | 16.8 | 6.78 | 15 | 6.87 | 8.43 | 6.78 | 49.6 |
| Transparency | | D | | D | | D | | D | | D |
| C400P50Ca100Cl200Na1550 | 12.36 | 0.21 | 12 | 0.46 | 11.77 | 0.6 | 11.02 | 0.63 | 11.1 | 0.53 |
| Transparency | | D | | D | | D | | D | | D |
| C200P50Ca100Cl200Na750 | 7.18 | 20.8 | 6.98 | 31.9 | 7.14 | 14.8 | 7.12 | 53.9 | 7.34 | 84.9 |
| Transparency | | A | | A | | A | | A | | A |
| C200P50Ca100Cl200Na850 | 12 | 0.21 | 11.46 | 0.84 | 11.37 | 0.11 | 10.94 | 1.44 | 10.71 | 1.88 |
| Transparency | | D | | D | | D | | D | | D |
| C100P50Ca100Cl200Na425 | 6.16 | 160 | 5.98 | 172 | 6.11 | 86.2 | 6.19 | 160 | 6.23 | 168 |
| Transparency | | D | | D | | D | | D | | D |
| C100P50Ca100Cl200Na475 | 8.12 | 21.6 | 7.84 | 32.5 | 7.86 | 10.8 | 7.94 | 34.3 | 8.1 | 46.2 |
| Transparency | | A | | A | | A | | A | | A |
| C50P50Ca100Cl200Na300 | 6.51 | 209 | 6.39 | 254 | 6.5 | 150 | 6.53 | 312 | 6.63 | 390 |
| Transparency | | A | | A | | A | | A | | A |
| C50P50Ca100Cl200Na350 | 12.31 | 2.29 | 10.97 | 7.77 | 10.79 | 2.04 | 10.2 | 12.6 | 9.9 | 14.4 |
| Transparency | | B | | B | | B | | B | | B |
| C25P50Ca100Cl200Na250 | 9.18 | 24.6 | 8.51 | 57.2 | 8.48 | 36.9 | 8.43 | 119 | 8.55 | 130 |
| Transparency | | B | | B | | B | | B | | B |
| C25P50Ca100Cl200Na300 | 11.8 | 0.88 | 11.45 | 2.54 | 11.11 | 2.4 | 10.42 | 4.5 | 10.42 | 4.3 |
| Transparency | | D | | D | | D | | D | | D |

| | Day 0 | | 1 week | | 1 month | | 2 months | | 3 months | |
|---|---|---|---|---|---|---|---|---|---|---|
| | pH | Ca (μM) | pH | Ca (μM) | pH | Ca (μM) | pH | Ca (μM) | pH | Ca (μM) |
| C400P25Ca100Cl200Na1300 | 11.78 | 12 | 11.88 | 41.1 | 11.73 | 12.8 | 11.68 | 19 | 11.5 | 9.23 |
| Transparency | | A | | A | | A | | A | | A |
| C400P25Ca100Cl200Na1450 | 12.85 | 36.8 | 13.07 | 62.9 | 12.92 | 8.52 | 12.89 | 12.5 | 12.68 | 2.92 |
| Transparency | | A | | D | | D | | D | | D |
| C200P25Ca100Cl200Na700 | 11.84 | 39.8 | 11.74 | 63.8 | 11.6 | 128 | 11.5 | 33.3 | 11.63 | 29.5 |
| Transparency | | A | | A | | A | | D | | D |
| C200P25Ca100Cl200Na850 | 12.88 | 92.3 | 12.89 | 132 | 12.89 | 200 | 12.91 | 27.8 | 13.18 | 8.05 |
| Transparency | | A | | A | | D | | D | | D |
| C100P25Ca100Cl200Na400 | 11.73 | 211 | 11.67 | 307 | 11.73 | 211 | 11.1 | 138 | 11.2 | 126 |
| Transparency | | A | | A | | D | | D | | D |
| C100P25Ca100Cl200Na450 | 12.48 | 416 | 12.48 | 339 | 12.44 | 271 | 12.45 | 135 | 12.55 | 90.5 |
| Transparency | | A | | A | | A | | A | | A |
| C400P12.5Ca100Cl200Na1400 | 12.84 | 95.3 | 13.08 | 114 | 12.92 | 25.5 | 12.93 | 31.2 | 12.75 | 10 |
| Transparency | | A | | D | | D | | D | | D |
| C200P12.5Ca100Cl200Na750 | 12.74 | 182 | 12.82 | 231 | 12.78 | 212 | 12.79 | 70.1 | 12.8 | 21.4 |
| Transparency | | A | | D | | D | | D | | D |

TABLE 9-1-continued

| | 4 months | | 5 months | | 6 months | | 9 months | | 12 months | |
|---|---|---|---|---|---|---|---|---|---|---|
| | pH | Ca (μM) | pH | Ca (μM) | pH | Ca (μM) | pH | Ca (μM) | pH | Ca (μM) |
| C200P12.5Ca100Cl200Na800 | 12.85 | 209 | 12.9 | 277 | 12.93 | 314 | 12.98 | 102 | 13.02 | 36.5 |
| Transparency | A | | A | | D | | D | | D | |
| C100P12.5Ca100Cl200Na425 | 12.45 | 669 | 12.6 | 698 | 12.64 | 699 | 12.7 | 411 | 12.7 | 146 |
| Transparency | A | | D | | D | | D | | D | |
| C0P12.5Ca100Cl200Na75 | 11.83 | 48100 | 11.74 | 47600 | 10.74 | 38400 | 10.1 | 138000 | 10.1 | 9070 |
| Transparency | D | | D | | D | | D | | D | |

| | 4 months | | 5 months | | 6 months | | 9 months | | 12 months | |
|---|---|---|---|---|---|---|---|---|---|---|
| | pH | Ca (μM) | pH | Ca (μM) | pH | Ca (μM) | pH | Ca (μM) | pH | Ca (μM) |
| C400P25Ca100Cl200Na1300 | 11.28 | 15.3 | 11.03 | 18.3 | 10.85 | 19 | 10.28 | 9.17 | 9.87 | 50.4 |
| Transparency | A | | B | | D | | D | | D | |
| C400P25Ca100Cl200Na1450 | 12.48 | 2.86 | 12.31 | 4.93 | 12.31 | 4.74 | 11.7 | 2.06 | 10.98 | 15.3 |
| Transparency | D | | D | | D | | D | | D | |
| C200P25Ca100Cl200Na700 | 11.34 | 62.5 | 11.17 | 55 | 10.89 | 58 | 10.23 | 43.9 | 9.66 | 80 |
| Transparency | D | | D | | D | | D | | D | |
| C200P25Ca100Cl200Na850 | 12.79 | 10.1 | 12.74 | 7.39 | 12.6 | 12.5 | 12.11 | 7.13 | 11.57 | 17.5 |
| Transparency | D | | D | | D | | D | | D | |
| C100P25Ca100Cl200Na400 | 11.09 | 226 | 10.92 | 155 | 10.66 | 201 | 10.18 | 141 | 9.76 | 216 |
| Transparency | D | | D | | D | | D | | D | |
| C100P25Ca100Cl200Na450 | 12.27 | 147 | 12.13 | 105 | 11.9 | 132 | 11.42 | 106 | 11.1 | 166 |
| Transparency | D | | D | | D | | D | | D | |
| C400P12.5Ca100Cl200Na1400 | 12.56 | 9.06 | 12.4 | 12.4 | 12.47 | 11.1 | 12.06 | 5.58 | 11.47 | 29.4 |
| Transparency | D | | D | | D | | D | | D | |
| C200P12.5Ca100Cl200Na750 | 12.62 | 19.7 | 12.32 | 35.7 | 12.33 | 20.8 | 11.9 | 44.8 | 11.52 | 85.4 |
| Transparency | D | | D | | D | | D | | D | |
| C200P12.5Ca100Cl200Na800 | 12.89 | 30.4 | 12.65 | 48.7 | 12.71 | 25 | 12.48 | 43 | 12.2 | 51.5 |
| Transparency | D | | D | | D | | D | | D | |
| C100P12.5Ca100Cl200Na425 | 12.61 | 142 | 12.33 | 177 | 12.38 | 112 | 12.01 | 214 | 11.57 | 294 |
| Transparency | D | | D | | D | | D | | D | |
| C0P12.5Ca100Cl200Na75 | 10 | 6040 | 9.73 | 10400 | 9.59 | 18200 | 9.54 | 18 | 9.53 | 18.1 |
| Transparency | D | | D | | D | | D | | D | |

TABLE 9-2

| | Absorbance values | | | | |
|---|---|---|---|---|---|
| | Day 0 | 5 months | 6 months | 9 months | 12 months |
| C400P100Ca100Cl200Na1400 | 0.065 | 0.330 | 0.402 | 0.469 | 0.544 |
| Transparency | A | C | C | C | C |
| C400P100Ca100Cl200Na1450 | 0.028 | 0.117 | 0.152 | 0.206 | 0.262 |
| Transparency | A | B | B | B | B |
| C200P100Ca100Cl200Na750 | 0.593 | 1.701 | 1.669 | 1.803 | 1.800 |
| Transparency | C | D | D | D | D |
| C200P100Ca100Cl200Na850 | 0.047 | 0.061 | 0.070 | 0.093 | 0.125 |
| Transparency | A | A | A | A | A |
| C100P100Ca100Cl200Na500 | 0.110 | 0.126 | 0.133 | 0.171 | 0.185 |
| Transparency | B | B | B | B | B |
| C50P100Ca100Cl200Na350 | 0.151 | 0.116 | 0.144 | 0.135 | 0.135 |
| Transparency | C | B | B | B | B |
| C400P50Ca100Cl200Na1300 | 0.055 | 1.396 | 1.553 | 1.616 | 1.718 |
| Transparency | A | D | D | D | D |
| C400P50Ca100Cl200Na1550 | 0.031 | 0.576 | 0.601 | 0.724 | 0.831 |
| Transparency | A | D | D | D | D |
| C200P50Ca100Cl200Na750 | 0.008 | 0.053 | 0.062 | 0.068 | 0.100 |
| Transparency | A | A | A | A | A |
| C200P50Ca100Cl200Na850 | 0.016 | 0.340 | 0.366 | 0.386 | 0.414 |
| Transparency | A | D | D | D | D |
| C100P50Ca100Cl200Na425 | 0.010 | 0.938 | 1.249 | 1.590 | 1.571 |
| Transparency | A | D | D | D | D |
| C100P50Ca100Cl200Na475 | 0.012 | 0.029 | 0.035 | 0.032 | 0.042 |
| Transparency | A | A | A | A | A |
| C50P50Ca100Cl200Na300 | 0.007 | 0.035 | 0.043 | 0.054 | 0.062 |
| Transparency | A | A | A | A | A |
| C50P50Ca100Cl200Na350 | 0.053 | 0.075 | 0.085 | 0.085 | 0.109 |
| Transparency | A | A | A | A | A |
| C25P50Ca100Cl200Na250 | 0.080 | 0.061 | 0.061 | 0.063 | 0.066 |
| Transparency | A | A | A | A | A |
| C25P50Ca100Cl200Na300 | 0.192 | 0.545 | 0.701 | 0.748 | 0.945 |
| Transparency | B | D | D | D | D |
| C400P25Ca100Cl200Na1300 | 0.011 | 0.125 | 0.209 | 0.654 | 1.210 |
| Transparency | A | B | D | D | D |
| C400P25Ca100Cl200Na1450 | 0.023 | 0.439 | 0.571 | 0.834 | 1.011 |
| Transparency | A | D | D | D | D |
| C200P25Ca100Cl200Na700 | 0.059 | 1.101 | 1.287 | 1.532 | 1.627 |

TABLE 9-2-continued

| | Absorbance values | | | | |
|---|---|---|---|---|---|
| | Day 0 | 5 months | 6 months | 9 months | 12 months |
| Transparency | A | D | D | D | D |
| C200P25Ca100Cl200Na850 | 0.337 | 0.772 | 0.723 | 0.627 | 0.768 |
| Transparency | A | D | D | D | D |
| C100P25Ca100Cl200Na400 | 0.019 | 0.985 | 1.152 | 1.290 | 1.398 |
| Transparency | A | D | D | D | D |
| C100P25Ca100Cl200Na450 | 0.524 | 0.615 | 0.634 | 0.662 | 0.797 |
| Transparency | A | D | D | D | D |
| C400P12.5Ca100Cl200Na1400 | 0.015 | 1.067 | 1.184 | 1.227 | 1.265 |
| Transparency | A | D | D | D | D |
| C200P12.5Ca100Cl200Na750 | 0.001 | 0.703 | 0.800 | 0.935 | 1.010 |
| Transparency | A | D | D | D | D |
| C200P12.5Ca100Cl200Na800 | 0.007 | 0.842 | 1.015 | 1.004 | 1.154 |
| Transparency | A | D | D | D | D |
| C100P12.5Ca100Cl200Na425 | 0.014 | 0.566 | 1.229 | 1.752 | 1.553 |
| Transparency | A | D | D | D | D |
| C0P12.5Ca100Cl200Na75 | 0.123 | 0.348 | 0.723 | 0.808 | 0.018 |
| Transparency | D | D | D | D | D |

After one week, the precipitation was caused in most of the specimens of the aqueous preparation having a phosphoric acid concentration of 12.5 mM. After one month, the precipitation was caused in most of the specimens of the aqueous preparation of calcium having a phosphoric acid concentration of 25 mM. However, in the cases of the phosphoric acid concentrations of 50 mM and 100 mM, the initial transparency of most of the specimens was maintained even after three months. From the viewpoint of storage life, it was shown that the concentration of 50 mM or more was excellent. Compared to the data after three months, little change was recognized in the data after four months, five months, six months, and one year, respectively. It was considered that both the transparent sample liquid and the cloudy sample liquid were in a stable state.

FIGS. 2 to 5 are views showing the results of Example 4. FIGS. 2 to 5 show changes over time of the transparency of the aqueous preparation of calcium. When there is no precipitate in the aqueous preparation of calcium and the wavy line arranged in the rear surface can be visually recognized through the solution, the solution agent can be determined to be sufficiently transparent.

Example 5

Aging Temperature

The results when the aqueous preparation of calcium was produced by setting the aging temperature to 4° C., 37° C. or 60° C. in the method of Example 1 are shown in Table 10.

TABLE 10

| | pH | Ca (μM) | pH | Ca (μM) | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|---|---|---|---|
| Concentration of NaOH (mM) | 650 | | 700 | | 750 | | 800 | | 850 | | 900 | | 950 | | 1000 | |
| 4° C. C200P100Ca200Cl400 | 5.03 | — | 5.72 | — | 6.46 | — | 6.8 | — | 7.17 | — | 9.34 | 306 | 12.13 | — | 12.49 | — |
| Transparency | D | | D | | D | | D | | D | | D | | D | | A | |
| 37° C. C200P100Ca200Cl400 | 5 | — | 5.7 | — | 5.92 | — | 6.01 | — | 6.28 | — | 7.06 | 298 | 11.06 | 75 | 12.05 | — |
| Transparency | D | | D | | D | | D | | D | | A | | A | | B | |
| 60° C. C200P100Ca200Cl400 | 4.68 | — | 5.01 | — | 5.55 | — | 5.82 | — | 6.06 | — | 6.66 | — | 10.59 | 73 | 12.02 | — |
| Transparency | D | | D | | D | | D | | D | | D | | B | | B | |
| Concentration of NaOH (mM) | 350 | | 400 | | 450 | | 500 | | 550 | | 600 | | 650 | | 700 | |
| 4° C. C100P100Ca200Cl400 | 3.48 | — | 4.2 | — | 5.28 | — | 5.95 | — | 6.61 | 1560 | 8.83 | 522 | 12.13 | — | 12.38 | — |
| Transparency | D | | D | | D | | D | | D | | D | | D | | B | |
| 37° C. C100P100Ca200Cl400 | 3.42 | — | 4 | — | 4.9 | — | 5.6 | — | 5.92 | — | 6.72 | 568 | 11.2 | — | 12.18 | — |
| Transparency | D | | D | | D | | D | | D | | A | | B | | B | |
| 60° C. C100P100Ca200Cl400 | 3.48 | — | 3.78 | — | 4.51 | — | 5.24 | — | 5.56 | — | 6.34 | — | 10.49 | 110 | 12.01 | — |
| Transparency | D | | D | | D | | D | | D | | D | | B | | B | |
| Concentration of NaOH (mM) | 250 | | 300 | | 350 | | 400 | | 450 | | 500 | | | | | |
| 4° C. C50P100Ca200Cl400 | 3.86 | — | 4.52 | — | 5.22 | — | 6 | — | 8.05 | — | 12.02 | — | | | | |
| Transparency | D | | D | | D | | D | | D | | D | | | | | |
| 37° C. C50P100Ca200Cl400 | 3.64 | — | 3.95 | — | 4.6 | — | 5.07 | — | 6.24 | 1290 | 10.55 | 130 | | | | |
| Transparency | D | | D | | D | | D | | C | | B | | | | | |
| 60° C. C50P100Ca200Cl400 | 3.4 | — | 3.72 | — | 4.25 | — | 4.77 | — | 5.84 | 1680 | 9.72 | 210 | | | | |
| Transparency | D | | D | | D | | D | | B | | C | | | | | |

| | Absorbance values | | | | | | | |
|---|---|---|---|---|---|---|---|---|
| NaOH (mM) | 650 | 700 | 750 | 800 | 850 | 900 | 950 | 1000 |
| 4° C. C200P100Ca200Cl400 | 2.130 | 2.160 | 1.950 | 0.990 | 1.970 | 1.140 | 0.990 | 0.070 |
| Transparency | D | D | D | D | D | D | D | A |
| 37° C. C200P100Ca200Cl400 | 2.050 | 2.150 | 2.010 | 1.950 | 1.860 | 0.060 | 0.030 | 0.050 |
| Transparency | D | D | D | D | D | A | A | B |
| 60° C. C200P100Ca200Cl400 | 1.900 | 1.960 | 1.950 | 1.850 | 1.110 | 0.100 | 0.050 | 0.070 |
| Transparency | D | D | D | D | D | D | B | B |

TABLE 10-continued

| NaOH (mM) | 350 | 400 | 450 | 500 | 550 | 600 | 650 | 700 |
|---|---|---|---|---|---|---|---|---|
| 4° C. C100P100Ca200Cl400 | 1.080 | 1.730 | 1.670 | 1.300 | 0.900 | 1.310 | 1.400 | 0.170 |
| Transparency | D | D | D | D | D | D | D | B |
| 37° C. C100P100Ca200Cl400 | 1.610 | 1.700 | 1.850 | 2.040 | 0.720 | 0.030 | 0.070 | 0.080 |
| Transparency | D | D | D | D | D | A | B | B |
| 64° C. C100P100Ca200Cl400 | 1.050 | 1.520 | 1.920 | 1.980 | 1.020 | 0.180 | 0.090 | 0.110 |
| Transparency | D | D | D | D | D | D | B | B |
| NaOH (mM) | 250 | 300 | 350 | 400 | 450 | 500 | | |
| 4° C. C50P100Ca200Cl400 | 0.460 | 1.160 | 1.050 | 1.340 | 1.470 | 1.350 | | |
| Transparency | D | D | D | D | D | D | | |
| 37° C. C50P100Ca200Cl400 | 1.650 | 1.620 | 0.980 | 1.670 | 0.310 | 0.160 | | |
| Transparency | D | D | D | D | C | B | | |
| 60° C. C50P100Ca200Cl400 | 0.650 | 1.330 | 1.480 | 1.810 | 0.140 | 0.210 | | |
| Transparency | D | D | D | D | B | C | | |

The aqueous preparation of calcium of the present invention could be obtained at any aging temperature. In the cases of 37° C. and 60° C., the aqueous preparation of calcium could be obtained in almost the same range. On the other hand, in the case of 4° C., the range in which the aqueous preparation of calcium could be obtained was narrower than the ranges in the cases of 37° C. and 60° C.

Example 6

Further Aqueous Preparation of Calcium

The components contained in the aqueous preparation of calcium obtained in the above example can be further modified.

A 2 M citric acid solution, a 2 M phosphoric acid solution, a 5 M sodium hydroxide solution and 500 mM sodium fluoride were prepared using distilled water. Subsequently, calcium hydroxide was suspended in distilled water such that the solution was at a predetermined concentration so that a suspension was obtained. A citric acid solution, a phosphoric acid solution, and a sodium fluoride solution were mixed with the suspension such that the solution was at a predetermined concentration so that a mixed liquid was obtained. Then, a sodium hydroxide solution was added to the mixed liquid and mixed such that the solution was at a predetermined concentration. The mixture was allowed to stand at 37° C. for one week to obtain a sample liquid.

As for the obtained aqueous preparation, the pH (pH/ION METER F-53, Electrode 9610-10D, HORIBA, Ltd.), calcium ion concentration (pH/ION METER, Ion cluster electrode 6583-10C, Chip electrode #7683, HORIBA, Ltd.), fluoride ion concentration (pH/ION METER, Ion cluster electrode 6583-10C, Chip electrode #7661, HORIBA, Ltd.), and absorbance value (100 μL per well of 96-well plates, O.D. 595 nm, BioTek Instruments plate reader, EL312e) were measured. The transparency of the modified aqueous preparation of calcium was determined based on the results obtained by visual and absorbance values, similarly to the above aqueous preparation of calcium.

The results are shown in Table 11.

TABLE 11

| | pH | Ca (μM) | F (μM) | pH | Ca (μM) | F (μM) | pH | Ca (μM) | F (μM) | pH | Ca (μM) | F (μM) | pH | Ca (μM) | F (μM) |
|---|---|---|---|---|---|---|---|---|---|---|---|---|---|---|---|
| Concentration of NaF (mM) | | 0 | | | 10 | | | 20 | | | 30 | | | 40 | |
| C100P100Ca200NaOH100 | 6.01 | 362 | 1.86 | 5.28 | 488 | 3.9 | 5.07 | 499 | 48 | 4.94 | 498 | 630 | 4.9 | 494 | 1530 |
| Transparency | | D | | | D | | | D | | | D | | | D | |
| C100P100Ca200NaOH150 | 6.27 | 194 | 2.9 | 5.8 | 347 | 1 | 5.61 | 295 | 35 | 5.56 | 216 | 430 | 5.6 | 161 | 2100 |
| Transparency | | D | | | D | | | A | | | A | | | A | |
| C100P100Ca200NaOH200 | 6.77 | 129 | 4.2 | 6.76 | 103 | 2.3 | 6.73 | 70.8 | 42 | 6.72 | 48.6 | 520 | 6.6 | 52.4 | 530 |
| Transparency | | A | | | A | | | A | | | A | | | A | |
| C100P100Ca200NaOH250 | 11.15 | 9.85 | 22 | 11.1 | 6.94 | 35 | 11.37 | 3.87 | 320 | 12.07 | 2.8 | 2900 | 12.2 | 2.8 | 6700 |
| Transparency | | A | | | B | | | B | | | A | | | A | |
| C100P100Ca200NaOH300 | 12.3 | 2.7 | 75 | 12.48 | 2.02 | 220 | 12.51 | 1.76 | 1310 | 12.6 | 1.47 | 4400 | 12.61 | 1.2 | 8400 |
| Transparency | | B | | | B | | | B | | | B | | | B | |

| | Absorbance values | | | | |
|---|---|---|---|---|---|
| Concentration of NaF (mM) | 0 | 10 | 20 | 30 | 40 |
| C100P100Ca200NaOH100 | 2.08 | 1.97 | 1.83 | 1.72 | 1.27 |
| Transparency | D | D | D | D | D |
| C100P100Ca200NaOH150 | 1.11 | 1.15 | 0.10 | 0.06 | 0.04 |
| Transparency | D | D | A | A | A |
| C100P100Ca200NaOH200 | 0.04 | 0.04 | 0.04 | 0.04 | 0.03 |
| Transparency | A | A | A | A | A |
| C100P100Ca200NaOH250 | 0.09 | 0.10 | 0.10 | 0.07 | 0.07 |
| Transparency | A | B | B | A | A |
| C100P100Ca200NaOH300 | 0.14 | 0.13 | 0.15 | 0.11 | 0.14 |
| Transparency | B | B | B | B | B |

When sodium fluoride was not added, the aqueous preparation of calcium according to the present invention could not be prepared under the condition of 100 mM citric acid, 100 mM phosphoric acid, 200 mM calcium, 150 mM sodium hydroxide. However, the aqueous preparation of calcium could be produced by adding 20 mM or more of sodium fluoride and performing aging.

The fluoride ion concentration in the solution to which sodium fluoride has been added and aged is 10% or less of the total amount of fluoride. Accordingly, it was considered that the fluoride in the solution formed a complex bound to the compound of Formula I and/or the compound of Formula II together with a non-ionic calcium. On the other hand, in the case of addition of sodium chloride, such a phenomenon was not observed.

For example, the aqueous preparation of calcium obtained in the present example can be used similarly to the above other aqueous preparations of calcium not containing fluoride.

Example 7

Freeze-Drying

The aqueous preparation of calcium obtained in the above example can be converted to a solid preparation of calcium by freeze-drying. The aqueous preparation of calcium containing 200 mM calcium was produced by the method of Example 1 and freezed at −80° C. overnight, followed by freeze-drying using a freeze dryer (EYELA FREEZE DRYER FD-5N). Distilled water was added to the dried powder so as to have the same concentration as that before drying. Further, as for the obtained aqueous preparation, the pH (pH/ION METER F-53, Electrode 9610-10D, HORIBA, Ltd.), calcium ion concentration (pH/ion meter F-53, Ion cluster electrode 6583-10C, Chip electrode #7683, HORIBA, Ltd.), and absorbance value (100 μL per well of 96-well plates, O.D. 595 nm, BioTek Instruments plate reader, and EL312e) were measured.

The results are shown in Table 12.

TABLE 12-1

| | pH | Ca (μM) | pH | Ca (μM) | pH | Ca (μM) | pH | Ca (μM) | pH | Ca (μM) | pH | Ca (μM) | pH | Ca (μM) | pH | Ca (μM) |
|---|---|---|---|---|---|---|---|---|---|---|---|---|---|---|---|---|
| Before FD | | | | | | | | | | | | | | | | |
| Concentration of NaOH (mM) | 1400 | | 1425 | | 1450 | | 1475 | | 1500 | | 1525 | | 1550 | | 1575 | |
| C400P100Ca200Cl400 | 6.81 | — | 7.03 | — | 7.32 | — | 8 | 13 | 9.87 | 4.41 | 11.91 | 1.84 | 12.44 | 1.1 | 12.65 | 0.86 |
| Transparency | D | | D | | D | | A | | A | | A | | A | | A | |
| Concentration of NaOH (mM) | 850 | | 875 | | 900 | | 925 | | 950 | | 975 | | 1000 | | 1025 | |
| C200P100Ca200Cl400 | 6.68 | — | 7.07 | 72.6 | 9.37 | 16.7 | 11.69 | 5.21 | 12.24 | 2.9 | 12.53 | 2.04 | 12.7 | 1.82 | 12.81 | 1.71 |
| Transparency | D | | B | | A | | A | | A | | A | | A | | A | |
| Concentration of NaOH (mM) | 550 | | 575 | | 600 | | 625 | | 650 | | 675 | | 700 | | 725 | |
| C100P100Ca200Cl400 | 6.15 | — | 6.64 | 315 | 7.87 | 114 | 10.94 | 26.9 | 11.9 | 8.95 | 12.41 | 4.45 | 12.6 | 3.89 | 12.73 | 3.55 |
| Transparency | D | | A | | A | | B | | B | | B | | B | | B | |
| Concentration of NaOH (mM) | 400 | | 425 | | 450 | | 475 | | 500 | | 525 | | 550 | | 575 | |
| C50P100Ca200Cl400 | 5.37 | — | 5.92 | — | 8.65 | 606 | 9.75 | 161 | 11.64 | 29.8 | 12.16 | 13.4 | 12.41 | 8.32 | 12.58 | 6.56 |
| Transparency | D | | D | | B | | B | | B | | B | | B | | B | |
| After FD | | | | | | | | | | | | | | | | |
| Concentration of NaOH (mM) | 1400 | | 1425 | | 1450 | | 1475 | | 1500 | | 1525 | | 1550 | | 1575 | |
| C400P100Ca200Cl400 | 7.16 | — | 7.38 | — | 7.52 | 20.7 | 7.98 | 10.2 | 8.86 | 3.76 | 10.34 | 1.58 | 12 | 0.43 | 12.6 | 0.26 |
| Transparency | D | | D | | D | | A | | A | | A | | A | | A | |
| Concentration of NaOH (mM) | 850 | | 875 | | 900 | | 925 | | 950 | | 975 | | 1000 | | 1025 | |
| C200P100Ca200Cl400 | 6.85 | — | 7.19 | 68.7 | 8.29 | 17.3 | 10.63 | 4.63 | 12.17 | 1.18 | 12.38 | 0.5 | 12.68 | 0.32 | 12.93 | 0.21 |
| Transparency | D | | B | | A | | A | | A | | A | | A | | A | |
| Concentration of NaOH (mM) | 550 | | 575 | | 600 | | 625 | | 650 | | 675 | | 700 | | 725 | |
| C100P100Ca200Cl400 | 6.27 | — | 6.69 | 329 | 7.42 | 139 | 9.68 | 23 | 11.32 | 7.09 | 12.03 | 1.26 | 12.51 | 0.65 | 12.78 | 0.45 |
| Transparency | D | | D | | B | | D | | D | | D | | D | | D | |
| Concentration of NaOH (mM) | 400 | | 425 | | 450 | | 475 | | 500 | | 525 | | 550 | | 575 | |
| C50P100Ca200Cl400 | 5.51 | — | 6.01 | 5030 | 7 | 1360 | 7.84 | 355 | 11.19 | 34.2 | 12.08 | 5.64 | 12.41 | 2.06 | 12.8 | 1.13 |
| Transparency | D | | D | | D | | D | | D | | D | | D | | D | |
| 1 week after FD | | | | | | | | | | | | | | | | |
| Concentration of NaOH (mM) | 1400 | | 1425 | | 1450 | | 1475 | | 1500 | | 1525 | | 1550 | | 1575 | |
| C400P100Ca200Cl400 | 6.52 | 23.8 | 6.75 | 17.4 | 7.05 | 20.1 | 7.59 | 16.1 | 8.65 | 7.01 | 9.99 | 2.84 | 11.51 | 0.68 | 12.02 | 0.37 |
| Transparency | D | | D | | D | | A | | A | | A | | A | | A | |
| Concentration of NaOH (mM) | 850 | | 875 | | 900 | | 925 | | 950 | | 975 | | 1000 | | 1025 | |
| C200P100Ca200Cl400 | 6.45 | 97.7 | 6.84 | 93.6 | 8.15 | 31.5 | 10.3 | 9.22 | 10.91 | 2.87 | 10.87 | 0.73 | 1213 | 0.39 | 12.36 | 0.31 |
| Transparency | D | | D | | A | | A | | A | | B | | B | | B | |
| Concentration of NaOH (mM) | 550 | | 575 | | 600 | | 625 | | 650 | | 675 | | 700 | | 725 | |

TABLE 12-1-continued

| | pH | Ca (µM) | pH | Ca (µM) | pH | Ca (µM) | pH | Ca (µM) | pH | Ca (µM) | pH | Ca (µM) | pH | Ca (µM) | pH | Ca (µM) |
|---|---|---|---|---|---|---|---|---|---|---|---|---|---|---|---|---|
| C100P100Ca200Cl400 | 5.97 | 788 | 6.48 | 530 | 7.5 | 210 | 8.27 | 81.4 | 10.9 | 16.9 | 11.61 | 2.69 | 12.03 | 1.26 | 12.29 | 0.7 |
| Transparency | | D | | D | | B | | D | | D | | D | | D | | D |
| Concentration of NaOH (mM) | | 400 | | 425 | | 450 | | 475 | | 500 | | 525 | | 550 | | 575 |
| C50P100Ca200Cl400 | 5 | 5180 | 5.78 | 3520 | 6.8 | 1370 | 7.76 | 455 | 10.66 | 54.9 | 11.42 | 7.02 | 11.74 | 2.52 | 12.1 | 1.43 |
| Transparency | | D | | D | | D | | D | | D | | D | | D | | D |

TABLE 12-2

| | Absorbance value | | | | | | | |
|---|---|---|---|---|---|---|---|---|
| Before FD | | | | | | | | |
| Concentration of NaOH (mM) | 1400 | 1425 | 1450 | 1475 | 1500 | 1525 | 1550 | 1575 |
| C400P100Ca200Cl400 | 1.967 | 1.873 | 0.106 | 0.031 | 0.014 | 0.014 | 0.016 | 0.019 |
| Transparency | D | D | D | A | A | A | A | A |
| Concentration of NaOH (mM) | 850 | 875 | 900 | 925 | 950 | 975 | 1000 | 1025 |
| C200P100Ca200Cl400 | 1.265 | 0.096 | 0.026 | 0.030 | 0.037 | 0.045 | 0.045 | 0.048 |
| Transparency | D | B | A | A | A | A | A | A |
| Concentration of NaOH (mM) | 550 | 575 | 600 | 625 | 650 | 675 | 700 | 725 |
| C100P100Ca200Cl400 | 0.297 | 0.030 | 0.041 | 0.065 | 0.070 | 0.072 | 0.077 | 0.078 |
| Transparency | D | A | A | B | B | B | B | B |
| Concentration of NaOH (mM) | 400 | 425 | 450 | 475 | 500 | 525 | 550 | 575 |
| C50P100Ca200Cl400 | 1.193 | 0.680 | 0.084 | 0.140 | 0.140 | 0.124 | 0.135 | 0.124 |
| Transparency | D | D | B | B | B | B | B | B |
| After FD | | | | | | | | |
| Concentration of NaOH (mM) | 1400 | 1425 | 1450 | 1475 | 1500 | 1525 | 1550 | 1575 |
| C400P100Ca200Cl400 | 2.075 | 1.936 | 0.512 | 0.044 | 0.021 | 0.021 | 0.019 | 0.023 |
| Transparency | D | D | D | A | A | A | A | A |
| Concentration of NaOH (mM) | 850 | 875 | 900 | 925 | 950 | 975 | 1000 | 1025 |
| C200P100Ca200Cl400 | 1.776 | 0.173 | 0.020 | 0.035 | 0.033 | 0.041 | 0.048 | 0.051 |
| Transparency | D | B | A | A | A | A | A | A |
| Concentration of NaOH (mM) | 550 | 575 | 600 | 625 | 650 | 675 | 700 | 725 |
| C100P100Ca200Cl400 | 1.096 | 0.304 | 0.043 | 0.619 | 1.324 | 0.949 | 1.060 | 1.218 |
| Transparency | D | D | B | D | D | D | D | D |
| Concentration of NaOH (mM) | 400 | 425 | 450 | 475 | 500 | 525 | 550 | 575 |
| C50P100Ca200Cl400 | 1.997 | 1.098 | 0.832 | 1.128 | 1.215 | 1.377 | 1.305 | 1.372 |
| Transparency | D | D | D | D | D | D | D | D |
| 1 week after FD | | | | | | | | |
| Concentration of NaOH (mM) | 1400 | 1425 | 1450 | 1475 | 1500 | 1525 | 1550 | 1575 |
| C400P100Ca200Cl400 | 2.059 | 1.951 | 1.083 | 0.051 | 0.025 | 0.020 | 0.024 | 0.025 |
| Transparency | D | D | D | A | A | A | A | A |
| Concentration of NaOH (mM) | 850 | 875 | 900 | 925 | 950 | 975 | 1000 | 1025 |
| C200P100Ca200Cl400 | 1.795 | 0.228 | 0.024 | 0.033 | 0.044 | 0.081 | 0.112 | 0.106 |
| Transparency | D | D | A | A | A | A | A | A |
| Concentration of NaOH (mM) | 550 | 575 | 600 | 625 | 650 | 675 | 700 | 725 |
| C100P100Ca200Cl400 | 1.438 | 0.409 | 0.046 | 0.355 | 1.062 | 0.976 | 1.054 | 1.198 |
| Transparency | D | D | B | D | D | D | D | D |
| Concentration of NaOH (mM) | 400 | 425 | 450 | 475 | 500 | 525 | 550 | 575 |
| C50P100Ca200Cl400 | 1.999 | 1.213 | 0.783 | 1.130 | 1.205 | 1.404 | 1.318 | 1.422 |
| Transparency | D | D | D | D | D | D | D | D |

Before freeze-drying, a transparent aqueous preparation of calcium could be produced in all concentration ranges of citric acid (50 mM to 400 mM).

Each aqueous preparation was freeze-dried and redissolved in distilled water. When the concentration ranges of citric acid were 200 mM and 100 mM, the aqueous preparation of calcium could be obtained in almost the same experimental plot as that before freeze-drying. However, in the case of 100 mM citric acid, the aqueous preparation of calcium could be obtained in only the experimental plot of 600 mM sodium hydroxide. In the case of 50 mM citric acid, the aqueous preparation of calcium could not be obtained.

Example 8

Freezing

The aqueous preparation of calcium obtained in the above example can be stored by freezing. The aqueous preparation of calcium containing 200 mM calcium was produced by the method of Example 1 and freezed at −80° C. overnight. Then, the freezed product was thawed. As for the sample liquid obtained by thawing, the pH (pH/ION METER F-53, Electrode 9610-109, HORIBA, Ltd.), calcium ion concentration (pH/ion meter F-53, Ion cluster electrode 6583-100, Chip electrode #7683, HORIBA, Ltd.), and absorbance value (100 μL per well of 96-well plates, O.D. 595 nm, BioTek Instruments plate reader, and EL312e) were measured.

The results are shown in Table 13.

TABLE 13

| | pH | Ca (μM) | pH | Ca (μM) | pH | Ca (μM) | pH | Ca (μM) | pH | Ca (μM) |
|---|---|---|---|---|---|---|---|---|---|---|
| Before freezing | | | | | | | | | | |
| Concentration of NaOH (mM) | 850 | | 875 | | 900 | | 925 | | 950 | |
| C200P100Ca200Cl400 | 6.61 | 235 | 7.11 | 189 | 8.08 | 103 | 10.72 | 37.8 | 11.96 | 12 |
| Transparency | D | | B | | A | | A | | A | |
| Concentration of NaOH (mM) | 675 | | 700 | | 725 | | 750 | | 775 | |
| C150P100Ca200Cl400 | 6.03 | 453 | 6.24 | 406 | 6.64 | 362 | 7.62 | 186 | 9.76 | 81 |
| Transparency | D | | D | | A | | A | | A | |
| Concentration of NaOH (mM) | 550 | | 575 | | 600 | | 625 | | 650 | |
| C100P100Ca200Cl400 | 6.05 | 736 | 6.33 | 648 | 7.43 | 318 | 9.86 | 118 | 11.63 | 33.3 |
| Transparency | D | | A | | A | | A | | A | |
| After freezing | | | | | | | | | | |
| Concentration of NaOH (mM) | 850 | | 875 | | 900 | | 925 | | 950 | |
| C200P100Ca200Cl400 | 6.7 | 239 | 7.02 | 218 | 7.41 | 138 | 8.47 | 61.9 | 10.51 | 18.4 |
| Transparency | D | | B | | A | | A | | A | |
| Concentration of NaOH (mM) | 675 | | 700 | | 725 | | 750 | | 775 | |
| C150P100Ca200Cl400 | 6.14 | 493 | 6.39 | 402 | 6.65 | 426 | 7.22 | 242 | 7.95 | 126 |
| Transparency | D | | D | | B | | B | | A | |
| Concentration of NaOH (mM) | 550 | | 575 | | 600 | | 625 | | 650 | |
| C100P100Ca200Cl400 | 6.13 | 861 | 6.35 | 844 | 7 | 474 | 7.74 | 215 | 9.66 | 70.2 |
| Transparency | D | | A | | A | | A | | A | |

| | pH | Ca (μM) | pH | Ca (μM) | pH | Ca (μM) |
|---|---|---|---|---|---|---|
| Before freezing | | | | | | |
| Concentration of NaOH (mM) | 975 | | 1000 | | 1025 | |
| C200P100Ca200Cl400 | 12.3 | 8.33 | 12.56 | 5.02 | 12.68 | 4.23 |
| Transparency | A | | A | | A | |
| Concentration of NaOH (mM) | 800 | | 825 | | 850 | |
| C150P100Ca200Cl400 | 11.77 | 21.6 | 12.22 | 13.6 | 12.46 | 8.76 |
| Transparency | A | | A | | A | |
| Concentration of NaOH (mM) | 675 | | 700 | | 725 | |
| C100P100Ca200Cl400 | 12.1 | 18.2 | 12.4 | 11.4 | 12.58 | 9.76 |
| Transparency | A | | B | | B | |
| After freezing | | | | | | |
| Concentration of NaOH (mM) | 975 | | 1000 | | 1025 | |
| C200P100Ca200Cl400 | 11.92 | 7.22 | 12.39 | 3.54 | 12.56 | 2.86 |
| Transparency | A | | A | | B | |
| Concentration of NaOH (mM) | 800 | | 825 | | 850 | |
| C150P100Ca200Cl400 | 10.19 | 38.4 | 11.81 | 12 | 12.35 | 6.9 |
| Transparency | A | | A | | A | |
| Concentration of NaOH (mM) | 675 | | 700 | | 725 | |
| C100P100Ca200Cl400 | 11.43 | 17.9 | 12.14 | 8.64 | 12.46 | 6.05 |
| Transparency | A | | A | | B | |

| Absorbance values | | | | | | | | |
|---|---|---|---|---|---|---|---|---|
| Before freezing | | | | | | | | |
| Concentration of NaOH (mM) | 850 | 875 | 900 | 925 | 950 | 975 | 1000 | 1025 |
| C200P100Ca200Cl400 | 1.211 | 0.084 | 0.033 | 0.041 | 0.045 | 0.053 | 0.072 | 0.082 |
| Transparency | D | B | A | A | A | A | A | A |
| Concentration of NaOH (mM) | 675 | 700 | 725 | 750 | 775 | 800 | 825 | 850 |
| C150P100Ca200Cl400 | 1.674 | 1.717 | 0.080 | 0.097 | 0.046 | 0.050 | 0.061 | 0.079 |
| Transparency | D | D | A | A | A | A | A | A |
| Concentration of NaOH (mM) | 550 | 575 | 600 | 625 | 650 | 675 | 700 | 725 |
| C100P100Ca200C400 | 0.584 | 0.057 | 0.041 | 0.065 | 0.078 | 0.086 | 0.115 | 0.145 |
| Transparency | D | A | A | A | A | A | B | B |
| After freezing | | | | | | | | |
| Concentration of NaOH (mM) | 850 | 875 | 900 | 925 | 950 | 975 | 1000 | 1025 |
| C200P100Ca200Cl400 | 1.291 | 0.162 | 0.050 | 0.040 | 0.052 | 0.056 | 0.075 | 0.074 |
| Transparency | D | B | A | A | A | A | A | B |
| Concentration of NaOH (mM) | 675 | 700 | 725 | 750 | 775 | 800 | 825 | 850 |

TABLE 13-continued

| | | | | | | | | |
|---|---|---|---|---|---|---|---|---|
| C150P100Ca200Cl400 | 1.843 | 1.903 | 0.158 | 0.137 | 0.041 | 0.046 | 0.056 | 0.072 |
| Transparency | D | D | B | B | A | A | A | A |
| Concentration of NaOH (mM) | 550 | 575 | 600 | 625 | 650 | 675 | 700 | 725 |
| C100P100Ca200C400 | 0.784 | 0.095 | 0.050 | 0.042 | 0.049 | 0.053 | 0.085 | 0.137 |
| Transparency | D | A | A | A | A | A | A | B |

A difference in transparency between before and after freezing was not observed. Accordingly, it was considered that freezing had no effect on the stability of the aqueous preparation of calcium.

Comparative Example

Phosphoric acid and calcium chloride were mixed at various concentrations and aged in the same manner as Example 1 except that aconitic acid, malic acid, tartaric acid, glycine, alanine, and lysine were used in place of citric acid. In the case of a high concentration of tartaric acid, a transparent solution was obtained. However, in most of the other cases, the aqueous preparation of calcium of the present invention was not obtained.

Example 9

Examination for Preparation Manner and Order of Blending of Test Solutions

In the following examples, all test solutions were prepared so that the composition included 100 mM citric acid, 100 mM phosphoric acid, and 200 mM calcium, the concentration of sodium was 225 mM at the time of using calcium hydroxide, the concentration of sodium was 610 mM at the time of using calcium hydroxide and hydrochloric acid, and the concentration of sodium was 610 mM at the time of using calcium chloride.

The absorbance value was measured at 595 nm using a spectrophotometer (Ubest-30) manufactured by JASCO Corporation and a glass cell.

The pH was measured using a pH meter (HM-5S) manufactured by TOA Electronics, Ltd. The calcium ion concentration was measured using a pH/ion meter (F-53) manufactured by HORIBA, Ltd.

(1) Preparation of test solution {at the time of using calcium hydroxide, 100 mM citric acid, 100 mM phosphoric acid, 200 mM calcium hydroxide, 225 mM sodium hydroxide} and {at the time of using calcium chloride, 100 mM citric acid, 100 mM phosphoric acid, 200 mM calcium chloride, 610 mM sodium hydroxide}

The test solution at the time of using calcium hydroxide was prepared in the following manner. Namely, 0.741 g of calcium hydroxide was transferred to a 50 mL-volume measuring flask, 30 mL of ultrapure water was added to the flask to suspend it. Then, 5 mL of a 1 M citric acid solution was added to the resulting suspension to dissolve the calcium hydroxide. Thereafter, 5 mL of a 1 M phosphoric acid solution was added and 225 mL of a 5 M sodium hydroxide solution was added (which became cloudy at this time). The mixture was adjusted to a constant volume of 50 mL with ultrapure water. The solution was transferred to a 50 mL-volume medium bottle and used as a test solution {calcium hydroxide}.

The test solution {calcium hydroxide} was allowed to stand at 37° C. and aged for one week to obtain a transparent solution having a pH of 7.5, an absorbance value (595 nm) of 0.06, and a calcium ion concentration of less than 1 mM.

The test solution at the time of using calcium chloride was prepared in the following manner. Namely, 10 mL of ultrapure water was transferred to a 50 mL-volume measuring flask, 5 mL of a 1 M citric acid solution and 5 mL of a 1 M phosphoric acid solution were mixed thereto, followed by addition of 6.1 mL of a 5 M sodium hydroxide solution. Ten mL of 1 M calcium chloride was directly added to the 50 mL-volume measuring flask (which became cloudy at this time) and the mixture was adjusted to a constant volume of 50 mL with ultrapure water. The solution was transferred to a 50 mL-volume medium bottle and used as a test solution {calcium chloride}. The test solution {calcium chloride} was allowed to stand at 37° C. and aged for six days to obtain a transparent solution having a pH of 7.5, an absorbance value (595 nm) of 0.07, and a calcium ion concentration of less than 1 mM.

(2) Test Based on Differences in Order of Addition (Calcium Source is Calcium Chloride)

The order of addition of each component when preparing a transparent solution was examined. Each test solution was prepared two by two. Preparation of the test solution was performed in the following manner.

Namely, 4 mL of ultrapure water was transferred to a 10 mL-volume vial bottle, 1 mL of a 1 M citric acid solution and 1 mL of a 1 M phosphoric acid solution were mixed thereto, followed by addition of 1.22 mL of a 5 M sodium hydroxide solution. Then, 0.78 mL of ultrapure water was added thereto. In this case, the pH was 12.9. Thereafter, 2 mL of 1M calcium chloride was added (which became cloudy at this time). This solution was used as a test solution control. The pH of the test solution was 12.0.

The test solution to which citric acid was finally added was prepared in the following manner. Namely, 4 mL of ultrapure water was transferred to a 10 mL-volume vial bottle. One mL of a 1 M phosphoric acid solution and 1.22 mL of a 5 M sodium hydroxide solution were added to the bottle. Then, 0.78 mL of ultrapure water was added thereto. In this case, the pH was 13.9. Thereafter, 2 mL of 1 M calcium chloride was added (which became cloudy at this time) and 1 mL of a 1 M citric acid solution was immediately added thereto. This solution was used as the test solution. The pH of the test solution was 11.1.

The test solution to which phosphoric acid was finally added was prepared in the following manner. Namely, 4 mL of ultrapure water was transferred to a 10 mL-volume vial bottle. One mL of a 1 M citric acid solution and 1.22 mL of a 5 M sodium hydroxide solution were added to the bottle. Then, 0.78 mL of ultrapure water was added thereto. In this case, the pH was 14.0. Thereafter, 2 mL of 1 M calcium chloride was added to the mixture, and 1 mL of a 1 M phosphoric acid solution was immediately added thereto (which became cloudy at this time). This solution was used as the test solution. The pH of the test solution was 10.5.

The pH, absorbance (595 nm), and calcium ion concentration when each of the test solutions (all were cloudy solutions) was allowed to stand at 37° C. and aged for three days were measured (each value is an average).

The results are shown in Table 14.

TABLE 14

| Test solution | pH | Absorbance value (595 nm) | $Ca^{2+}$ (mM) |
| --- | --- | --- | --- |
| Control | 8.1 | 0.113 | <1 mM |
| Final addition of citric acid | 8.0 | 0.136 | <1 mM |
| Final addition of phosphoric acid | 7.5 | 0.098 | <1 mM |

From the test results, it was found that a transparent liquid was obtained regardless of the order of addition of citric acid, phosphoric acid, and calcium, when calcium chloride was used as the calcium source.

Example 10

Various Types of Examinations in Preparation of Transparent Solutions

All of the test solutions were prepared to contain 100 mM citric acid, 100 mM phosphoric acid, and 200 mM calcium.

(1) Difference Due to Allowing to Stand and Stirring {Calcium Source is Calcium Hydroxide}

Each sample was prepared two by two. In the test, 100 mL of a test solution having the same composition as the test solution prepared in the order shown in Example 9 {calcium hydroxide} was aged by being left to stand at 37° C. or stirring. It was examined whether there was a difference between the transparent liquids to be obtained.

Namely, 1.482 g of calcium hydroxide was transferred to a 100 mL-volume measuring flask, and 70 mL of ultrapure water was added to the flask to suspend it. Then, 10 mL of 1 M citric acid solution was added to the resulting suspension to dissolve the calcium hydroxide. Thereafter, 10 mL of a 1 M phosphoric acid solution was added and left for 10 minutes. Thereafter, 4.5 mL of a 5 M sodium hydroxide solution was added thereto (which became cloudy at this time) and the mixture was adjusted to a constant volume of 100 mL with ultrapure water. This solution was transferred to a 100 mL-volume medium bottle and used as the test solution.

The pH, absorbance value (595 nm), and calcium ion concentration when the test solutions (all were cloudy solutions) were allowed to stand at 37° C. or stirred and aged were measured (each value is an average).

The results are shown in Table 15.

TABLE 15

| | | On day 3 | | On day 13 | | |
| --- | --- | --- | --- | --- | --- | --- |
| Sample | Initial pH | pH | Absorbance value (595 nm) | pH | Absorbance value (595 nm) | $Ca^{2+}$ (mM) |
| Test solution (allowed to stand) | 11.3 | 7.9 | 0.18 | 7.5 | 0.15 | <1 mM |
| Test solution (stirred) | 11.3 | 7.8 | 0.18 | 7.4 | 0.18 | <1 mM |

Each test solution was allowed to stand or stirred to obtain a transparent solution. Further, a large difference was not observed in the pH, absorbance value (595 nm), or calcium ion concentration of the obtained transparent solutions.

(2) Preparation of Transparent Solution Using Different Phosphates {Calcium Source is Calcium Hydroxide}

1.482 g of calcium hydroxide was transferred to a 100 mL-volume measuring flask. Then, 60 to 70 mL of ultrapure water was added thereto and to suspend them. Then, 10 mL of 1 M citric acid solution was added to the suspension and the mixture was treated with ultrasonic for a short time. A sodium hydroxide solution was added thereto so that each final concentration of sodium was 225 mM. A phosphate solution was added thereto (which became cloudy at this time) and the mixture was adjusted to a constant volume of 100 mL with ultrapure water. This solution was transferred to a medium bottle and aged at 37° C. A kind of the phosphate and the additive amount of the phosphate solution used for the test as well as the additive amount of the 5 M sodium hydroxide solution are shown in Table 16.

As for trisodium monophosphate, the test solution was prepared in the following manner. Namely, 1.48 g of calcium hydroxide was transferred to a 100 mL-volume measuring flask, and 15 mL of a 2 M hydrochloric acid solution was added thereto to dissolve it. The resulting mixture was suspended with 30 mL of ultrapure water and then 10 mL of a 1 M citric acid solution was added. Then, 40 mL of a 250 mM trisodium monophosphate solution was added after 15 minutes, and 4.2 mL of a 5 M sodium hydroxide solution was added. The mixture was immediately adjusted to a constant volume of 100 mL with ultrapure water. This solution was transferred to a medium bottle and aged at 37° C.

TABLE 16

| Phosphate | Additive amount of phosphoric acid solution | Additive amount of 5M NaOH solution {the number in parentheses represents the concentration of Na in a test solution} |
| --- | --- | --- |
| Phosphoric acid | 1M solution: 10 ml | 4.5 ml (225 mM) |
| Disodium hydrogen phosphate | 500 mM solution: 20 ml | 0.5 ml (225 mM) |
| Trisodium phosphate | 250 mM solution: 40 ml | 0 ml (300 mM) |

The measurement results of the pH, absorbance value (595 nm), and calcium ion concentration when each of the test solutions (all were cloudy solutions) was aged at 37° C. are shown in Table 17.

TABLE 17

| | | On day 7 | | |
| --- | --- | --- | --- | --- |
| Sample | Initial pH | pH | Absorbance value (595 nm) | $Ca^{2+}$ (mM) |
| Phosphoric acid | 9.2 | 8.2 | 0.341 | <1 mM |
| Disodium hydrogen phosphate | 11.7 | 8.7 | 0.154 | <1 mM |
| Trisodium phosphate | 13.0 | 9.5 | 0.163 | <1 mM |

In the case of all the test solutions which were prepared using various kinds of phosphates, a transparent solution was obtained.

(3) Preparation of Transparent Solution Using Citrate and Phosphate (Calcium Source is Calcium Chloride)

The transparent liquids when calcium chloride was used as the calcium source, citric acid and trisodium citrate were used as the source of the compound of Formula I, phosphoric acid and disodium hydrogenphosehate were used as the source of the compound of Formula II were examined.

In other words, three kinds of test solutions were prepared using calcium chloride as the calcium source, citric acid and phosphoric acid, citric acid and disodium hydrogenphosphate, and trisodium citrate and disodium hydrogenphosphate in the following manner and aged at 37° C. Then, the transparent liquids were compared.

Each sample was prepared two by two. In the solution prepared using citric acid and phosphoric acid, 15 mL of ultrapure water was poured into a 50 mL-volume medium bottle, and 5 mL of a 1 M citric acid solution and 5 mL of a 1 M phosphoric acid solution were added thereto. The resulting mixture was left for 5 minutes, followed by addition of 6.1 mL of a 5 M sodium hydroxide solution. Then, 8.9 mL of ultrapure water was added after 5 minutes and 10 mL of 1 M calcium chloride was then added (which became cloudy at this time). The resulting mixture was used as the test solution.

In the solution prepared using citric acid and disodium hydrogenphosphate, 12 mL of ultrapure water was poured into a 50 mL-volume medium bottle, and 5 mL of a 1 M citric acid solution and 10 mL of a 0.5 M disodium hydrogenphosphate solution were added thereto. The resulting mixture was left for 5 minutes, followed by addition of 4.1 mL of a 5 M sodium hydroxide solution. Then, 8.9 mL of ultrapure water was added after 5 minutes and 10 mL of 1 M calcium chloride was added (which became cloudy at this time). The resulting mixture was used the test solution.

In the solution prepared using trisodium citrate and disodium hydrogenphosphate, 15 mL of ultrapure water was poured into a 50 mL-volume medium bottle, and then 5 mL of a 1 M trisodium citrate solution and 10 mL of a 0.5 M disodium hydrogenphosphate solution were added. The resulting mixture was left for 5 minutes, followed by addition of 1.1 mL of a 5 M sodium hydroxide solution. Then, 8.9 mL of ultrapure water was added after 5 minutes and 10 mL of 1 M calcium chloride was then added (which became cloudy at this time). The resulting mixture was used as the test solution.

The pH, absorbance value (595 nm), and calcium ion concentration when each of the test solutions (all were cloudy solutions) was allowed to stand at 37° C. and aged for two days were measured (each value is an average)® The results are shown in Table 18 below.

TABLE 18

| Citric acid source and phosphoric acid source | pH | Absorbance value (595 nm) | $Ca^{2+}$ (mM) |
| --- | --- | --- | --- |
| Citric acid and phosphoric acid | 9.2 | 0.166 | <1 mM |
| Citric acid and disodium hydrogen phosphate | 8.7 | 0.156 | <1 mM |
| Trisodium citrate and disodium hydrogen phosphate | 8.1 | 0.114 | <1 mM |

In all the test solutions, a transparent solution was obtained regardless of the combination of the sources of the compound of Formula I and the compound of Formula II.

(4) Preparation of Transparent Solution Using Calcium Citrate

In the preparation of a test solution, a method of using calcium citrate having a low solubility to water as the calcium source and the source of the compound of Formula I was examined. Namely, 285 mg of calcium citrate was transferred to a 10 mL-volume vial bottle, 6 mL of ultrapure water was added thereto to suspend it, and 1 mL of a 1 M phosphoric acid solution was added to the suspension. Then, 0.75 mL of a 5M sodium hydroxide solution was added after 30 minutes, and 0.5 mL of a 1 M calcium chloride solution was added thereto immediately. Then, 0.325 mL of 2 M hydrochloric acid was added, and then 1.425 mL of ultrapure water was added thereto immediately, and the resulting mixture was used as the test solution. In the case of this test solution, most of the calcium citrate precipitates were not dissolved, but were still in a precipitated state. The vial bottle was covered with a lid and the test solution was aged at 37° C. for one week. The initial pH was 10.7.

The test solution aged at 37° C. for one week was a cloudy liquid having a pH of 7.4 and an absorbance value (595 nm) of 2.000 or more.

As described below, a method of dissolving calcium citrate in acid and using it was examined. Namely, 285 mg of calcium citrate was transferred to a 10 mL-volume vial bottle, and 1 mL of a 2 M hydrochloric acid solution was added thereto to dissolve it. Then, 5 mL of ultrapure water was added thereto to suspend it and 1 mL of a 1 M phosphoric acid solution was added to the suspension. Then, 1.22 mL of a 5 M sodium hydroxide solution was added after 30 minutes, 0.5 mL of a 1 M calcium chloride solution was added immediately, and 0.78 mL of ultrapure water was added immediately. The resulting mixture was used as the test solution. The vial bottle was covered with a lid and the test solution was aged at 37° C. for one week. The aged test solution was a transparent solution having a pH of 9.7, an absorbance value (595 nm) of 0.295, and a calcium ion concentration of less than 1 mM.

From the above results, it was found that when an insoluble calcium salt was used, a transparent solution was not obtained under the condition where the calcium salt was not passed through a process of dissolving once (not ionized), and even in the case of the insoluble calcium salt, the transparent solution was obtained by dissolving the salt with acid once.

(5) Preparation of Transparent Solution Using Various Types of Calcium Phosphate In the preparation of a test solution, a method of using various types of calcium phosphate as the calcium source and the source of the compound of Formula II was examined. Calcium phosphate was weighed so that the concentration of phosphoric acid was 100 mM. Calcium chloride was added to make up for the lack of calcium to the calcium concentration (200 mM). Each sample was prepared two by two.

The test solution produced using phosphoric acid, which was used as a comparison, was prepared in the following manner. Namely, 4 mL of ultrapure water, 1 mL of a 1 M citric acid solution, and 1 mL of a 1 M phosphoric acid solution were added to a 10 mL-volume vial bottle. Then, 2 mL of 1 M calcium chloride was added thereto after 15 minutes, and 1.22 mL of a 5 M sodium hydroxide solution was added after 15 minutes (which became cloudy at this time). Then, 0.78 mL of ultrapure water was added thereto immediately, and the resulting mixture was used as the test solution.

On the other hand, the test solution using various types of calcium phosphate was prepared in the following manner. Calcium bis(dihydrogen phosphate)-monohydrate {Ca$(H_2PO_4)_2$—$H_2O$} and calcium hydrogenphosphate-dihydrate (CaHPO$_4$.2H$_2$O) were used as calcium phosphate.

In the test solution prepared using calcium bis(dihydrogen phosphate)-monohydrate {Ca($H_2PO_4$)$_2$—$H_2O$}, 126 mg of calcium bis(dihydrogen phosphate)-monohydrate was transferred to a 10 mL-volume vial bottle, and 6 mL of ultrapure water was added thereto to suspend it. Then, 1 mL of a 1 M citric acid solution was added thereto. Then, 1.5 mL of a 1 M calcium chloride solution was added thereto after 15 minutes. The resulting mixture was left for 15 minutes, and then 1.02 mL of a 5 M sodium hydroxide solution was added thereto. Then, 0.98 mL of ultrapure water was added thereto immediately, and the mixture was used as the test solution. In the test solution prepared using calcium hydrogenphosphate-dihydrate ($CaHPO_4 \cdot 2H_2O$), 172 mg of calcium hydrogenphosphate-dihydrate was transferred to a 10 mL-volume vial bottle, and 1 mL of a 2 N hydrochloric acid solution was added thereto to dissolve it. Then, 5 mL of ultrapure water was added thereto to suspend it, and 1 mL of a 1 M citric acid solution was added thereto. Then, 1 mL of a 1 M calcium chloride solution was added thereto after 15 minutes. Further, the mixture was left for 15 minutes, 1.22 mL of a 5 M sodium hydroxide solution was added thereto, and 0.78 mL of ultrapure water was added thereto immediately. The resulting mixture was used as the test solution.

The pH, absorbance value (595 nm), and calcium ion concentration when each of the test solutions (all were cloudy solutions) was allowed to stand at 37° C. and aged for one week were measured (each value is an average). The results are shown in Table 19 below.

TABLE 19

| Sample | pH | Absorbance value (595 nm) | $Ca^{2+}$ (mM) |
|---|---|---|---|
| Phosphoric acid | 9.3 | 0.117 | <1 mM |
| Calcium bis (dihydrogen phosphate) | 9.8 | 0.098 | <1 mM |
| Calcium hydrogen phosphate | 8.8 | 0.125 | <1 mM |

It was shown that even when calcium phosphate was used as the calcium source and the source of the compound of Formula II, a transparent solution was obtained.

(6) Examination Regarding Aging Temperature and Time

The transparency after treatment at each temperature for a certain period of time was examined.

The test solution was produced in the following manner. The treatment at 37° C. to 90° C. was performed on the test solution prepared using disodium phosphate and trisodium citrate, while the boiling and autoclave treatment was performed on the test solution prepared using phosphoric acid and citric acid.

Namely, in the test solution prepared using disodium phosphate and trisodium citrate, 15 mL of ultrapure water was transferred to a 50 mL-volume medium bottle, and 5 mL of a 1 M trisodium citrate solution and 10 mL of a 0.5 M disodium monohydrogen phosphate solution were added thereto. Then, 1.1 mL of a 5 M sodium hydroxide solution was added thereto alter minutes, and 8.9 ml of ultrapure water was added. Thereafter, 10 mL of a 1 M calcium chloride solution was added thereto immediately (which became cloudy at this time), and the resulting mixture was used as the test solution. This test solution was aged by storing at each temperature for a certain period of time.

In the test solution prepared using phosphoric acid and citric acid, 10 mL of ultrapure water was transferred to a 50 mL-volume medium bottle, and 5 mL of a 1 M citric acid solution and 5 mL of a 1 M phosphoric acid solution were mixed thereto. Thereafter, 6.1 mL of a 5 M sodium hydroxide solution was added to the mixture, and 13.9 mL of ultrapure water was added thereto. Thereafter, 10 mL of a 1 M calcium chloride solution was added thereto immediately (which became cloudy at this time), and the resulting mixture was used as the test solution.

The test solutions which were aged at each temperature were further aged at 37° C., and then changes in the transparency were confirmed. Each of the test solutions was aged by storing at each temperature for a certain period of time.

The pH and absorbance value of each of the test solutions after aging were measured. The calcium ion concentration of the test solution which was aged at 37° C.: was measured. The results are as follows.

TABLE 20

| Aging conditions (temperature and time) | pH | Absorbance value (595 nm) | $Ca^{2+}$ (mM) |
|---|---|---|---|
| 37° C.-8 hours | 11.0 | 2,000 or more | — |
| 37° C.-4 days | 8.0 | 0.073 | <1 mM |
| 60° C.-5 hours | — | 0.203 | — |
| 60° C.-8 hours | 7.8 | 0.180 | — |
| 60° C.-8 hours, then 37° C.-4 days | 7.9 | 0.116 | <1 mM |
| 80° C.-3 hours | 7.4 | 0.305 | — |
| 80° C.-5 hours | 7.5 | 0.231 | — |
| 80° C.-5 hours, then 37° C.-1 day | 7.6 | 0.200 | <1 mM |
| 90° C.-5 hours | 7.9 | 0.364 | — |
| 90° C.-5 hrs, then 37° C.-3 days | 7.9 | 0.244 | <1 mM |
| 4 hrs boiling, then 37° C.-4 days | 8.3 | 0.954 | — |
| Autoclave (121° C.-15 minutes) | 7.4 | 2,000 or more | — |
| After autoclave, 37° C.-4 days | 7.4 | 0.811 | — |

It was found that shortening of the time for transparency may be achieved by aging under high temperatures. On the other hand, in the case of aging under high temperatures higher than a constant temperature, such as boiling and autoclave conditions, the reaction of transparency was not progressed and a target transparent solution was not obtained.

Example 11

Influence of Additive

Ten percent (w/w) by weight of glucose or glycine or 2% (w/w) by weight of sodium chloride was adjusted to add to the transparent liquid prepared at the same blend as that of trisodium citrate, disodium phosphate, and calcium chloride shown in (3) of Example 10 to prepare a test solution. Then, changes in the transparency of the test solution after storage at room temperature and 37° C. were examined.

Namely, 15 mL of ultrapure water was transferred to a 50 mL-volume medium bottle, and 5 mL of a 1 M trisodium citrate solution and a 10 mL of a 0.5 M disodium monohydrogen phosphate solution were added thereto. Then, 1.1 mL of a 5 M sodium hydroxide solution was added thereto after 5 minutes, 8.9 mL of ultrapure water was added, and 10 mL of a 1 M calcium chloride solution was added immediately (which became cloudy at this time). The resulting mixture was used as the test solution. This test solution was aged at 37° C. for one week to obtain a transparent solution. As for this transparent solution, the pH was 7.8, the absorbance value (595 nm) was 0.069, and the calcium ion concentration was less than 1 mM.

Each sample containing an additive was prepared two by two. Each of the samples containing glucose and glycine was prepared by transferring 500 mg of glucose or glycine to a 10 mL-volume vial bottle and adding the transparent solution thereto by 4.5 q. The sample containing sodium chloride was prepared by transferring 100 mg of sodium chloride to a 10 mL-vial bottle and adding the transparent solution thereto by 4.9 g.

Each of the test solutions when allowed to stand at room temperature for six days and when allowed to stand at 37° C. for nine days was analyzed.

The results are shown in Table 21.

TABLE 21

| Additive | After storage at room temperature for six days | | | After storage at room temperature for six days, at 37° C. for nine days | | |
|---|---|---|---|---|---|---|
| | pH | Absorbance value (595 nm) | $Ca^{2+}$ (mM) | pH | Absorbance value (595 nm) | $Ca^{2+}$ (mM) |
| Additive-free | 7.6 | 0.066 | <1 mM | 7.5 | 0.070 | <1 mM |
| Glucose {10% (w/w) addition} | 7.6 | 0.054 | <1 mM | 7.5 | 0.052 | <1 mM |
| Glycine {10% (w/w) addition} | 7.3 | 0.046 | <1 mM | 7.3 | 0.045 | <1 mM |
| NaCl {2% (w/w) addition} | 7.6 | 0.119 | <1 mM | 7.4 | 0.221 | <1 mM |

It was found that even when 10% (w/w) glucose as sugar, 10% (w/w) glycine as amino acid, and 2% (w/w) sodium chloride as salt were added to the transparent solution of the present invention, the transparency was maintained without producing precipitates.

Example 12

Preparation of Dried Powder of Transparent Solution (Preparation of Solid Preparation of Calcium)

Five mL of the transparent solution using calcium chloride obtained in (1) of Example 9 was taken into a 50 mL glass container and dried by each method and at each temperature, followed by redissolution in 5 mL of ultrapure water. As the drying method, drying (A) by vacuum freeze-drying (FREEZE DRYER FD-5N, manufactured by Tokyo Rikakikai Co., Ltd.) and drying (B) by hot air at 50° C. and (C) at 60° C. with a drier (COVECTION OVEN, manufactured by SANYO CO., LTD.).

The pH and absorbance value (595 nm) of the solution after redissolution were measured. The results are shown in Table 22 below.

TABLE 22

| Drying conditions | pH | Absorbance value (595 nm) |
|---|---|---|
| Untreated (stock solution) | 7.5 | 0.094 |
| (A) FD | 7.5 | 0.098 |
| (B) Hot air drying at 50° C. | 7.5 | 0.222 |
| (C) Hot air drying at 60° C. | 7.5 | 0.222 |

It was found that when the dried powder obtained by FD (freeze-dry) treatment was redissolved, it almost returned to the original solution. It was found that although the redissolution solution of the dried powder obtained by hot air drying at 50° C. or 60° C. did not achieve to have the original transparency, it could be redissolved in a transparent solution without precipitates.

Example 13

Solid Preparation of Calcium Prepared by Freeze-Drying High Concentration Calcium Solution Under the following conditions, two aqueous preparations of calcium of C400P400Ca800K900 were prepared using calcium oxide as the calcium source. Then, 2.24 g of calcium oxide was suspended in 35 mL of distilled water. Then, 3.84 g of citric acid and 1.36 mL of 85% phosphoric acid were dissolved in 4.65 mL of distilled water. Thereafter, the resulting mixture was added to the calcium oxide suspension and stirred. Then, 9 mL of a 5 M potassium hydroxide solution was added thereto and stirred at 45° C.

The course of one of the two samples was observed for 96 hours (hereinafter referred to as "A"). Twenty-four hours later, the other one was freeze-dried. After 120 hours, it was dissolved in distilled water so as to have the same concentration before freeze-drying (hereinafter referred to as "B"). Under the following conditions, the pH (pH/ION METER F-53, Electrode 9610-10D, HORIBA, Ltd.), calcium ion concentration (pH/ion meter F-53, Ion cluster electrode 6583-10C, Chip electrode #7683, HORIBA, Ltd.), and absorbance value (spectrophotometer (Ubest-30), manufactured by JASCO Corporation, the measurement was performed at 595 nm using a glass cell) were measured. The results are shown in Table 23 below.

TABLE 23

| | pH | Ca (μM) | O.D. 595 |
|---|---|---|---|
| A: 24 hours later | 7.73 | 47.1 | 0.081 |
| A: 96 hours later | 6.94 | 46.9 | 2.838 |
| B: 24 hours later | 7.80 | 46.5 | 0.184 |
| B: After redissolution of FD powder | 7.20 | 83.9 | 0.121 |

In the measurement of 24 hours later, although there was a slight difference in turbidity between A and B, the two obtained aqueous preparations of calcium were transparent. When A was continuously stirred at 45° C. even 24 hours later, precipitates were produced 96 hours later. On the other hand, in the case of B which was freeze-dried 24 hours later, even when B was re-suspended in distilled water 120 hours later, the aqueous preparation of calcium became a transparent state.

As described above, it was revealed that it was possible to prepare an aqueous preparation of calcium having a high-concentration, such as a calcium concentration of 800 mM, in the case of a nearly neutral pH. It was also revealed that in the case of the aqueous preparation of calcium which produced precipitates and became less transparent with the passage of time, a transparent aqueous preparation of calcium could be easily obtained by converting the aqueous preparation of calcium in a transparent state to a solid preparation of calcium by freeze-drying or the like and re-suspending it.

Example 14

Oral Study of Solid Preparation of Calcium in Rats

A test for the improvement, effect of the solid preparation or calcium of the present invention on bone loss in low-Ca fed rats was performed using 5-week-old male Crl:CD (SD) rats. AIN-93M was administered to 4-week old rats. After habituation for one week, various kinds of feeds were administered to the rats for three weeks. As a basic feed, a feed obtained by modifying the content of calcium in AIN-93M to 0.2% (normal feed: 0.5%) was used.

The test groups included the following six groups (one group: eight rats): a low calcium fed group to which a basic feed was administered; a group to which a basic feed containing calcium carbonate at a Ca content of 0.5% was administered; a group to which a basic feed containing freeze-dried powder of a C100P100Ca200K225 solution after aging (at 37° C. for two days) at a Ca content of 0.5% was administered; a group to which a basic feed containing freeze-dried powder of a C200P100Ca200K550 solution after aging (at 37° C. for one day) a Ca content of 0.5% was administered; a group to which a basic feed containing freeze-dried powder of a C100P100Ca200K225 solution before aging at a Ca content of 0.5% was administered; and a group to which basic feed containing calcium lactate at a Ca content of 0.5% was administered.

During the test period, no significant difference in the rate of increase in body weight, food consumption, and food intake per day among the groups was observed. Further, no significant difference in the calcium intake per day among the groups other than the low calcium fed group was observed.

After three weeks, the dry weight of the extracted tibia was measured. The results are shown in FIG. 6. In FIG. 6, "A" indicates "after aging" and "B" indicates "before aging".

In the present test, as compared to the low calcium fed group, similarly to the case of calcium carbonate or calcium lactate, the bone weight was significantly increased when the calcium preparation according to the present invention was used. Even if the calcium solution was processed so as to be less bitter and transparent, absorbency equivalent to other materials was confirmed.

Example 15

Influence of Spray Drying

The aqueous preparation of calcium of the present invention can be made a solid preparation of calcium by spray drying.

The aqueous preparation of calcium of C100P100Ca200K225, C100P100Ca200C1400Na600, C100P100Ca200K225Na10F10, and C200P100Ca200K350 was spray-dried using a spray dryer (EYELA SD-1) under the conditions: inlet temperature: 135° C., outlet temperature: 85 to 95° C., BLOWER: 0.55 m$^3$/min, Air Pump: 0.3 kg/cm$^2$, and drying-rate 1 L/h. As a result, all the solutions could be mode into white powder. The theoretical yield was from 86 to 88%.

Then, distilled water was added to the dried powder so as to have the same concentration as that before drying. Further, as for the obtained aqueous preparation, the pH (pH/ION METER F-53, Electrode 9610-10D, HORIBA, Ltd.), calcium ion concentration (pH/ion meter F-53, Ion cluster electrode 6583-10C, Chip electrode #7683, HORIBA, Ltd.), and absorbance value (spectrophotometer (Ubest-30), manufactured by JASCO Corporation, the measurement was performed at 595 nm using a glass cell) were measured. The results are shown in Table 24 below.

TABLE 24

|  | pH | Concentration of Ca ion (μM) | O.D. 595 |
|---|---|---|---|
| Before spray drying |  |  |  |
| C100P100Ca200K225 | 6.64 | 109 | 0.100 |
| C200P100Ca200K550 | 6.56 | 35.5 | 0.097 |
| C100P100Ca200Na600C1400 | 6.48 | 580 | 0.111 |
| C100P100Ca200K225Na10F10 | 7.22 | 39.6 | 0.075 |
| After spray drying |  |  |  |
| C100P100Ca200K225 | 6.85 | 113 | 0.089 |
| C200P100Ca200K550 | 6.75 | 53.1 | 0.100 |
| C100P100Ca200Na600C1400 | 6.67 | 477 | 0.196 |
| C100P100Ca200K225Na10F10 | 7.31 | 57.2 | 0.075 |

The dried powder can be easily dissolved in water at the same concentration as that of the stock solution. No large difference in the pH, calcium ion concentration and absorbance value was observed between a solution of the dried powder redissolved in water and the stock solution.

Example 16

Influence of Autoclave (AC)

The aqueous preparation of calcium of the present invention can be heat-sterilized with an autoclave.

The aqueous preparation of calcium having a calcium concentration of 200 mM was produced by the method of Example 1, and the resulting preparation was heat-sterilized using an autoclave at 121° C. for 15 minutes. As for the sample liquid after autoclave, the pH (pH/ION METER F-53, Electrode 9610-10D, HORIBA, Ltd.), calcium ion concentration (pH/ion meter F-53, Ion cluster electrode 6583-10C, Chip electrode #7683, HORIBA, Ltd.), and absorbance value (100 μL per well of 96-well plates, O.D. 595 nm, BioTek Instruments plate reader, and EL312e) were measured. The results are shown in Tables 25 and 26 below.

TABLE 25

| Before AC | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 1400 |  | 1425 |  | 1450 |  | 1475 |  | 1500 |  |
| C400P100Ca200Cl400 | 6.24 | 40.9 | 6.33 | 32.3 | 6.53 | 29.6 | 6.81 | 26.8 | 7.02 | 33.4 |
| Transparency | D |  | D |  | D |  | D |  | B |  |
| Concentration of NaOH (mM) | 850 |  | 875 |  | 900 |  | 925 |  | 950 |  |
| C200P100Ca200Cl400 | 6.08 | 189 | 6.27 | 150 | 6.79 | 119 | 8.05 | 51.3 | 11 | 18.4 |
| Transparency | D |  | D |  | A |  | A |  | A |  |
| Concentration of NaOH (mM) | 550 |  | 575 |  | 600 |  | 625 |  | 650 |  |
| C100P100Ca200Cl400 | 5.77 | 721 | 5.96 | 841 | 6.59 | 403 | 8.11 | 154 | 11.17 | 40.9 |
| Transparency | D |  | D |  | A |  | A |  | A |  |
| Concentration of NaOH (mM) | 400 |  | 425 |  | 450 |  | 475 |  | 500 |  |
| C50P100Ca200Cl400 | 5.37 | 10900 | 5.92 | 4510 | 8.65 | 3120 | 9.75 | 922 | 11.64 | 168 |
| Transparency | D |  | D |  | D |  | A |  | B |  |

TABLE 25-continued

| Before AC | pH | Ca (μM) | pH | Ca (μM) | pH | Ca (μM) |
|---|---|---|---|---|---|---|
| Concentration of NaOH (mM) | 1525 | | 1550 | | 1575 | |
| C400P100Ca200Cl400 | 8.01 | 17.1 | 10.74 | 7.32 | 11.85 | 4.79 |
| Transparency | A | | A | | A | |
| Concentration of NaOH (mM) | 975 | | 1000 | | 1025 | |
| C200P100Ca200Cl400 | 11.99 | 9.64 | 12.3 | 5.66 | 12.45 | 5.94 |
| Transparency | A | | A | | A | |
| Concentration of NaOH (mM) | 675 | | 700 | | 725 | |
| C100P100Ca200Cl400 | 11.95 | 18.4 | 12.26 | 10.4 | 12.45 | 9.11 |
| Transparency | A | | A | | B | |
| Concentration of NaOH (mM) | 525 | | 550 | | 575 | |
| C50P100Ca200Cl400 | 12.16 | 38.9 | 12.41 | 19.2 | 12.58 | 16.6 |
| Transparency | B | | B | | B | |

| Before AC | | | | Absorbance value | | | | |
|---|---|---|---|---|---|---|---|---|
| Concentration of NaOH (mM) | 1400 | 1425 | 1450 | 1475 | 1500 | 1525 | 1550 | 1575 |
| C400P100Ca200Cl400 | 2.178 | 2.077 | 1.951 | 1.465 | 0.161 | 0.017 | 0.017 | 0.015 |
| Transparency | D | D | D | D | B | A | A | A |
| Concentration of NaOH (mM) | 850 | 875 | 900 | 925 | 950 | 975 | 1000 | 1025 |
| C200P100Ca200Cl400 | 2.073 | 1.427 | 0.063 | 0.027 | 0.027 | 0.034 | 0.041 | 0.038 |
| Transparency | D | D | A | A | A | A | A | A |
| Concentration of NaOH (mM) | 550 | 575 | 600 | 625 | 650 | 675 | 700 | 725 |
| C100P100Ca200Cl400 | 0.816 | 0.08 | 0.031 | 0.041 | 0.056 | 0.061 | 0.072 | 0.1 |
| Transparency | D | D | A | A | A | A | A | B |
| Concentration of NaOH (mM) | 400 | 425 | 450 | 475 | 500 | 525 | 550 | 575 |
| C50P100Ca200C400 | 1.597 | 0.718 | 0.486 | 0.074 | 0.113 | 0.113 | 0.165 | 0.208 |
| Transparency | D | D | D | A | B | B | B | B |

TABLE 26

| After AC | pH | Ca (μM) | pH | Ca (μM) | pH | Ca (μM) | pH | Ca (μM) | pH | Ca (μM) |
|---|---|---|---|---|---|---|---|---|---|---|
| Concentration of NaOH (mM) | 1400 | | 1425 | | 1450 | | 1475 | | 1500 | |
| C400P100Ca200Cl400 | 6 | 43 | 6.09 | 37.1 | 6.14 | 52 | 6.49 | 32.4 | 6.82 | 29.6 |
| Transparency | D | | D | | D | | D | | A | |
| Concentration of NaOH (mM) | 850 | | 875 | | 900 | | 925 | | 950 | |
| C200P100Ca200Cl400 | 5.82 | 293 | 6.1 | 164 | 6.67 | 116 | 7.84 | 53 | 10.95 | 17 |
| Transparency | D | | D | | B | | A | | A | |
| Concentration of NaOH (mM) | 550 | | 575 | | 600 | | 625 | | 650 | |
| C100P100Ca200Cl400 | 6.27 | 922 | 6.69 | 978 | 7.42 | 451 | 9.68 | 175 | 11.32 | 44.3 |
| Transparency | D | | D | | D | | A | | B | |
| Concentration of NaOH (mM) | 400 | | 425 | | 450 | | 475 | | 500 | |
| C50P100Ca200Cl400 | 4.63 | 14400 | 5.03 | 6130 | 5.75 | 3450 | 7 | 1050 | 9.84 | 191 |
| Transparency | D | | D | | D | | B | | B | |

| After AC | pH | Ca (μM) | pH | Ca (μM) | pH | Ca (μM) |
|---|---|---|---|---|---|---|
| Concentration of NaOH (mM) | 1525 | | 1550 | | 1575 | |
| C400P100Ca200Cl400 | 7.92 | 16.1 | 10.21 | 7.68 | 11.73 | 4.33 |
| Transparency | A | | A | | A | |
| Concentration of NaOH (mM) | 975 | | 1000 | | 1025 | |
| C200P100Ca200Cl400 | 11.91 | 7.79 | 12.41 | 3.53 | 12.25 | 3.82 |
| Transparency | A | | A | | A | |
| Concentration of NaOH (mM) | 675 | | 700 | | 725 | |
| C100P100Ca200Cl400 | 12.03 | 16.4 | 12.51 | 7.81 | 12.78 | 5.71 |
| Transparency | A | | A | | B | |
| Concentration of NaOH (mM) | 525 | | 550 | | 575 | |
| C50P100Ca200Cl400 | 11.86 | 33.3 | 12.21 | 13.3 | 12.45 | 9.08 |
| Transparency | B | | B | | B | |

| After AC | | | | Absorbance value | | | | |
|---|---|---|---|---|---|---|---|---|
| Concentration of NaOH (mM) | 1400 | 1425 | 1450 | 1475 | 1500 | 1525 | 1550 | 1575 |
| C400P100Ca200Cl400 | 2.112 | 2.005 | 1.374 | 0.966 | 0.035 | 0.031 | 0.042 | 0.06 |
| Transparency | D | D | D | D | A | A | A | A |
| Concentration of NaOH (mM) | 850 | 875 | 900 | 925 | 950 | 975 | 1000 | 1025 |
| C200P100Ca200Cl400 | 1.616 | 1.408 | 0.085 | 0.047 | 0.065 | 0.076 | 0.075 | 0.076 |
| Transparency | D | B | A | A | A | A | A | A |
| Concentration of NaOH (mM) | 550 | 575 | 600 | 625 | 650 | 675 | 700 | 725 |

TABLE 26-continued

| | | | | | | | | |
|---|---|---|---|---|---|---|---|---|
| C100P100Ca200Cl400 | 0.766 | 0.127 | 0.066 | 0.073 | 0.103 | 0.094 | 0.092 | 0.101 |
| Transparency | D | D | D | A | B | A | A | B |
| Concentration of NaOH (mM) | 400 | 425 | 450 | 475 | 500 | 525 | 550 | 575 |
| C50P100Ca200C400 | 1.491 | 0.75 | 0.569 | 0.122 | 0.181 | 0.144 | 0.155 | 0.18 |
| Transparency | D | D | D | B | B | B | B | B |

A large difference in transparency before and after autoclave was not observed. Thus, it was suggested that the autoclave did not have much influence on the stability of the aqueous preparation of calcium.

Example 17

Test for Confirming Solubility Rate

A test for confirming the solubility of the solid preparation of calcium in water was performed.

Fifty mL of DW in a 100 mL beaker was stirred at 300 rpm using a stirrer (Three-One Motor BL300), Impeller (Propeller R). Calcium lactate, calcium gluconate, calcium chloride, and freeze-dry powder of a C100P100Ca200K225 solution were added to the beaker so as to have a calcium concentration of 50 mM. The mixture was measured until it became transparent. The results are shown in Table 27 below.

TABLE 27

| | Dissolution time (sec.) | Average (sec.) |
|---|---|---|
| Calcium lactate-dihydrate-1 | 228 | 233.7 |
| Calcium lactate-dihydrate-2 | 233 | |
| Calcium lactate-dihydrate-3 | 240 | |
| Calcium gluconate-1 | 433 | 446.7 |
| Calcium gluconate-2 | 457 | |
| Calcium gluconate-3 | 450 | |
| C100P100Ca200K225FD Powder-1 | 8 | 10.0 |
| C100P100Ca200K225FD Powder-2 | 10 | |
| C100P100Ca200K225FD Powder-3 | 12 | |
| C200P100Ca200K550FD Powder-1 | 56 | 60.7 |
| C200P100Ca200K550FD Powder-2 | 62 | |
| C200P100Ca200K550FD Powder-3 | 64 | |
| C100P100Ca200Na200FD Powder-1 | 25 | 23.0 |
| C100P100Ca200Na200FD Powder-2 | 22 | |
| C100P100Ca200Na200FD Powder-3 | 22 | |

TABLE 27-continued

| | Dissolution time (sec.) | Average (sec.) |
|---|---|---|
| C100P100Ca200K225Na10F10FD Powder-1 | 12 | 13.3 |
| C100P100Ca200K225Na10F10FD Powder-2 | 13 | |
| C100P100Ca200K225Na10F10FD Powder-3 | 15 | |
| C200P200Ca400K450FD Powder-1 | 18 | 20.0 |
| C200P200Ca400K450FD Powder-2 | 20 | |
| C200P200Ca400K450FD Powder-3 | 22 | |
| C100P100Ca133Mg66K190FD Powder-1 | 89 | 99.7 |
| C100P100Ca133Mg66K190FD Powder-2 | 110 | |
| C100P100Ca133Mg66K190FD Powder-3 | 100 | |
| C100P100Ca133Mg66Na170FD Powder-1 | 100 | 96.0 |
| C100P100Ca133Mg66Na170FD Powder-2 | 88 | |
| C100P100Ca133Mg66Na170FD Powder-3 | 100 | |

From the results shown in Table 27, it was confirmed that the solid preparation of calcium of the present invention was even more easily dissolved in water as compared to other calcium materials which were said to have high solubility.

Example 19

Test for Adding Magnesium

Magnesium is an important mineral to maintain the health of bones, similarly to calcium. It is said that calcium and magnesium are desirably consumed at a ratio of 2:1.

A test for preparing the aqueous preparation of calcium of the present invention using magnesium in addition to calcium was performed.

The composition of 50 mM citric acid, 50 mM phosphoric acid, and 100 mM calcium was fixed, and a test for simultaneously adding 25 to 200 mM of magnesium together with calcium was performed. In the present test, calcium chloride as the calcium source, magnesium chloride as the magnesium source, and sodium hydroxide as the pH adjusting liquid were used. The results are shown in Table 28 below.

TABLE 28

| | pH | Ca (µM) | pH | Ca (µM) | pH | Ca (µM) | pH | Ca (µM) | pH | Ca (µM) |
|---|---|---|---|---|---|---|---|---|---|---|
| Concentration of Ca:Mg:Cl (mM) | Ca100Mg0Cl200 | | Ca100Mg25Cl250 | | Ca100Mg50Cl300 | | Ca100Mg100Cl400 | | Ca100Mg200Cl600 | |
| C50P50NaOH250 | 5.41 | 1300 | 4.88 | 2970 | 4.69 | 7740 | 4.51 | 15200 | 4.45 | 22200 |
| Transparency | D | | D | | D | | D | | D | |
| C50P50NaOH275 | 5.86 | 960 | 5.67 | 2170 | 5.24 | 3620 | 5.04 | 7900 | 5.17 | 14600 |
| Transparency | D | | D | | D | | D | | D | |
| C50P50NaOH300 | 6.47 | 446 | 6.74 | 1510 | 7.1 | 2670 | 6.96 | 6280 | 6.78 | 15400 |
| Transparency | A | | D | | D | | D | | D | |
| C50P50NaOH325 | 9.9 | 61.7 | 10.21 | 413 | 9.49 | 1950 | 8.98 | 7620 | 8.61 | 18000 |
| Transparency | A | | D | | D | | D | | D | |
| C50P50NaOH350 | 11.87 | 11.3 | 11.23 | 198 | 10.46 | 1050 | 9.51 | 5860 | 9.09 | 17600 |
| Transparency | B | | D | | D | | D | | D | |
| Absorbance value | | | | | | | | | | |
| Concentration of Ca:Mg:Cl (mM) | Ca100Mg0Cl200 | | Ca100Mg25Cl250 | | Ca100Mg50Cl300 | | Ca100Mg100Cl400 | | Ca100Mg200Cl600 | |
| C50P50NaOH250 | 1.73 | | 1.83 | | 1.02 | | 1.11 | | 0.91 | |
| Transparency | D | | D | | D | | D | | D | |
| C50P50NaOH275 | 0.15 | | 0.47 | | 1.07 | | 0.83 | | 0.79 | |

TABLE 28-continued

| | | | | | |
|---|---|---|---|---|---|
| Transparency | D | D | D | D | D |
| C50P50NaOH300 | 0.01 | 0.43 | 0.80 | 0.74 | 0.67 |
| Transparency | A | D | D | D | D |
| C50P50NaOH325 | 0.57 | 0.87 | 0.97 | 1.06 | 0.95 |
| Transparency | A | D | D | D | D |
| C50P50NaOH350 | 0.11 | 0.94 | 1.01 | 1.12 | 0.96 |
| Transparency | B | D | D | D | D |

Under the present conditions, a transparent colloidal solution was not obtained regardless of the additive amount of magnesium and pH.

On the other hand, the composition of 200 mM citric acid, 50 mM phosphoric acid, and 100 mM calcium was fixed, and a test for simultaneously adding 25 to 200 mM of magnesium together with calcium was performed. The results are shown in Table 29 below.

to 50 mM and the pH was in the range of 7.24 to 11.78. From this result, it was found that the solubilization range was widened by increasing the concentration of citric acid from 50 mM to 200 mM.

Subsequently, the composition of 50 mM citric acid and 50 mM phosphoric acid was fixed, and calcium was substituted by magnesium so that the total amount of calcium and mag-

TABLE 29

| | pH | Ca (μM) | pH | Ca (μM) | pH | Ca (μM) | pH | Ca (μM) | pH | Ca (μM) |
|---|---|---|---|---|---|---|---|---|---|---|
| Concentration of Ca:Mg:Cl (mM) | Ca100Mg0Cl200 | | Ca100Mg25Cl250 | | Ca100Mg50Cl300 | | Ca100Mg100Cl400 | | Ca100Mg200Cl600 | |
| C200P50NaOH650 | 5.84 | 192 | 5.76 | 251 | 5.7 | 288 | 5.5 | 322 | 4.91 | 817 |
| Transparency | D | | D | | D | | D | | D | |
| C200P50NaOH700 | 6.19 | 134 | 6.22 | 199 | 5.99 | 262 | 5.96 | 277 | 6.22 | 543 |
| Transparency | D | | D | | D | | D | | D | |
| C200P50NaOH750 | 6.92 | 74.4 | 7.1 | 159 | 7.24 | 104 | 7.57 | 264 | 7.46 | 420 |
| Transparency | A | | A | | B | | D | | D | |
| C200P50NaOH800 | 11.91 | 7.12 | 10.85 | 19.9 | 10.47 | 60.3 | 9.59 | 188 | 9 | 379 |
| Transparency | A | | B | | D | | D | | D | |
| C200P50NaOH850 | 12.52 | 3.4 | 12.12 | 7.34 | 11.78 | 12.5 | 10.43 | 101 | 9.29 | 440 |
| Transparency | A | | D | | B | | D | | D | |

| | Absorbance value | | | | |
|---|---|---|---|---|---|
| Concentration of Ca:Mg:Cl (mM) | Ca100Mg0Cl200 | Ca100Mg25Cl250 | Ca100Mg50Cl300 | Ca100Mg100Cl400 | Ca100Mg200Cl600 |
| C200P50NaOH650 | 1.54 | 1.73 | 1.67 | 1.81 | 1.05 |
| Transparency | D | D | D | D | D |
| C200P50NaOH700 | 1.70 | 1.80 | 1.01 | 1.54 | 1.70 |
| Transparency | D | D | D | D | D |
| C200P50NaOH750 | 0.02 | 0.07 | 0.17 | 0.56 | 1.95 |
| Transparency | A | A | B | D | D |
| C200P50NaOH800 | 0.02 | 0.09 | 0.66 | 0.60 | 0.61 |
| Transparency | A | B | D | D | D |
| C200P50NaOH850 | 0.03 | 0.56 | 0.13 | 0.54 | 0.58 |
| Transparency | A | D | B | D | D |

Under the present conditions, a transparent colloidal solution could be obtained when the additive amount of Mg was 0 nesium was 100 mM. Then, the test was performed. The results are shown in Table 30 below.

TABLE 30

| | pH | Ca (μM) | pH | Ca (μM) | pH | Ca (μM) | pH | Ca (μM) | pH | Ca (μM) |
|---|---|---|---|---|---|---|---|---|---|---|
| Concentration of Ca:Mg:Cl (mM) | Ca100Mg0Cl200 | | Ca67Mg33Cl200 | | Ca50Mg50Cl200 | | Ca33Mg67Cl200 | | Ca0Mg100Cl200 | |
| C50P50NaOH250 | 5.41 | 1300 | 5.47 | 1180 | 5.35 | 1400 | 6.16 | 1140 | 6.23 | 7.65 |
| Transparency | D | | D | | D | | D | | D | |
| C50P50NaOH275 | 5.86 | 960 | 6 | 639 | 6.48 | 284 | 7.06 | 257 | 6.85 | 16.4 |
| Transparency | D | | A | | D | | D | | D | |
| C50P50NaOH300 | 6.47 | 446 | 8.3 | 162 | 8.59 | 81 | 8.66 | 42.2 | 8.53 | 4.46 |
| Transparency | A | | D | | D | | D | | D | |
| C50P50NaOH325 | 9.9 | 61.7 | 10.6 | 48.7 | 10.33 | 24.9 | 10.14 | 12.3 | 10.28 | 2.35 |
| Transparency | A | | B | | D | | D | | D | |
| C50P50NaOH350 | 11.87 | 11.3 | 11.51 | 11.3 | 11.33 | 9.8 | 10.97 | 6.15 | 10.54 | 1.79 |
| Transparency | B | | D | | D | | D | | D | |

TABLE 30-continued

| | Absorbance value | | | | |
|---|---|---|---|---|---|
| Concentration of Ca:Mg:Cl (mM) | Ca100Mg0Cl200 | Ca67Mg33Cl200 | Ca50Mg50Cl200 | Ca33Mg67Cl200 | Ca0Mg100Cl200 |
| C50P50NaOH250 | 1.76 | 0.37 | 0.47 | 0.72 | 1.08 |
| Transparency | D | D | D | D | D |
| C50P50NaOH275 | 0.15 | 0.01 | 0.39 | 0.45 | 0.31 |
| Transparency | D | A | D | D | D |
| C50P50NaOH300 | 0.01 | 0.61 | 0.59 | 0.64 | 0.29 |
| Transparency | A | D | D | D | D |
| C50P50NaOH325 | 0.06 | 0.79 | 0.81 | 0.75 | 0.79 |
| Transparency | A | D | D | D | D |
| C50P50NaOH350 | 0.11 | 0.75 | 0.67 | 0.62 | 0.57 |
| Transparency | B | D | D | D | D |

Under the present conditions, it was found that a transparent colloidal solution was obtained in the case of 275 mM NaOH, 67 mM Ca, and 33 mM Mg.

On the other hand, the composition of 200 mM citric acid and 50 mM phosphoric acid was fixed, and calcium was substituted by magnesium so that the total amount of calcium and magnesium was 100 mM. Then, the test was performed. The results are shown in Table 31 below.

100 mM, 150 mM or 200 mM. A test for simultaneously adding 25 mM, 50 mM, 100 mM, 150 mM or 200 mM of magnesium together with calcium was performed.

As result, under the present conditions, a transparent solution containing magnesium was not obtained in the case of 100 mM citric acid. However, when the additive amounts of citric acid were 150 mM and 200 mM, and the additive amounts of Mg were 25 mM and 50 mM, a transparent col-

TABLE 31

| | pH | Ca (μM) | pH | Ca (μM) | pH | Ca (μM) | pH | Ca (μM) | pH | Ca (μM) |
|---|---|---|---|---|---|---|---|---|---|---|
| Concentration of Ca:Mg:Cl (mM) | Ca100Mg0Cl200 | | Ca67Mg33Cl200 | | Ca50Mg50Cl200 | | Ca33Mg67Cl200 | | Ca0Mg100Cl200 | |
| C200P50NaOH650 | 5.84 | 192 | 5.81 | 174 | 5.79 | 265 | 5.78 | 181 | 5.82 | 13.9 |
| Transparency | D | | D | | D | | A | | A | |
| C200P50NaOH700 | 6.19 | 134 | 6.36 | 157 | 6.52 | 113 | 6.69 | 90 | 6.95 | 4.39 |
| Transparency | D | | B | | D | | D | | A | |
| C200P50NaOH750 | 6.92 | 74.4 | 8.1 | 2.93 | 9.09 | 25.4 | 9.13 | 15.5 | 8.96 | 1.96 |
| Transparency | A | | D | | D | | D | | D | |
| C200P50NaOH800 | 11.91 | 7.12 | 11.22 | 2.3 | 11.24 | 3.48 | 10.88 | 2.44 | 10.74 | 0.6 |
| Transparency | A | | D | | D | | D | | D | |
| C200P50NaOH850 | 12.52 | 3.4 | 12.19 | 0.63 | 12.23 | 0.49 | 12.12 | 0.53 | 11.47 | 0.45 |
| Transparency | A | | D | | D | | D | | D | |

| | Absorbance value | | | | |
|---|---|---|---|---|---|
| Concentration of Ca:Mg:Cl (mM) | Ca100Mg0Cl200 | Ca67Mg33Cl200 | Ca50Mg50Cl200 | Ca33Mg67Cl200 | Ca0Mg100Cl200 |
| C200P50NaOH650 | 1.54 | 1.60 | 0.01 | 0.01 | 0.01 |
| Transparency | D | D | D | A | A |
| C200P50NaOH700 | 1.70 | 0.10 | 0.71 | 0.41 | 0.00 |
| Transparency | D | B | D | D | A |
| C200P50NaOH750 | 0.02 | 0.24 | 0.35 | 0.22 | 0.30 |
| Transparency | A | D | D | D | D |
| C200P50NaOH800 | 0.02 | 0.55 | 0.40 | 0.22 | 0.52 |
| Transparency | A | D | D | D | D |
| C200P50NaOH850 | 0.03 | 0.79 | 0.56 | 0.28 | 0.06 |
| Transparency | A | D | D | D | D |

Under the present conditions, it was found that a transparent colloidal solution was obtained only in the case of 700 mM NaOH:67 mM Ca:33 mM Mg (in the case of 700 mM NaOH:33 mM Ca:67 mM Mg, 650 mM NaOH:0 mM Ca:100 mM Mg, 700 mM HaOH:0 mM Ca:100 mM Mg, the Tyndall phenomenon cannot be confirmed, and thus it is considered that it is a non-colloidal solution). Even if the concentration of citric acid was increased from 50 mM to 200 mM, a difference was hardly observed.

Further, calcium hydroxide as the calcium source, magnesium hydroxide as the magnesium source, potassium hydroxide solution as the pH adjusting liquid were used to prepare a preparation of calcium. The concentration of phosphoric acid was fixed to 100 mM and the concentration of calcium was fixed to 200 mM. The concentration of citric acid was set to loidal solution could be obtained. As with the case where calcium chloride, magnesium chloride, and sodium hydroxide were used, it was found that the range of transparency was widened by increasing the amount of citric acid.

Example 19

Production of Aqueous Preparation of Calcium Using Calcium Oxide

The aqueous preparation of calcium was prepared using calcium oxide as the calcium source. Calcium oxide in an amount of 1.12 g was suspended in 75.2 mL of distilled water. Then, 20 mL of a solution containing 500 mM of each of citric acid and phosphoric acid was added to the suspension and stirred. Here, 4.5 mL of a 5 M potassium hydroxide solution was left at 45° C. and stirred overnight. On the next day, transparent colloidal solution could be obtained. This solution contains 100 mM citric acid, 100 mM phosphoric acid, 200 mM calcium, and 225 mM potassium. The pH and calcium ion concentration of the solution after the autoclave treatment were 6.74 and 68.8 μmol/L, respectively.

Calcined shell calcium whose main component was calcium oxide was used in place of calcium oxide, other compositions were the same as those described above, and the aqueous preparation of calcium was prepared so that the total amount of the solution was 50 mL. Thus, the transparent colloidal solution could be obtained. The pH and calcium ion concentration of the solution after the autoclave treatment were 6.73 and 70.2 μmol/L, respectively.

Example 20

Measurement of Average Particle Diameter

The Tyndall phenomenon was confirmed in the aqueous preparation of calcium of the present invention.

Thus, this suggests that the preparation is a colloidal solution.

The aqueous preparation of calcium was 10000-fold diluted, which was placed in a plastic measuring cell at 25° C., and the particle diameter was measured using a Dynamic-light-scattering photometer (DLS: Particle Sizing Systems Co. NICOMP 380ZLS). As a result, it was revealed that the aqueous preparation of calcium of C100P100Ca200K225 contained colloidal particles having an average particle diameter of 5.6 nm, the aqueous preparation of calcium of C100P100Ca200K350 contained colloidal particles having an average particle diameter of 32 nm, the aqueous preparation of calcium of C100P100Ca200K400 contained colloidal particles having an average particle diameter of 29 nm, the aqueous preparation of calcium of C200P100Ca200K550 contained colloidal particles having an average particle diameter of 25.6 nm, and the aqueous preparation of calcium of C100P100Ca200K225Na10F10 contained colloidal particles having an average particle diameter of 12.8 nm.

Therefore, it is considered that the aqueous preparation of calcium contains colloidal particles of 100 nm or less as a constituent.

On the other hand, the aqueous preparation of calcium was converted to a solid preparation of calcium by freeze-drying and the solid preparation was redissolved. The redissolution solution was subjected to a DLS measurement. It was revealed that the aqueous preparation of calcium of C100P100Ca200K225 contained colloidal particles having an average particle diameter of 26.8 nm, the aqueous preparation of calcium of C100P100Ca200K350 contained colloidal particles having an average particle diameter of 40.3 nm, the aqueous preparation of calcium of C100P100Ca200K400 contained colloidal particles having an average particle diameter of 26.4 nm, the aqueous preparation of calcium of C200P100Ca200K550 contained colloidal particles having an average particle diameter of 25.5 nm, and the aqueous preparation of calcium of C100P100Ca200K225Na10F10 contained colloidal particles having an average particle diameter of 10.8 nm.

In the case of the composition of C100P100Ca200K225, although a difference (about 20 nm) in the average particle diameter was observed, it was equal to the average particle diameter of the stock solution. Thus, it was suggested that when the aqueous preparation of calcium was converted to a solid preparation of calcium by freeze-drying, colloidal particles were maintained in a state of the stock solution.

Example 21

X-Ray Crystallographic Analysis

In Order to Identify the Above Colloidal particles, X-ray diffraction (XRD) measurement and analysis were performed on the solid preparation of calcium obtained by freeze-drying the aqueous preparation of calcium. The powder leveled off and filled to the top of a fixed cell was measured using PHILIPS X'Pert Pro. In this regard, CuKα was used as the radiation source. The results of XRD measurement are shown in FIGS. 7A to 7D and FIGS. 8A to 8C.

It was revealed that, in the case of C100P100Ca200K225, C200P100Ca200K550, and C100P100Ca200K225Na10F10, the concordance rate with hydroxyapatite was high.

Even in the case of the same composition of C100P100Ca200K225, the crystallinity of the sample which was freeze-dried in a cloudy state without being aged was low. There was no candidate of the identical compound. Consequently, it was suggested that amorphous calcium phosphate was converted to colloidal particles of Hydroxyapatite during aging.

In the case of the aqueous preparation of calcium of C100P100Ca200K50 which did not become a transparent aqueous preparation of calcium even if it was aged, the concordance rate with Brushite was high. In the case of C100P100Ca200K100, Brushite, $Ca(H_2PO_4)_2$-$2H_2O$, $Ca_3(PO_3)_6$-$10H_2O$, and Hydroxyapatite were recognized as candidates. In the case of C100P100Ca200K150, Brushite, $Ca(H_2PO_4)_2$-$2H_2O$, $Ca_3(PO_3)_6$-$10H_2O$, Hydroxyapatite are listed as candidates. In the case of C100P100Ca200K150, it was revealed that as compared to the case of C100P100Ca200K100, the concordance rate with hydroxyapatite was high.

The above results suggested that amorphous calcium phosphate was converted to a crystalline calcium phosphate compound by aging, Hydroxyapatite was easily produced by increasing the pH, and colloidal particles of Hydroxyapatite with excellent dispersion stability were produced by adjusting the pH to more than a certain pH.

Example 22

Sensory Evaluation of Bitterness of Calcium Preparation

The bitterness of calcium lactate and calcium gluconate which were less bitter among calcium preparations were compared to that of the calcium preparation of the present invention and evaluated.

As the solution for dissolving the calcium preparation, a 0.5% salt solution and a 5% sucrose solution were prepared. Calcium lactate, calcium gluconate, and the calcium preparations (1) to (7) of the present invention described in Table 32 below were respectively dissolved in the salt solution and the sucrose solution at a calcium concentration of 150 mg/100 mL.

TABLE 32

| Composition | Calcium source | Citric acid source | Phosphoric acid source | Magnesium source | PH adjusting liquid |
|---|---|---|---|---|---|
| (1) C100P100Ca200K225 | Calcium hydroxide | Citric acid | Phosphoric acid | — | Potassium hydroxide |
| (2) C100P100Ca200Na200 | Calcium hydroxide | Citric acid | Phosphoric acid | — | Sodium hydroxide |
| (3) C100P100Ca134Mg66K190 | Calcium hydroxide | Citric acid | Phosphoric acid | Magnesium hydroxide | Potassium hydroxide |
| (4) C100P100Ca134Mg66Na170 | Calcium hydroxide | Citric acid | Phosphoric acid | Magnesium hydroxide | Sodium hydroxide |
| (5) C200P100Ca200K550 | Calcium hydroxide | Citric acid | Phosphoric acid | — | Potassium hydroxide |
| (6) C100P100Ca200K225 | Calcium oxide | Citric acid | Phosphoric acid | — | Potassium hydroxide |
| (7) C100P100Ca200K225 | Calcined shell calcium | Citric acid | Phosphoric acid | — | Potassium hydroxide |

The bitterness of the salt solution and the sucrose solution was defined as 1, and the bitterness of the solution obtained by dissolving calcium chloride with strong bitterness in the salt solution and the sucrose solution was defined as 5 such that the calcium concentration was the same as that of each calcium preparation. Five evaluators with training in the evaluation of taste evaluated the bitterness of each calcium preparation. The results are shown in Table 33 below.

TABLE 33

| Solvent | Evaluator | Calcium lactate | Calcium gluconate | CPCa (1) | (2) | (3) | (4) | (5) | (6) | (7) |
|---|---|---|---|---|---|---|---|---|---|---|
| 5% sucrose | A | 4 | 3 | 1 | 1 | 1 | 1 | 1 | 1 | 1 |
| | B | 3 | 1 | 1 | 1 | 1 | 1 | 2 | 1 | 1 |
| | C | 2 | 1 | 1 | 1 | 1 | 1 | 1 | 1 | 1 |
| | D | 5 | 5 | 2 | 1 | 1 | 2 | 3 | 2 | 4 |
| | E | 4 | 2 | 1 | 1 | 1 | 2 | 2 | 1 | 1 |
| | Total | 18 | 12 | 6 | 5 | 5 | 7 | 9 | 6 | 8 |
| | Average | 3.6 | 2.4 | 1.2 | 1 | 1 | 1.4 | 1.8 | 1.2 | 1.6 |
| 0.5% salt | A | 3 | 2 | 1 | 1 | 1 | 1 | 1 | 1 | 1 |
| | B | 5 | 3 | 1 | 1 | 1 | 1 | 2 | 1 | 1 |
| | C | 5 | 4 | 1 | 1 | 1 | 1 | 2 | 1 | 1 |
| | D | 5 | 5 | 2 | 2 | 1 | 2 | 3 | 2 | 3 |
| | E | 5 | 4 | 1 | 1 | 1 | 1 | 2 | 2 | 2 |
| | Total | 23 | 18 | 6 | 6 | 5 | 6 | 10 | 7 | 8 |
| | Average | 4.6 | 3.6 | 1.2 | 1.2 | 1 | 1.2 | 2 | 1.4 | 1.6 |

As shown in the Table above, the calcium preparation of the present invention was less bitter than calcium lactate and calcium gluconate. In the case of calcium lactate and calcium gluconate, particularly in a solution containing salts, a strong bitter taste is noted. On the other hand, in the case of the calcium preparation of the present invention even in a salt solution, a very slightly hitter taste is noted. Thus, it is considered that it is possible to utilize the calcium preparation of the invention for various food products.

Example 23

Dental Application

The calcium preparation of the present invention is excellent in safety and stability, and the following two advantages for acid in the mouth can be expected. Thus, it may be blended with an oral care product.

Since cavities are dissolution phenomena of apatite due to the acid produced in plaque, an effect of neutralizing the acid by the accumulation of the calcium preparation of the present invention in the plaque and inhibiting the dental decalcification can be desired as one of the advantages, if the calcium preparation of the present invention has a buffering effect on acid.

The other advantage is as follows. When the calcium preparation of the present invention is degraded by acid, calcium ions and phosphate ions eluted from the calcium preparation of the present invention inhibit the dental decalcification. Further, when the pH returns to neutral, recalcification may be facilitated by the calcium ions and phosphate ions.

If not otherwise specified, regarding the test for dental application, C100P100Ca200K225 is abbreviated as CPCa, and C100P100Ca200K225Na10F10 is abbreviated as CPCaF. A freeze-dried powder of C100P100Ca200K225 is abbreviated as CFCa (FD), and a freeze-dried powder of C100P100Ca200K225Na10F10 is abbreviated as CPCaF (FD).

(1) Examination Regarding Buffer Capacity and Releasing Capacity of Calcium Ions of Calcium Preparation of Present Invention The examination regarding the acid buffer capacity and releasing capacity of calcium ions of the calcium preparation of the present invention was performed.

(Method)

Distilled water, 3 mM of a sodium phosphate solution adjusted to have a pH of 7.0 (phosphoric acid concentration in the saliva), 1.09 mM of (the concentration corresponding to the concentration of citric acid in 0.05% solution of CPCa (FD) and CPCaF (FD)) or 2.18 mM of (the concentration corresponding to the concentration of citric acid in 0.1% solution of CPCa (FD) and CPCaF (FD)) a sodium citrate solution adjusted to have a pH of 7.0, and a mixed solution adjusted to have a pH of 7.0 of 3 mM of sodium phosphate and 1.09 mM or 2.18 mM of sodium citrate were prepared.

A test liquid (100 mL) was prepared by dissolving each of the solutions in 0.05% or 0.1% of CPCa (FD) or CPCaF (F9). Then, 0.1N hydrochloric acid was added thereto by 0.1 mL while stirring, and then the stabilized pH was recorded.

(Results and Consideration)

The above results are shown in FIGS. 9A to 9D. In FIGS. 9A to 9D, the black data shows pH and the white data shows the calcium ion concentration.

In FIG. 9A, (A) represents distilled water, (B) represents 0.05% of CPCa (FD), (C) represents 3 mM phosphoric acid, (9) represents a mixture of 3 mM phosphoric acid and 0.05% of CPCa (FD), (E) represents 1.09 mM citric acid, and (F) represents a mixture of 3 mM phosphoric acid and 1.09 mM citric acid.

Figure 9B:
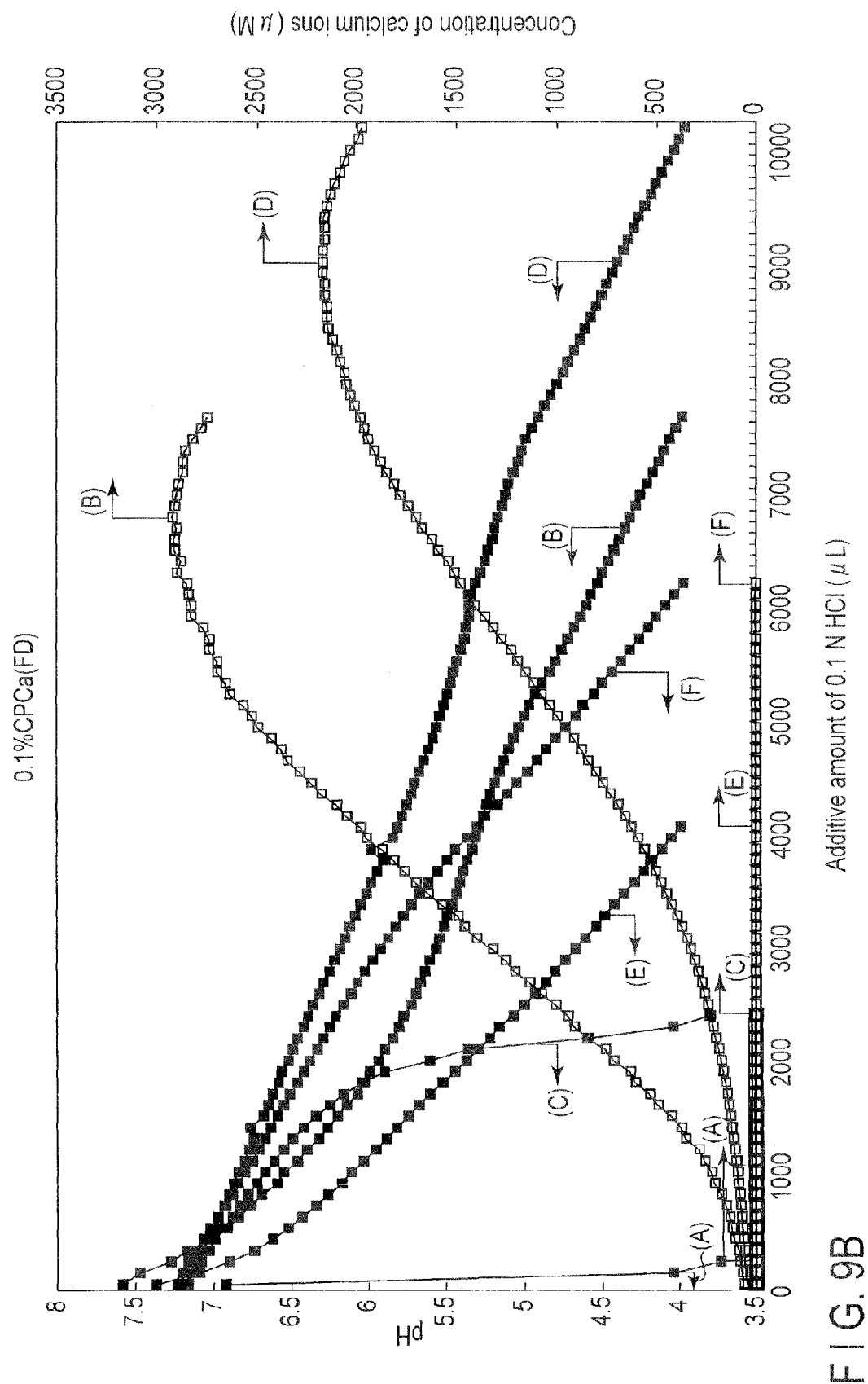
FIG. 9B is a view showing the evaluation results of the buffer capacity of the calcium preparation and the releasing capacity of calcium ions of the calcium preparation.

In FIG. 9B, (A) represents distilled water, (B) represents 0.1% of CPCa (FD), (C) represents 3 mM phosphoric acid, (D) represents a mixture of 3 mM phosphoric acid and 0.1% of CPCa (FD), (E) represents 1.09 mM citric acid, and (F) represents a mixture of 3 mM phosphoric acid and 1.09 mM citric acid.

Figure 9C:
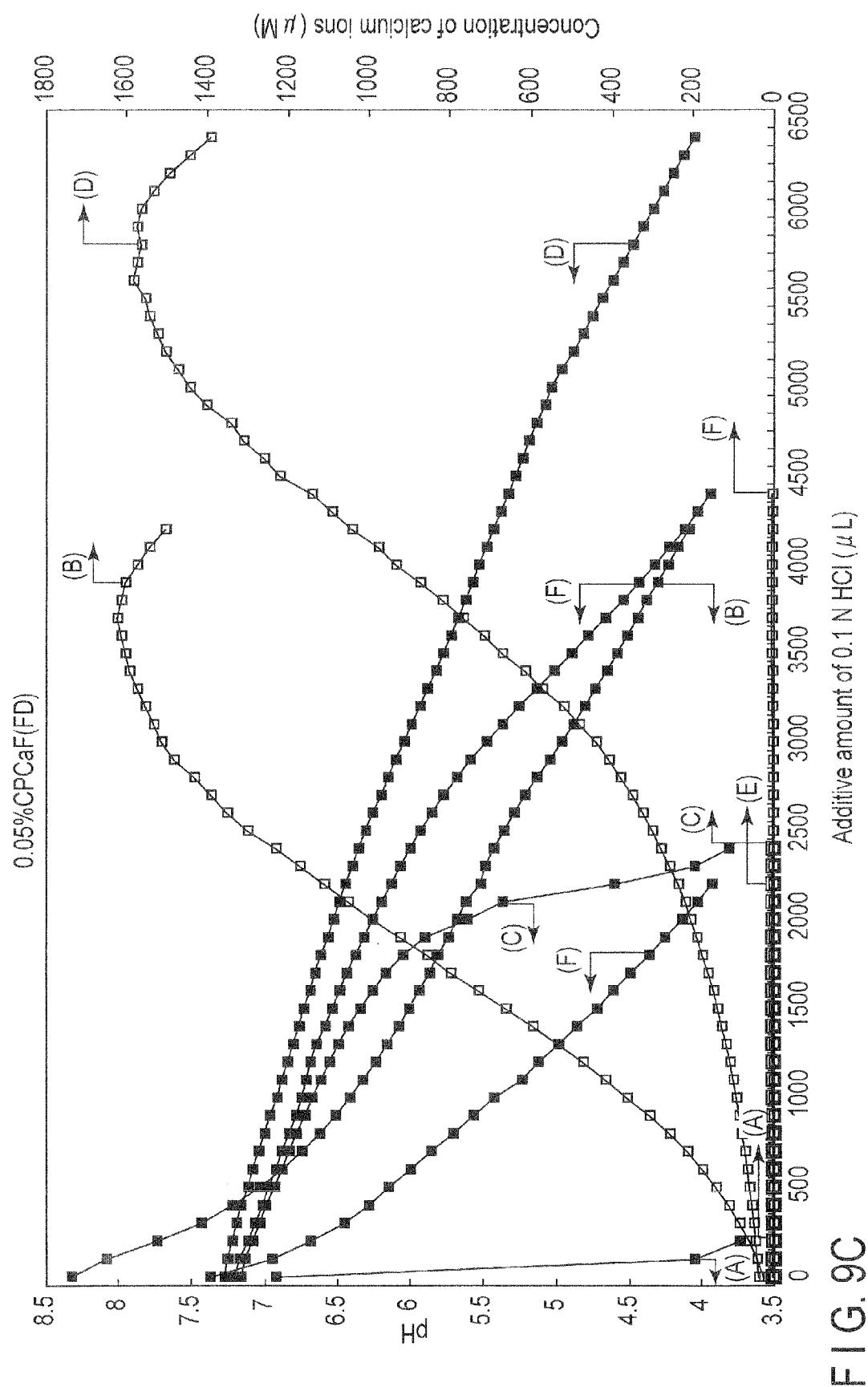
FIG. 9C is a view showing the evaluation results of the buffer capacity of the calcium preparation and the releasing capacity of calcium ions of the calcium preparation.
Figure 9D:
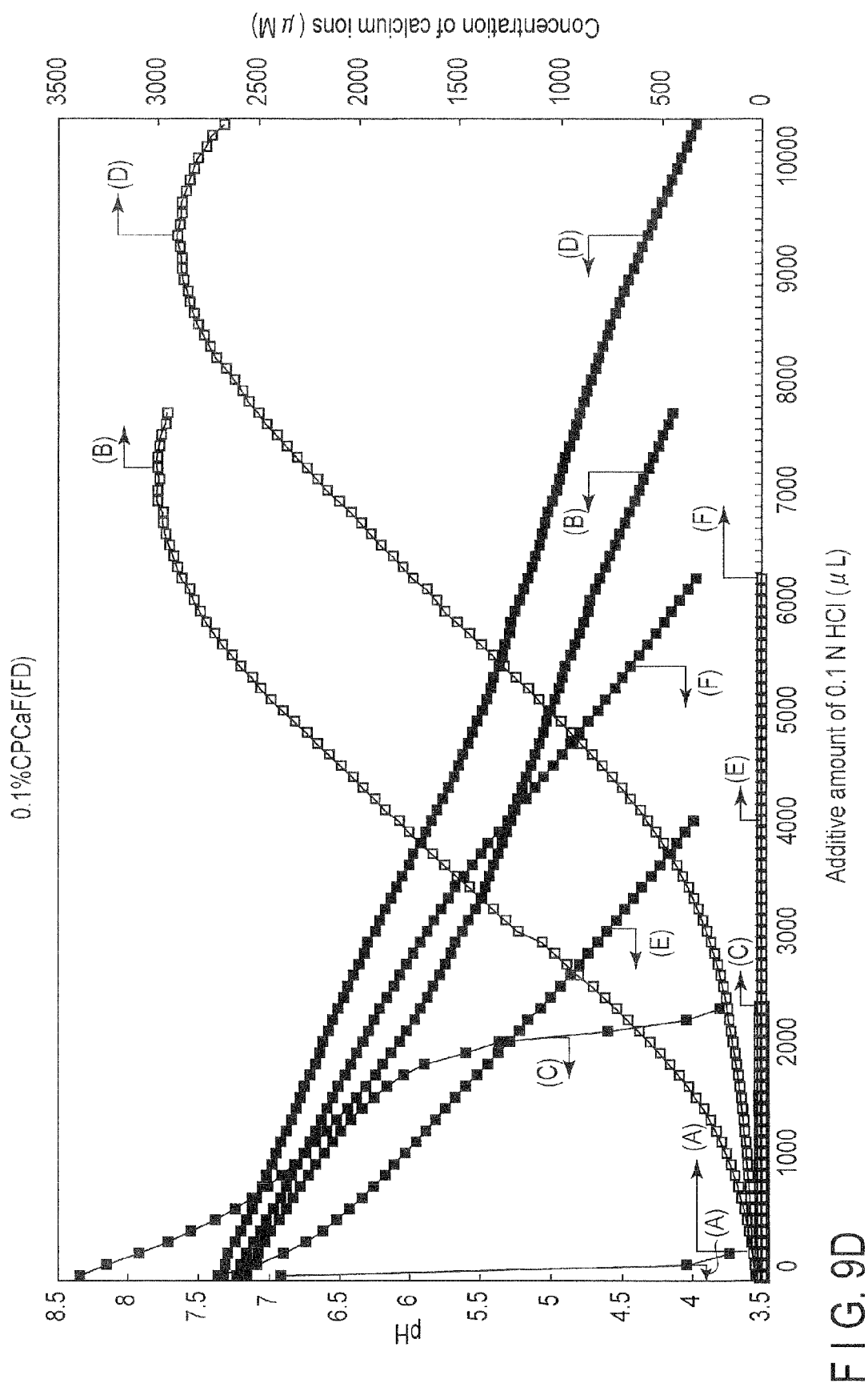
FIG. 9D is a view showing the evaluation results of the buffer capacity of the calcium preparation and the releasing capacity of calcium ions of the calcium preparation.
Figure 10A:
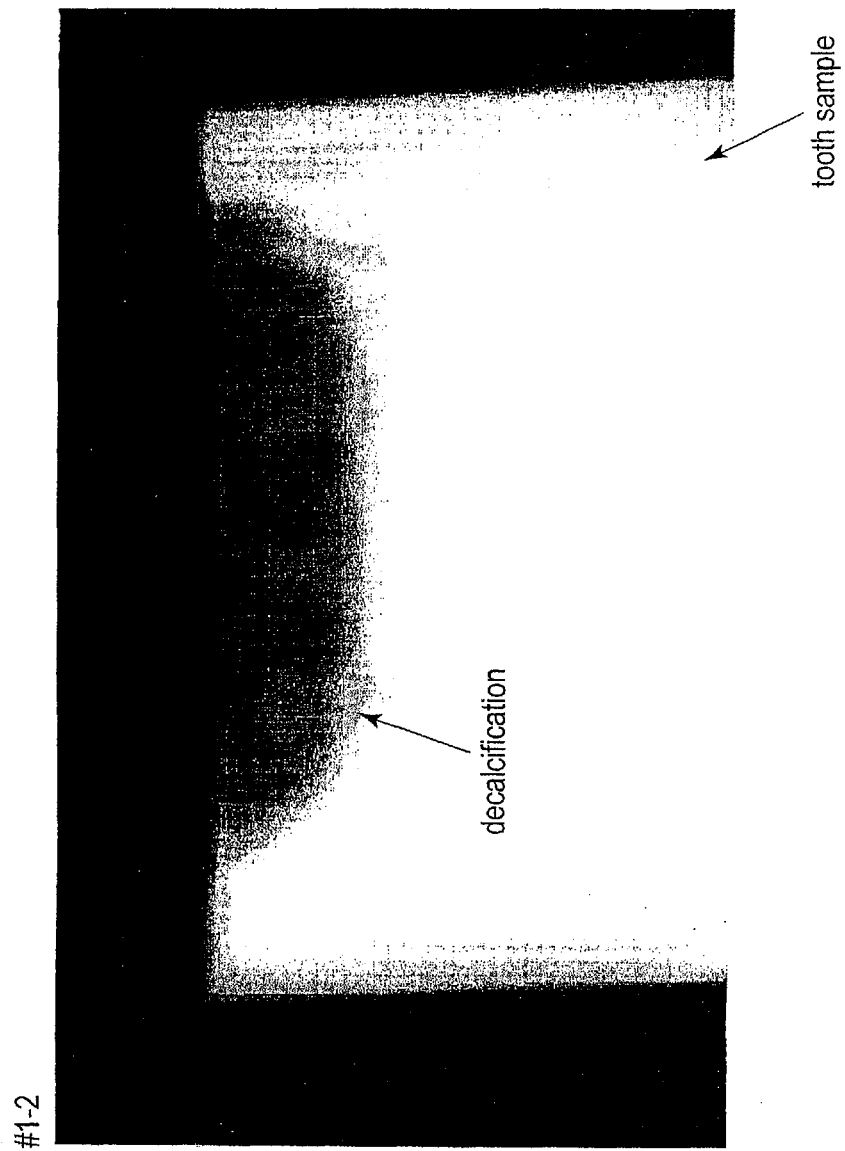
FIG. 10A is a photograph showing the evaluation results of the inhibitory effect of the calcium preparation on the decalcification of dentine.
Figure 10B:
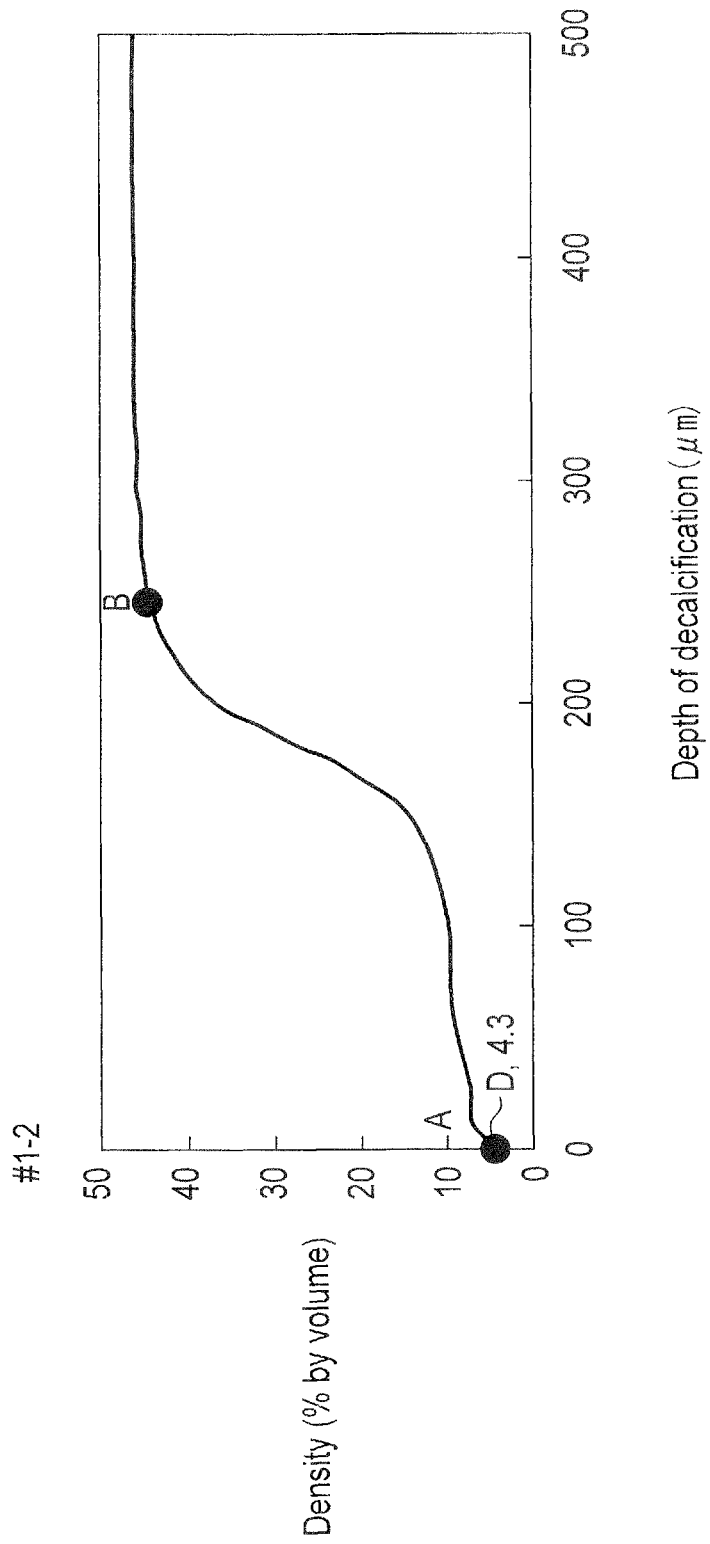
FIG. 10B is a graph showing the evaluation results of the inhibitory effect of the calcium preparation on the decalcification of dentine.
Figure 11A:
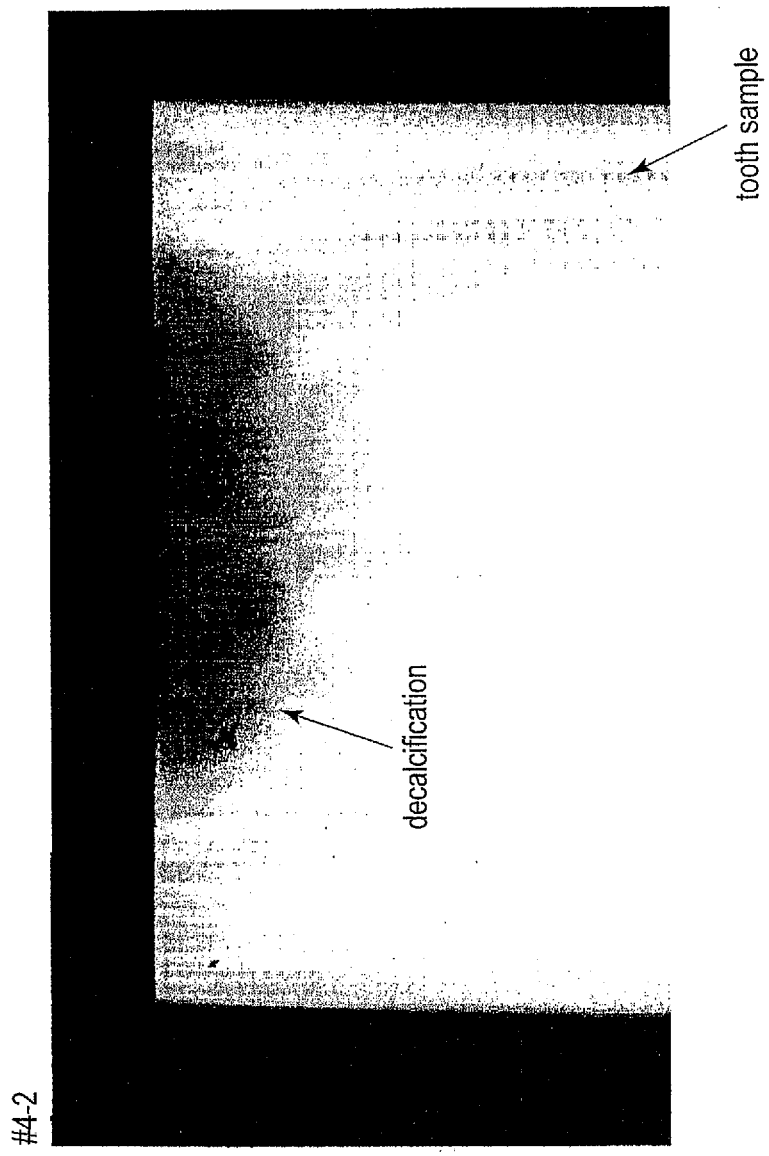
FIG. 11A is a photograph showing the evaluation results of the inhibitory effect of the calcium preparation on the decalcification of dentine.
Figure 11B:
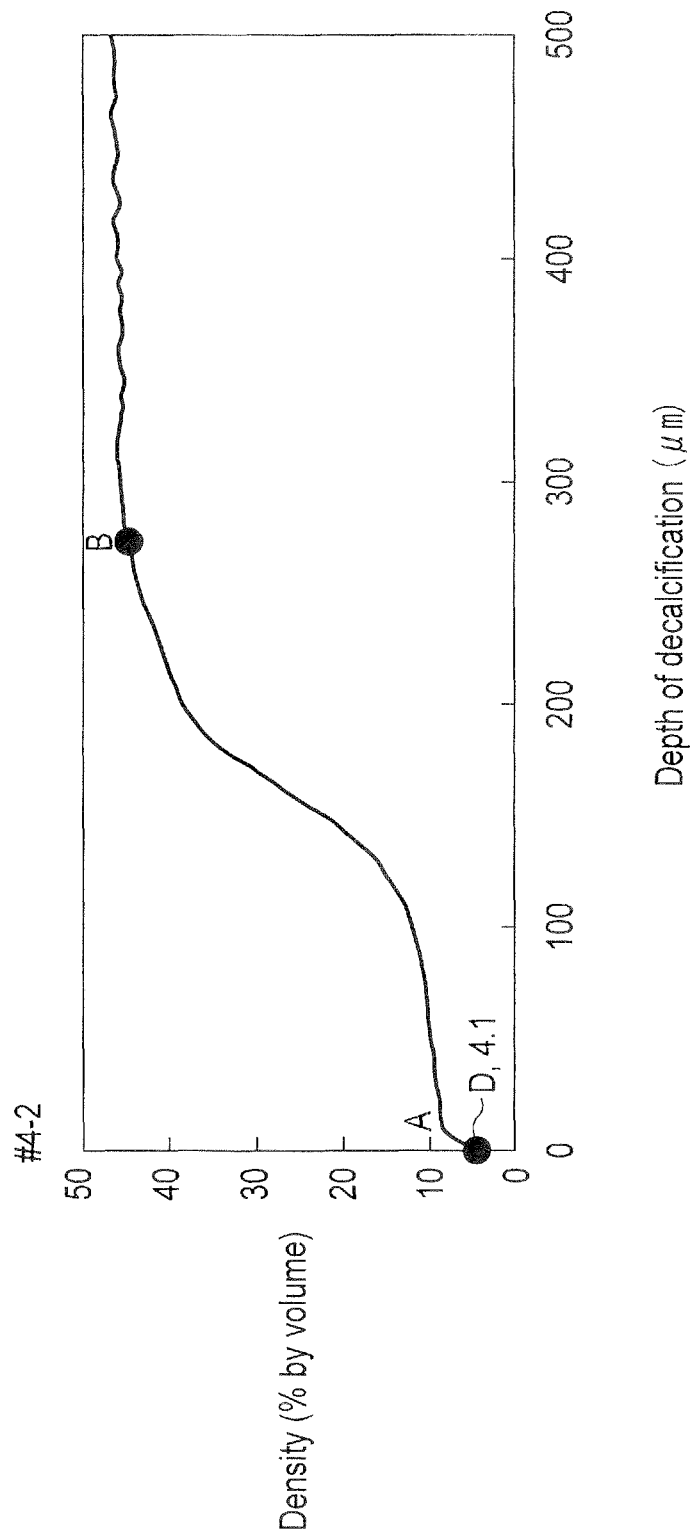
FIG. 11B is a graph showing the evaluation results of the inhibitory effect of the calcium preparation on the decalcification of dentine.
Figure 12A:
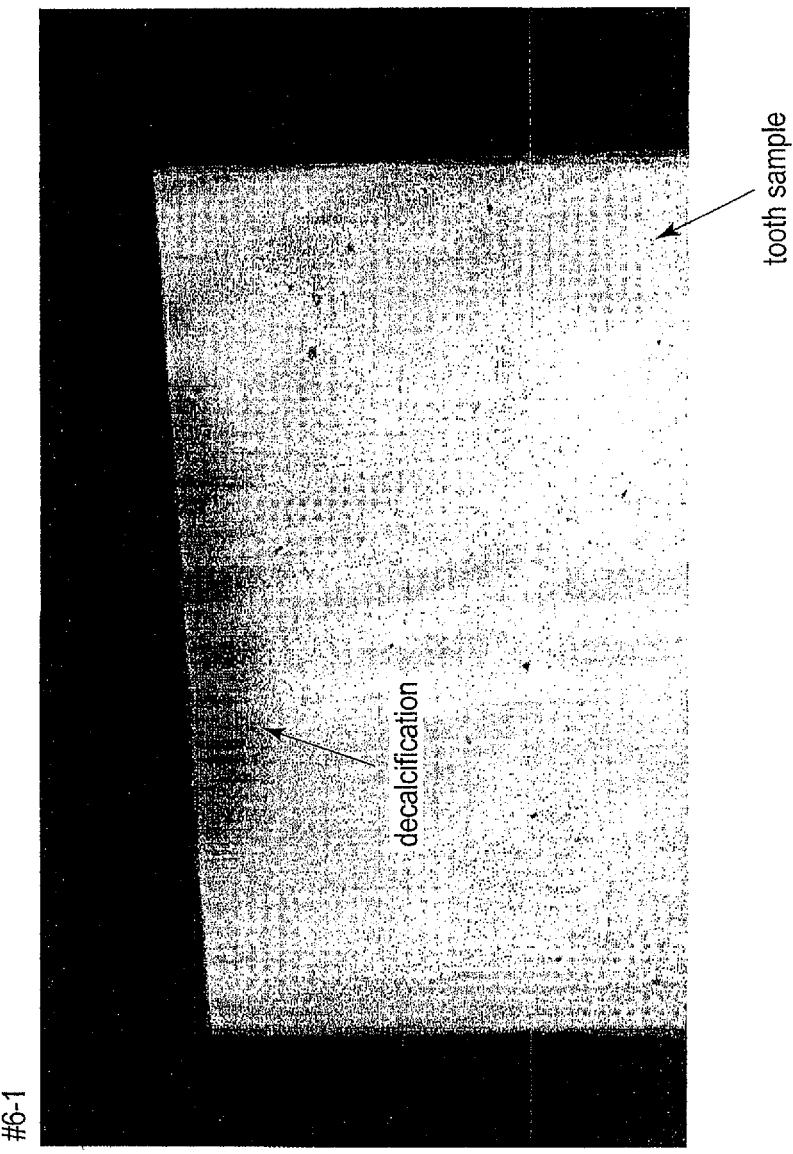
FIG. 12A is a photograph showing the evaluation results of the inhibitory effect of the calcium preparation on the decalcification of dentine.
Figure 12B:
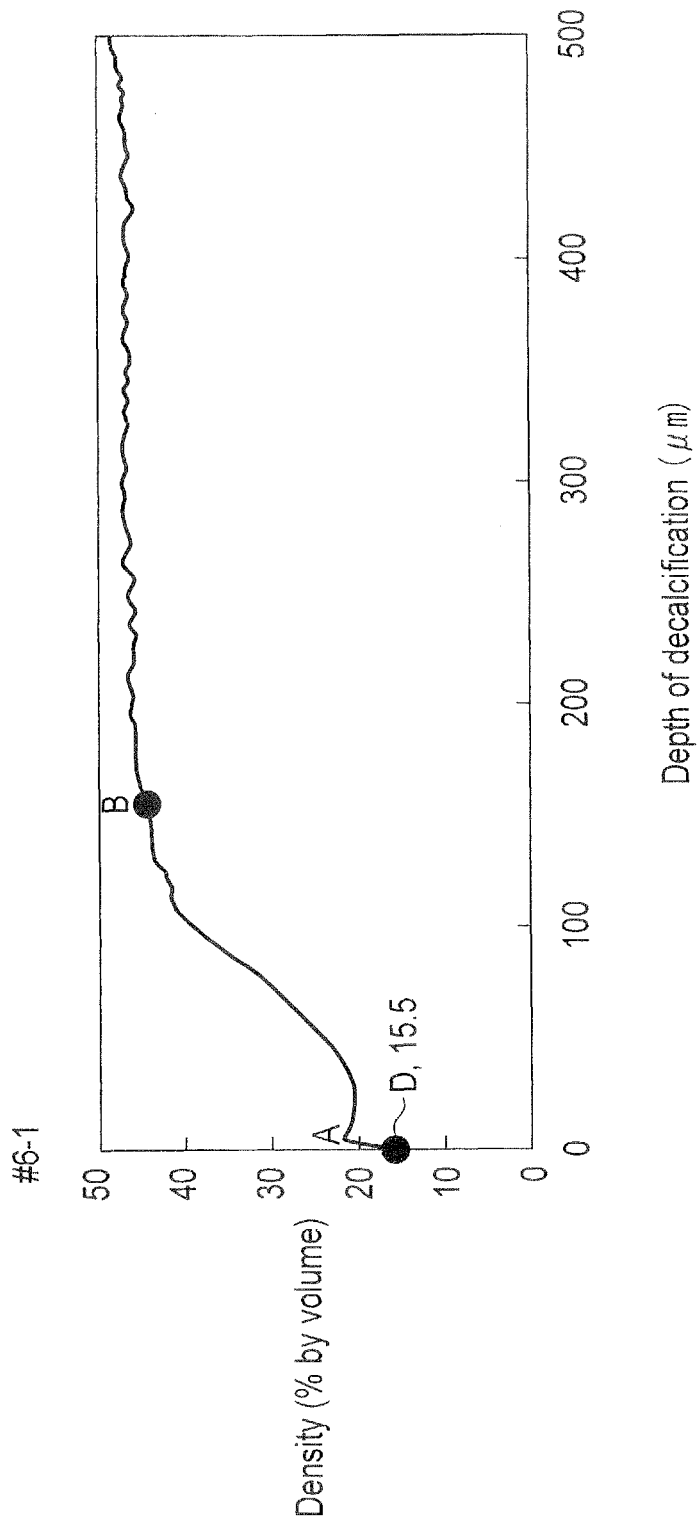
FIG. 12B is a graph showing the evaluation results of the inhibitory effect of the calcium preparation on the decalcification of dentine.
Figure 13B:
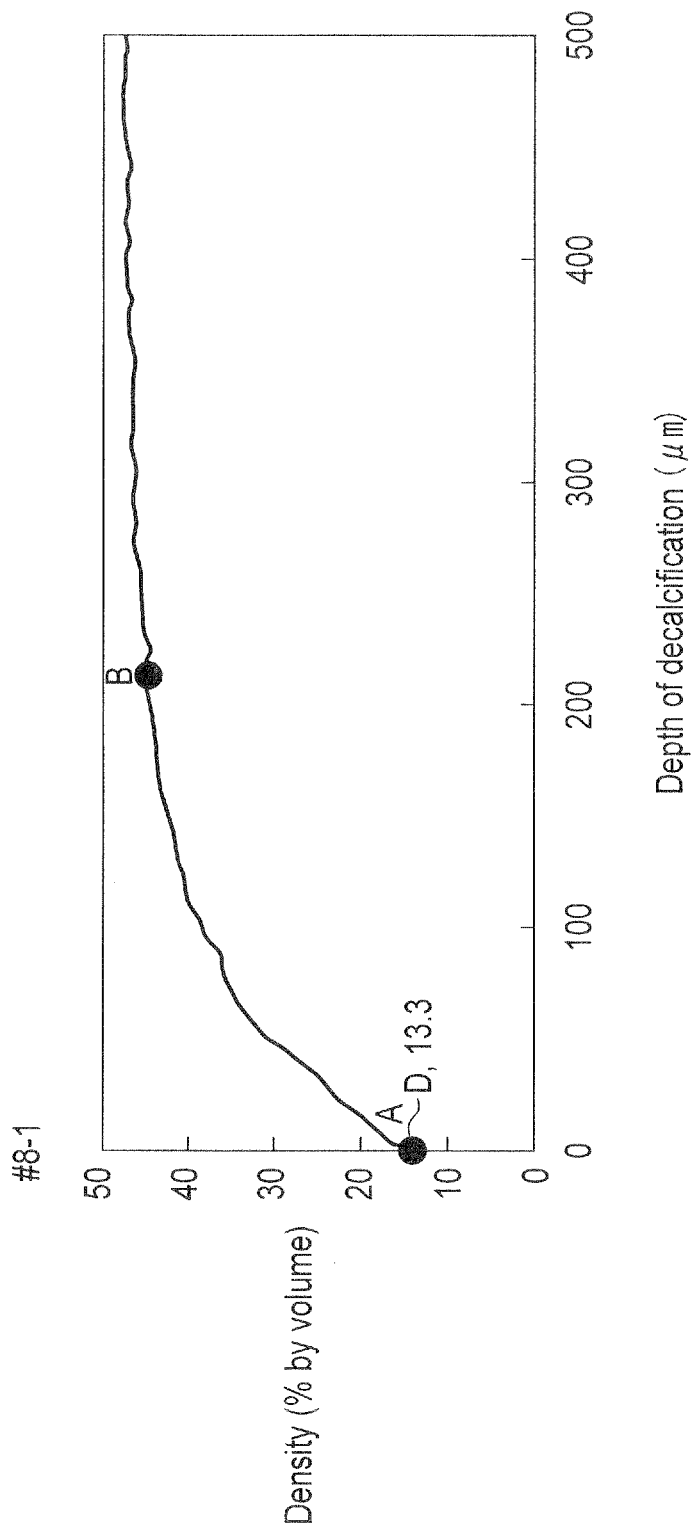
FIG. 13B is a graph showing the evaluation results of the inhibitory effect of the calcium preparation on the decalcification of dentine.
Figure 14A:
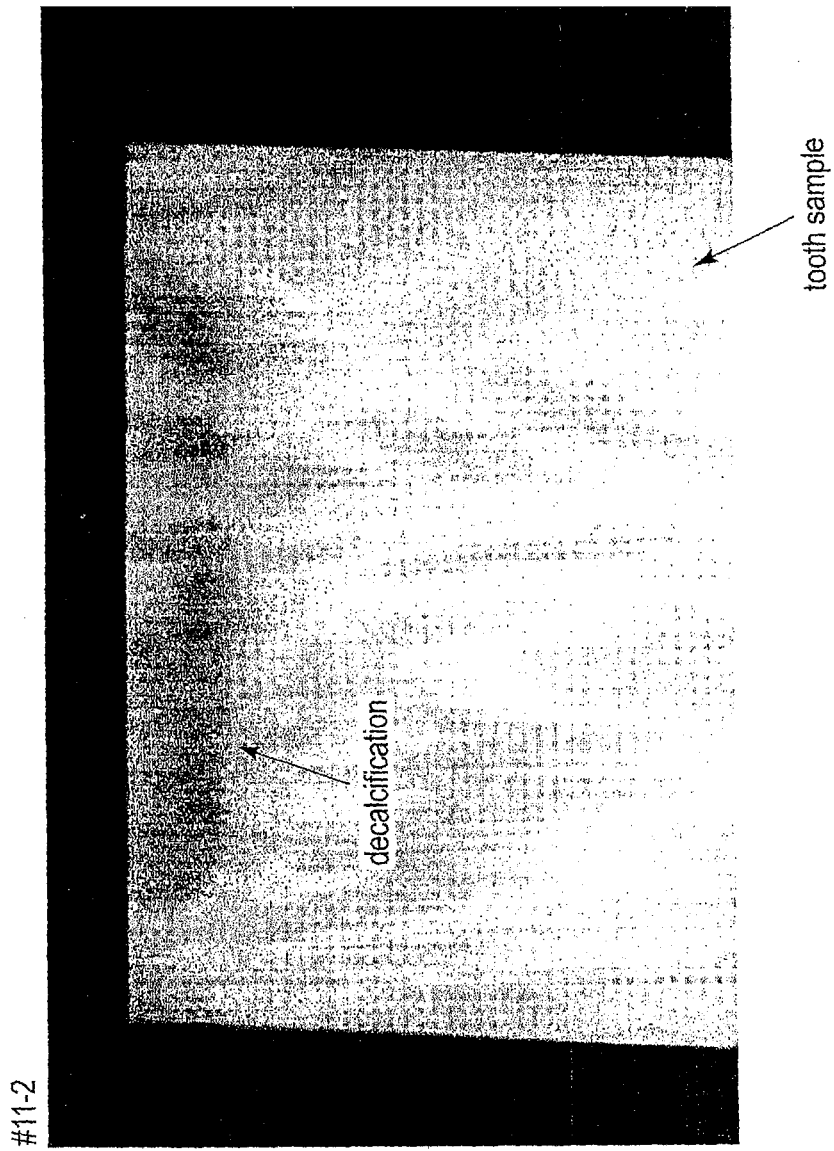
FIG. 14A is a photograph showing the evaluation results of the inhibitory effect of the calcium preparation on the decalcification of dentine.
Figure 14B:
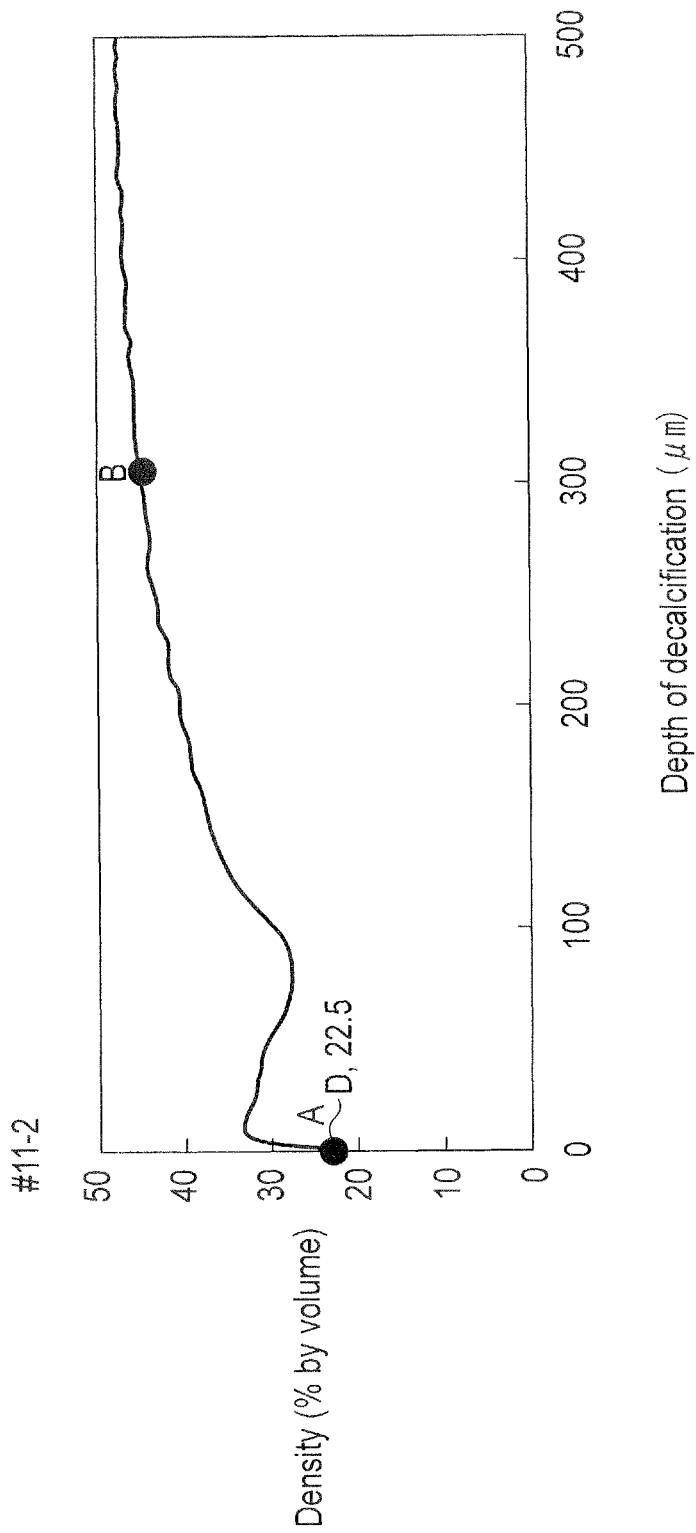
FIG. 14B is a graph showing the evaluation results of the inhibitory effect of the calcium preparation on the decalcification of dentine.
Figure 15A:
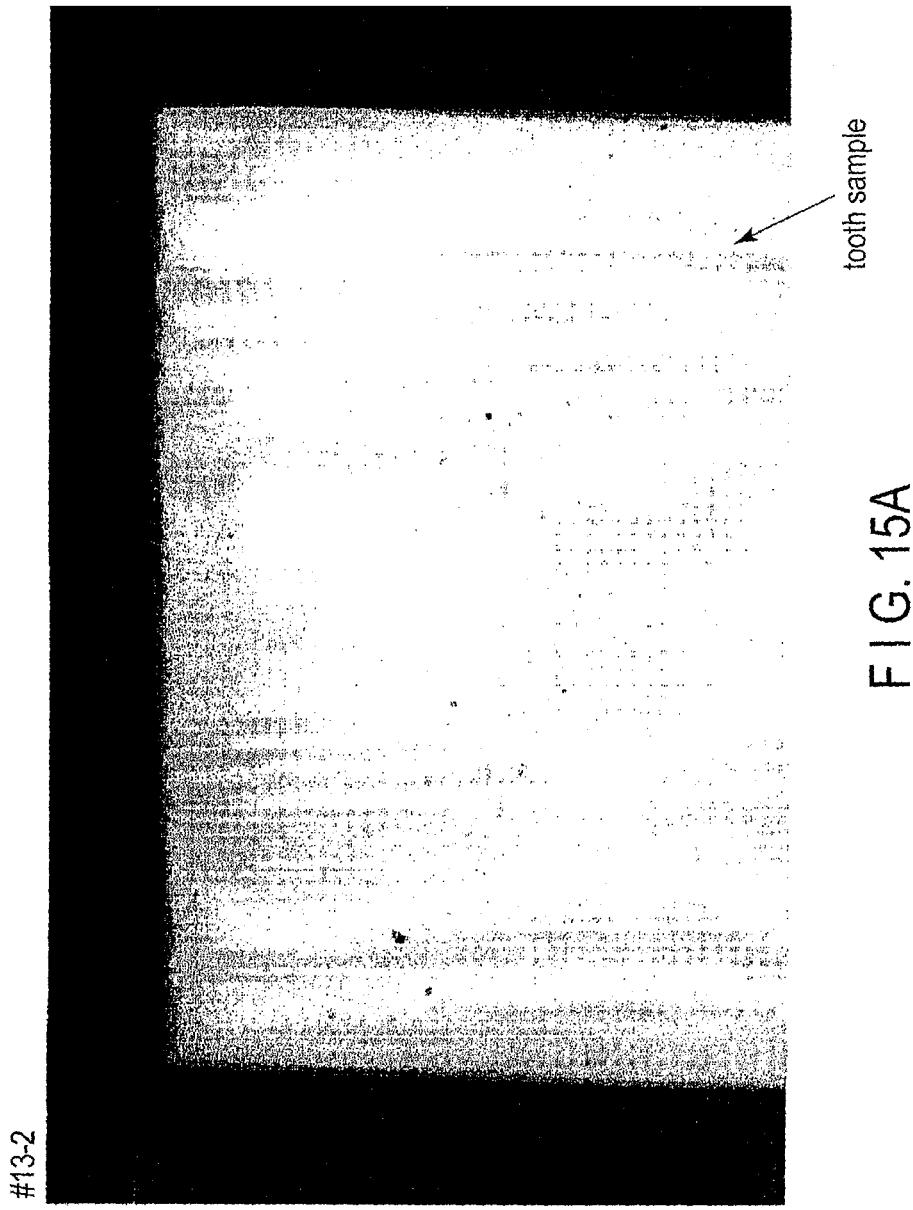
FIG. 15A is a photograph showing the evaluation results of the inhibitory effect of the calcium preparation on the decalcification of dentine.
Figure 15B:
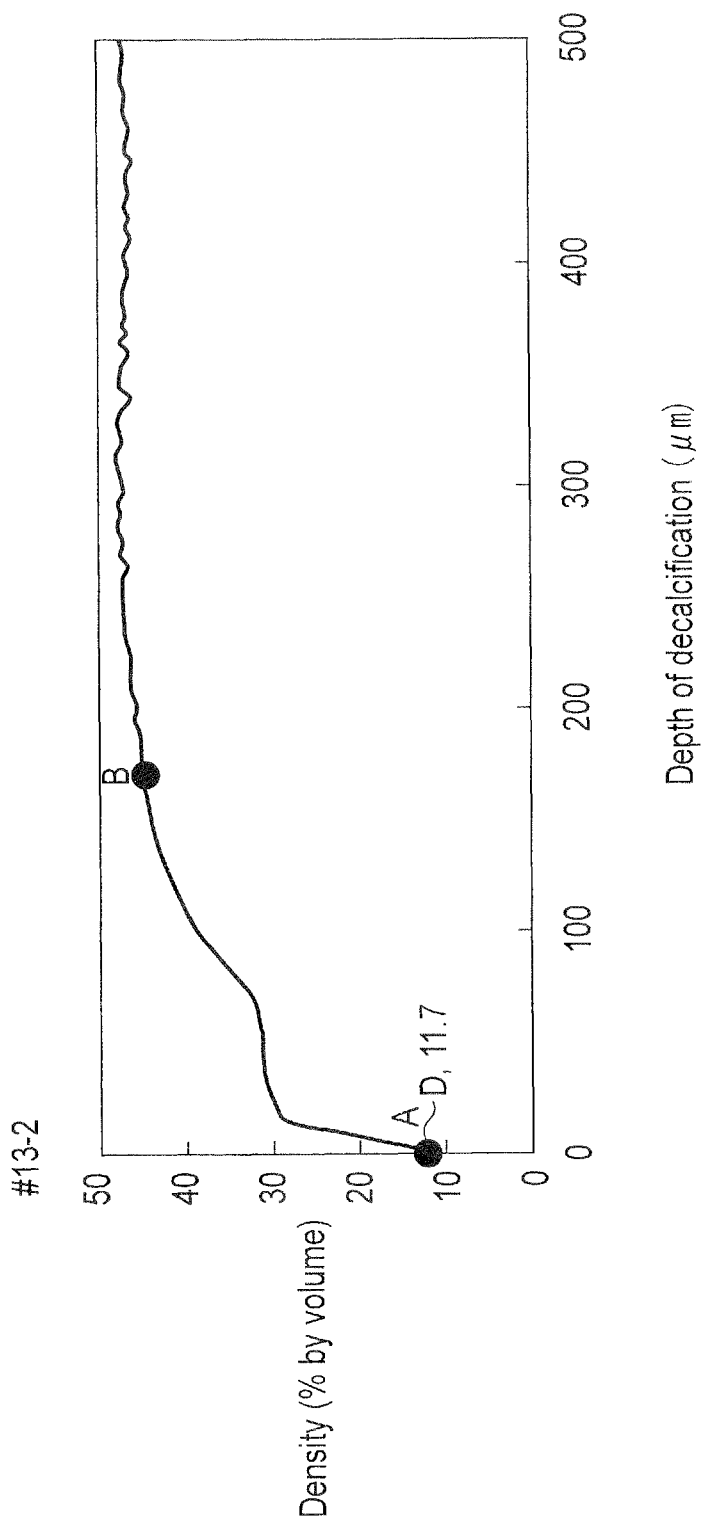
FIG. 15B is a graph showing the evaluation results of the inhibitory effect of the calcium preparation on the decalcification of dentine.
Figure 16A:
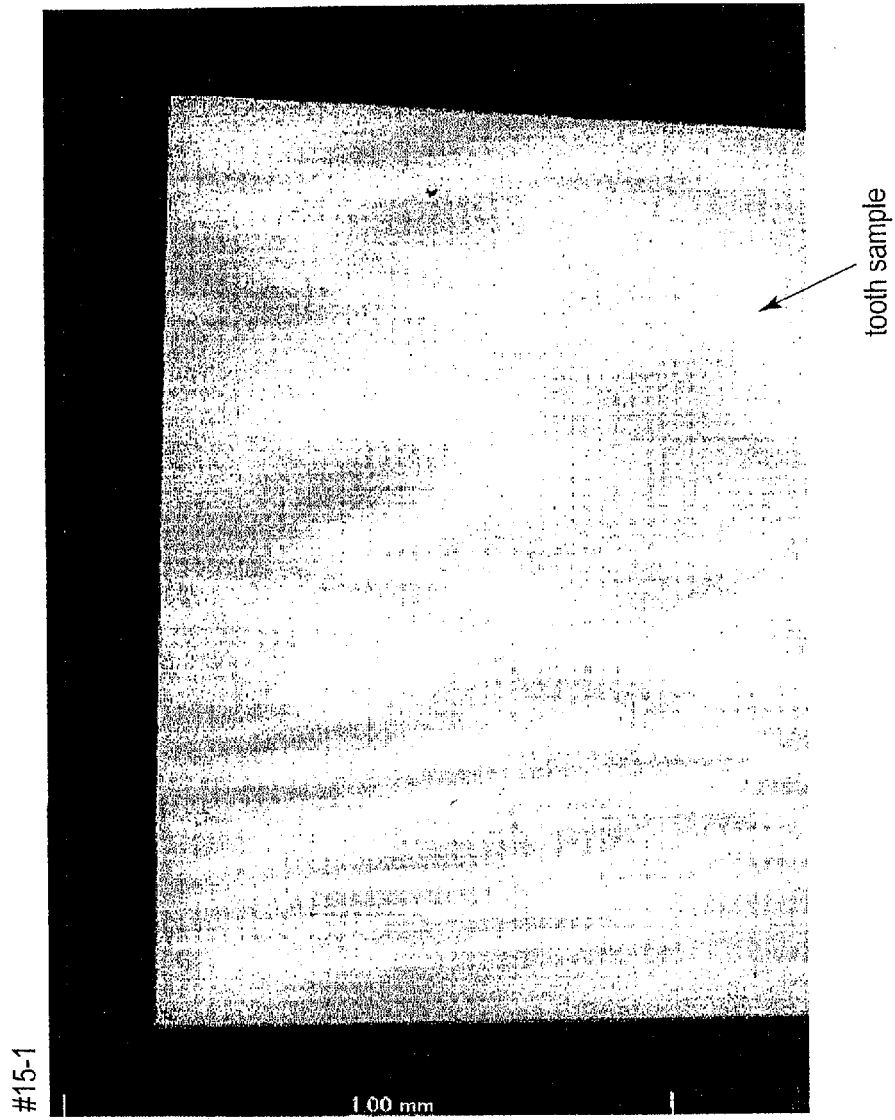
FIG. 16A is a photograph showing the evaluation results of the inhibitory effect of the calcium preparation on the decalcification of dentine.
Figure 16B:
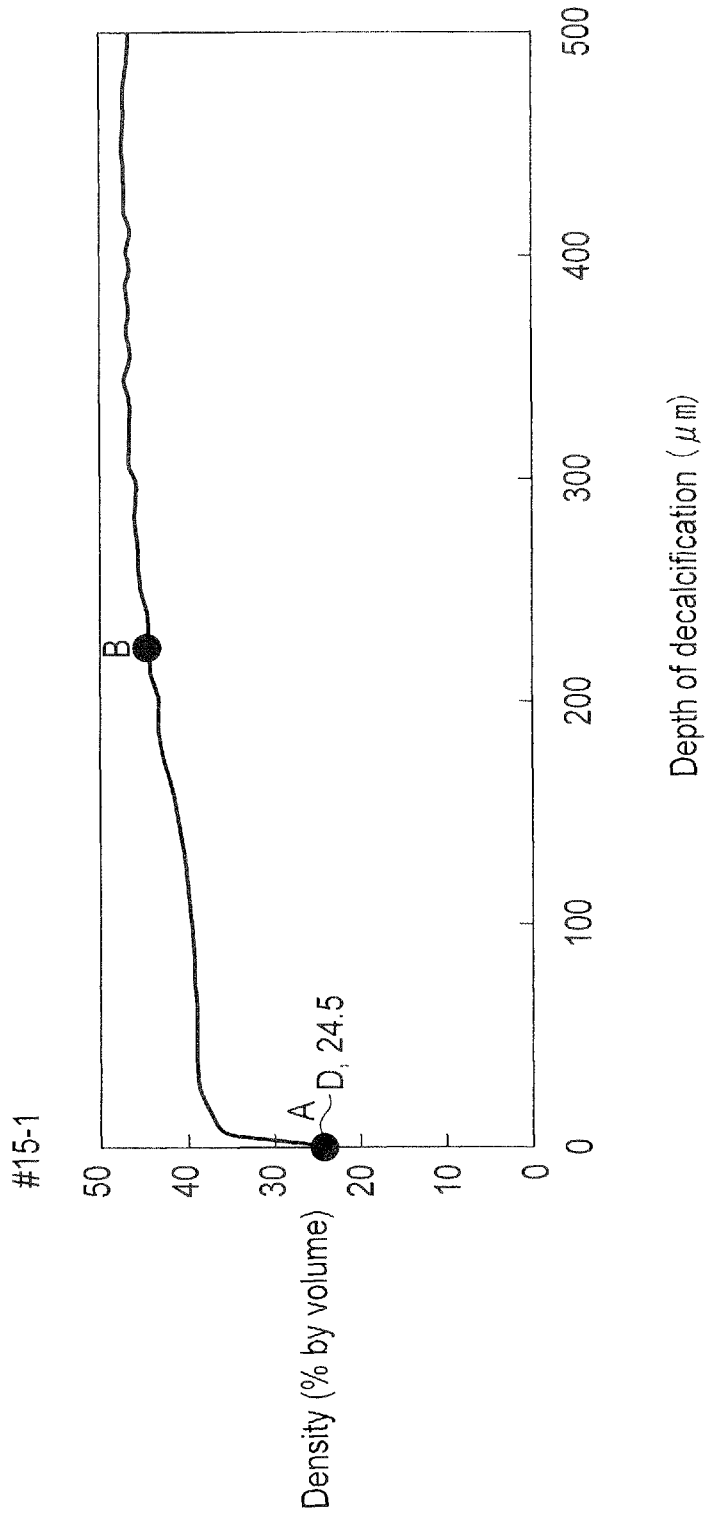
FIG. 16B is a graph showing the evaluation results of the inhibitory effect of the calcium preparation on the decalcification of dentine.

In FIG. 9C, (A) represents distilled water, (B) represents 0.05% of CPCaF (FD), (C) represents 3 mM phosphoric acid, (D) represents a mixture of 3 mM phosphoric acid and 0.05% of CPCaF (FD), (E) represents 1.09 mM citric acid, and (F) represents a mixture of 3 mM phosphoric acid and 1.09 mM citric acid.

In FIG. 99, (A) represents distilled water, (B) represents 0.1% of CPCaF (FD), (C) represents 3 mM phosphoric acid, (D) represents a mixture of 3 mM phosphoric acid and 0.1% of CPCaF (FD), (F) represents 1.09 mM citric acid, and (F) represents a mixture of 3 mM phosphoric acid and 1.09 mM citric acid.

From these results, it was found that the solution of CPCa (FD) and the solution of CPCaF (FD) had a strong buffer capacity to acid as compared to that of the sodium citrate solution having the same concentration and they had characteristics for releasing calcium ions as they became acidic. Therefore, it was suggested that the calcium preparation of the present invention could have an effect of neutralizing an acid to inhibit the decalcification of teeth and an effect of facilitating the recalcification.

(2) Evaluation of Dentinal Decalcification Inhibitory Effect of Calcium Preparation of Present Invention The decalcification inhibitory effect of the calcium preparation of the present invention was examined.

(Method)

A tooth sample (a block of bovine dentine embedded in resin) was immersed in 10 mL of a decalcification liquid ($CaCl_2$: 1.5 mM, $KH_2PO_4$: 0.9 mM, acetic acid: 50 mM, $NaN_3$: 0.02%, pH: 4.5) containing the solid preparations of calcium (CPCa (FD) and CPCaF (FD)) with each concentration (0, 0.02, 0.05, 0.1%) and decalcified at 37° C. for one week.

After decalcification treatment, a section with a thickness of about 240 μm was cut from the tooth sample and the TMR (transversal microradiography which is an X-ray transmission method) image was acquired. Then, the image was subjected to an image analysis.

(Results)

The results are shown in Table 34 below, FIGS. 10A to 16A, and FIGS. 10B to 16B.

TABLE 34

| Group | Additive amount (%) | Ca (mM) | PO4 (mM) | F (ppm) | sample# | Depth of decalcification (μm) | Amount of decalcification (vol % × μm) | Average inhibition ratio (%) |
|---|---|---|---|---|---|---|---|---|
| Control | 0 | 1 | 3 | 0 | #1-2 | 244 | 6303 | — |
|  |  |  |  |  | #2-1 | 308 | 6164 |  |
|  |  |  |  |  | #9-1 | 324 | 6024 |  |
|  |  |  |  |  | #10-2 | 340 | 6602 |  |
| CPCa(FD) | 0.025 | 2.094 | 3.563 | 0 | #3-2 | 241 | 5255 | 13.3 |
|  |  |  |  |  | #4-2 | 272 | 5623 |  |
| CPCa(FD) | 0.050 | 3.187 | 4.126 | 0 | #5-2 | 337 | 5017 | 44.7 |
|  |  |  |  |  | #6-1 | 156 | 1915 |  |
| CPCa(FD) | 0.100 | 5.375 | 5.232 | 0 | #7-2 | 206 | 2400 | 66.6 |
|  |  |  |  |  | #8-1 | 212 | 1793 |  |
| CPCaF(FD) | 0.025 | 2.081 | 3.558 | 1 | #11-2 | 305 | 2415 | 60.3 |
|  |  |  |  |  | #12-1 | 215 | 2561 |  |
| CPCaF(FD) | 0.050 | 3.162 | 4.116 | 2 | #13-2 | 170 | 1543 | 76.4 |
|  |  |  |  |  | #14-1 | 223 | 1413 |  |
| CPCaF(FD) | 0.100 | 5.325 | 5.231 | 4 | #15-1 | 223 | 884 | 87.2 |
|  |  |  |  |  | #16-1 | 126 | 717 |  |

FIGS. 10A to 16A are photographs showing the evaluation results of the dentinal decalcification inhibitory effect of the calcium preparation. FIGS. 10B to 16B are graphs showing the evaluation results of dentinal decalcification inhibitory effect of the calcium preparation. In FIGS. 10B to 16B, "A" represents a decalcified surface and "B" represents a decalcification front.

As is clear from Table 34, a sufficient decalcification inhibitory effect was shown such that the average decalcification inhibition ratio was 44.7% in the case of CPCa (0.05%), and the average decalcification inhibition ratio was 60.3% in the case of CPCaF (0.25%).

(3) Accumulation Test of Artificial Plaque of Calcium Preparation of Present Invention An examination was performed in order to confirm what level of calcium and phosphoric acid in the aqueous preparation of calcium of the present invention was accumulated in the artificial plaque.

(Method)

S. mutans was precultured in TSB [Bact (registered trademark): Tryptic Soy Broth] overnight. Then, 100 μL of the precultured medium of S. mutans was inoculated in TSB to which 2.5 mL of 1% sucrose was added, and cultured in a test tube inclined at about 30° overnight. After culturing overnight the culture medium was removed. The test tube was washed 3 times with 3 mL of physiological saline to obtain an artificial plaque attached to the wall of the test tube. The aqueous preparation of calcium was prepared by dissolving the solid preparation of calcium (CPCa and CPCaF) at a concentration of 0.25% to 10%. Then, 3 mL of the aqueous preparation of calcium was added to the test tube to which the artificial plaque was attached. This sample was reacted at room temperature for 10 minutes. The test tube was washed 3 times with 3 mL of physiological saline. Calcium and phosphoric acid were extracted 3 times with 3 mL of 1N HCl. The weight of the artificial plaque was measured. The calcium extract was measured up to 10 mL. Then, the calcium and phosphorus concentrations were measured by ICP, and concentrations of calcium and phosphorus accumulated in the artificial plaque were calculated.

(Results and Consideration)

The results when the aqueous preparation of calcium (CPCa) was reacted for 10 minutes are shown in Table 35 below.

TABLE 35

|       | CPCa (FD) 10% | CPCa (FD) 5% | CPCa (FD) 1% | CPCa (FD) 0.5% | CPCa (FD) 0.25% | control |
|-------|---------------|--------------|--------------|----------------|-----------------|---------|
| Ca(%) | 0.070         | 0.042        | 0.006        | 0.003          | 0.001           | 0       |
| P(%)  | 0.027         | 0.016        | 0.0026       | 0              | 0               | 0       |
| Ca/P  | 2.59          | 2.63         | 2.31         | —              | —               | —       |

Since the molar ratio of Ca and P in the aqueous preparation of calcium (CPCa) is 2:1, the weight ratio becomes 2.6:1. In the above results, the ratio of Ca and P accumulated in the artificial plaque maintains nearly a theoretical ratio of CPCa.

Here, if it is assumed that the Ca content in CPCa is 17.5% and other components in CPCa are accumulated at the same ratio, when a CPCa10%; solution is reacted, the accumulation concentration is 0.1% in CPCa equivalent. Further, in the case of a CPCa 5% solution, the accumulation concentration is 0.24%. In the case of a CPCa1% solution, the accumulation concentration is 0.034%. In the case of a CPCa0.5% solution, the accumulation concentration is 0.0171%. In the case of a CPCa0.25% solution, the accumulation concentration is 0.0057%.

Both of the decalcification inhibitory effect using dentine and the buffering effect on acid are exerted when the concentration of CPCa is 0.05%. Thus, an effective amount of CPCa is accumulated in the plaque by bringing it into contact with about 1% to 5% of the CPCa solution for about 10 minutes, which may result in the decalcification inhibitory effect.

Subsequently, the results when the aqueous preparation of calcium (CPCaF) was reacted for 10 minutes are shown in Table 36 below.

TABLE 36

|       | CPCaF (FD) 10% | CPCaF (FD) 5% | CPCaF (FD) 1% | CPCaF (FD) 0.5% | CPCaF (FD) 0.25% | control |
|-------|----------------|---------------|---------------|-----------------|------------------|---------|
| Ca(%) | 0.092          | 0.044         | 0.013         | 0.007           | 0.003            | 0       |
| P(%)  | 0.040          | 0.018         | 0.007         | 0               | 0                | 0       |
| Ca/P  | 2.3            | 2.44          | 1.86          | —               | —                | —       |

Since the molar ratio of Ca and P in the aqueous preparation of calcium (CPCaF) is 2:1, the weight ratio becomes 2.6:1. In the above results, the ratio of Ca and P accumulated in the artificial plaque maintains nearly a theoretical ratio of CPCaF.

Here, if it is assumed that the Ca content in CPCaF is 17.5% and all of other components in CPCaF are accumulated at the same ratio, when a CPCaF-10% solution is reacted, the accumulation concentration is 0.52% in CPCaF equivalent. Further, in the case of a CPCaF-5% solution, the accumulation concentration is 0.25%. In the case of a CPCaF-1% solution, the accumulation concentration is 0.074%. In the case of a CPCaF-0.5% solution, the accumulation concentration is 0.034%. In the case of a CPCaF-0.25% solution, the accumulation concentration is 0.017%.

The decalcification inhibitory effect using dentine is exerted when the concentration of CPCaF is 0.025%, and the buffering effect on acid is exerted when the concentration of CPCaF is 0.05%. Thus, an effective amount of CPCaF is accumulated in the plaque by being in contact with about 0.5% to 1% of the aqueous preparation of calcium (CPCaF) for about 10 minutes, which may result in the decalcification inhibitory effect.

Additional advantages and modifications will readily occur to those skilled in the art. The present invention in its broader aspects is therefore not limited to the specific details, representative aspects described herein. Accordingly, various modifications can be made without departing from the spirit or scope of the general inventive concept which is defined by the appended claims and the equivalents thereof.

The calcium preparation according to the present invention is useful in applying calcium to a subject in fields such as medical care, food, agriculture, stock farming, fishery, and horticulture.

What is claimed is:

1. An aqueous preparation of calcium comprising water, calcium, a compound of a Formula I, and a compound of a Formula II as constituent elements,
    wherein 98% or more of the calcium is in a non-ionic calcium form and forms a complex, wherein in the complex, the calcium binds to the compound of the Formula I and/or the compound of the Formula II in a state that basic structures of these compounds are kept, and at least a part of the complex forms colloidal particles having an average particle diameter of 100 nm or less, and
    wherein the aqueous preparation of calcium is a transparent aqueous preparation having a pH value ranging from 4 to 13;

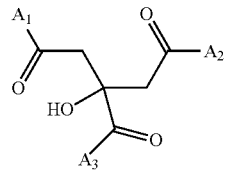

Formula I

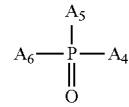

Formula II wherein, A1, A2, A3, A4, A5 and A6 are independently O— or OX, X represents a monovalent or polyvalent cation, and the Xs are the same or different when multiple OXs exist.

2. A solid preparation of calcium obtained by drying the aqueous preparation of calcium according to claim 1.

3. A solid preparation of calcium obtained by drying the aqueous preparation of calcium according to claim 1, wherein adding water again to the solid preparation provides the aqueous preparation of calcium according to claim 1.

4. An aqueous preparation of calcium comprising water, calcium, a compound of a Formula I, a compound of a Formula II, and fluorine as constituent elements, wherein 98% or more of the calcium is in a non-ionic calcium form and forms a complex, wherein in the complex, the calcium binds to the compound of the Formula I and/or the compound of the Formula II in a state that basic structures of these compounds are kept, at least a part of the fluorine binds to the complex, and at least a part of the complex forms colloidal particles having an average particle diameter of 100 nm or less, and wherein the aqueous preparation of calcium is a transparent aqueous preparation having a pH value ranging from 4 to 13;

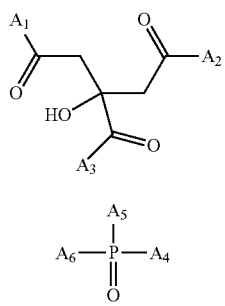

Formula I

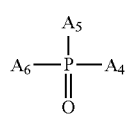

Formula II wherein, A1, A2, A3, A4, A5 and A6 are independently O— or OX, X represents a monovalent or polyvalent cation, and the Xs are the same or different when multiple OXs exist.

5. A solid preparation of calcium obtained by drying the aqueous preparation of calcium according to claim 4.

6. The solid preparation of calcium obtained by drying the aqueous preparation of calcium according to claim 4, wherein adding water again to the solid preparation provides the aqueous preparation of calcium according to claim 4.

7. A method of producing an aqueous preparation of calcium comprising:
(a) mixing a calcium source ionized in water with a source of a compound of a Formula I and a source of a compound of a Formula II to form a non-colloidal liquid; and
(b) aging said non-colloidal liquid from step (a) to convert said non-colloidal liquid to a colloidal liquid thereby converting from an opaque liquid to a transparent liquid under a condition where the pH of a final solution has a value ranging from 4 to 13;

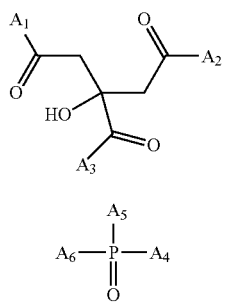

Formula I

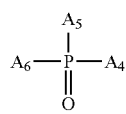

Formula II wherein, A1, A2, A3, A4, A5 and A6 are independently O— or OX, X represents a monovalent or polyvalent cation, and the Xs are the same or different when multiple OXs exist.

8. A method of producing an aqueous preparation of calcium comprising:
(1) ionizing a calcium source in water;
(2) mixing the calcium ionized in step (1) with a source of a compound of a Formula I and a source of a compound of a Formula II to form a non-colloidal liquid;

(3) aging said non-colloidal liquid obtained in step (2) to convert said non-colloidal liquid to a colloidal liquid thereby converting from an opaque liquid to a transparent liquid; and
(4) adjusting the pH so that a solution finally obtained in any of steps (1) to (3) has a pH value ranging from 4 to 13;

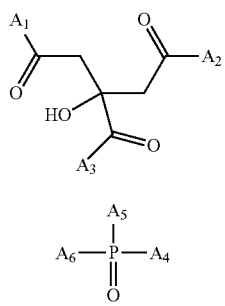

Formula I

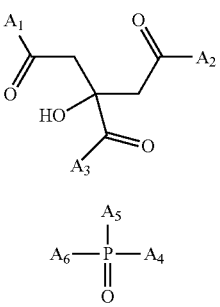

Formula II wherein, A1, A2, A3, A4, A5 and A6 are independently O— or OX, X represents a monovalent or polyvalent cation, and the Xs are the same or different when multiple OXs exist.

9. A method of producing an aqueous preparation of calcium comprising:
(a) mixing a calcium source ionized in water with a source of a compound of a Formula I, a source of a compound of a Formula II, and a fluorine source to form a non-colloidal liquid; and
(b) aging said non-colloidal liquid obtained from step (a) to convert said non-colloidal liquid to a colloidal liquid thereby converting from an opaque liquid to a transparent liquid under a condition where the pH of a final solution has a value ranging from 4 to 13;

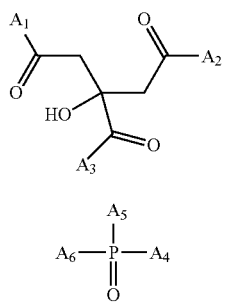

Formula I

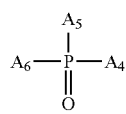

Formula II wherein, A1, A2, A3, A4, A5 and A6 are independently O— or OX, X represents a monovalent or polyvalent cation, and the Xs are the same or different when multiple OXs exist.

10. A method of producing an aqueous preparation of calcium comprising:
(1) ionizing a calcium source in water;
(2) mixing the calcium ionized in step (1) with a source of a compound of a Formula I, a source of a compound of a Formula II, and a fluorine source to form a non-colloidal liquid;
(3) aging said non-colloidal liquid obtained in step (2) to convert said non-colloidal liquid to a colloidal liquid thereby converting from an opaque liquid to a transparent liquid; and (4) adjusting the pH so that a solution finally obtained in any of steps (1) to (3) has a pH value ranging from 4 to 13;

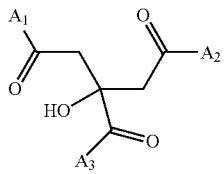

Formula I

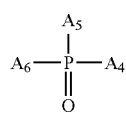

Formula II wherein, A1, A2, A3, A4, A5 and A6 are independently O— or OX, X represents a monovalent or polyvalent cation, and the Xs are the same or different when multiple OXs exist.

11. A method of producing a solid preparation of calcium comprising:
further drying the aqueous preparation of calcium obtained by the method according to any one of claims 7 to 10.

12. An aqueous preparation of calcium comprising water, calcium, a compound of a Formula I, and a compound of a Formula II as constituent elements, which is produced by a method comprising:
(a) mixing a calcium source ionized in water with a source of a compound of the Formula I and a source of a compound of the Formula II to form a non-colloidal liquid; and
(b) aging said non-colloidal liquid from step (a) to convert to a colloidal liquid by converting said non-colloidal liquid from an opaque liquid to a transparent liquid under a condition where the pH has a value ranging from 4 to 13;
wherein 98% or more of the calcium is in a non-ionic calcium form and forms a complex, wherein in the complex, the calcium binds to the compound of the Formula I and/or the compound of the Formula II in a state that basic structures of these compounds are kept, and at least a part of the complex forms colloidal particles having an average particle diameter of 100 nm or less, and
wherein the aqueous preparation of calcium is a transparent aqueous preparation having a pH value ranging from 4 to 13;

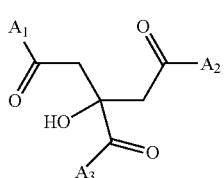

Formula I

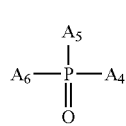

Formula II wherein, A1, A2, A3, A4, A5 and A6 are independently O— or OX, X represents a monovalent or polyvalent cation, and the Xs are the same or different when multiple OXs exist.

13. An aqueous preparation of calcium comprising water, calcium, a compound of a Formula 1, and a compound of a Formula II as constituent elements, which is produced by a method comprising:
(1) ionizing a calcium source in water;
(2) mixing the calcium ionized in step (1) with a source of a compound of the Formula I and a source of a compound of the Formula II to form a non-colloidal liquid;
(3) aging said non-colloidal liquid obtained in step (2) to convert said non-colloidal liquid to a colloidal liquid thereby converting from an opaque liquid to a transparent liquid; and
(4) adjusting the pH so that a solution finally obtained in any of steps (1) to (3) has a pH value ranging from 4 to 13;
wherein 98% or more of the calcium is in a non-ionic calcium form and forms a complex, wherein in the complex, the calcium binds to the compound of the Formula I and/or the compound of the Formula II in a state that basic structures of these compounds are kept, and at least a part of the complex forms colloidal particles having an average particle diameter of 100 nm or less, and wherein the aqueous preparation of calcium is a transparent aqueous preparation having a pH value ranging from 4 to 13;

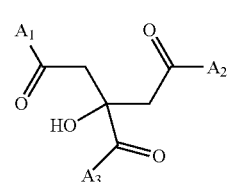

Formula I

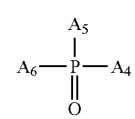

Formula II wherein, A1, A2, A3, A4, A5 and A6 are independently O— or OX, X represents a monovalent or polyvalent cation, and the Xs are the same or different when multiple OXs exist.

14. An aqueous preparation of calcium comprising water, calcium, a compound of a Formula I, a compound of a Formula II, and fluorine constituent elements, which is produced by a method comprising:
(a) mixing a calcium source ionized in water with a source of a compound of the Formula I, a source of a compound of the Formula II, and a fluorine source to form a non-colloidal liquid; and
(b) aging said non-colloidal liquid obtained in step (a) to convert said non-colloidal liquid to a colloidal liquid thereby converting from an opaque liquid to a transparent liquid under a condition where the pH of a final solution has a value ranging from 4 to 13;
wherein 98% or more of the calcium is in a non-ionic calcium form and forms a complex, wherein in the complex, the calcium binds to the compound of the Formula I in a state that basic structures of these compounds are kept, at least a part of the fluorine binds to the complex, and at least a part of the complex forms colloidal particles having an average particle diameter of 100 nm or less, and, wherein the aqueous preparation of calcium is a transparent aqueous preparation of calcium having a pH value ranging from 4 to 13;

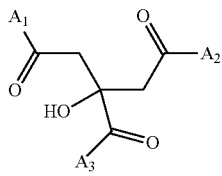

Formula I

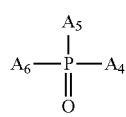

Formula II wherein, A1, A2, A3, A4, A5 and A6 are independently O— or OX, X represents a monovalent or polyvalent cation, and the Xs are the same or different when multiple OXs exist.

15. An aqueous preparation of calcium comprising water, calcium, a compound of a Formula I, a compound of a Formula II, and fluorine as constituent elements, which is produced by a method comprising:
(1) ionizing a calcium source in water;
(2) mixing the calcium ionized in step (1) with a source of a compound of the Formula I, a source of a compound of the Formula II, and a fluorine source to form a a non-colloidal liquid;
(3) aging said non-colloidal liquid obtained in step (2) to convert said non-colloidal liquid to a colloidal liquid thereby converting from an opaque liquid to a transparent liquid; and
(4) adjusting the pH so that a solution finally obtained in any of steps (1) to (3) has a pH value ranging from 4 to 13;
wherein 98% or more of the calcium is in a non-ionic calcium form and forms a complex, wherein in the complex, the calcium binds to the compound of the Formula I and/or the compound of the Formula II in a state that basic structures of these compounds are kept, at least a part of the fluorine binds to the complex, and at least a part of the complex forms colloidal particles having an average particle diameter of 100 nm or less, and
wherein the aqueous preparation of calcium is a transparent aqueous preparation having a pH value ranging from 4 to 13;

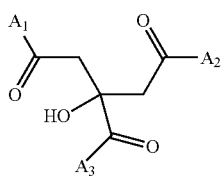

Formula I

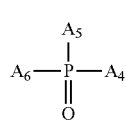

Formula II wherein, A1, A2, A3, A4, A5 and A6 are independently O— or OX, X represents a monovalent or polyvalent cation, and the Xs are the same or different when multiple OXs exist.

16. The aqueous preparation of calcium according to claim 12 or 14, wherein the aqueous preparation of calcium of claim maintains and contains all the constituents present in the reaction.

17. The aqueous preparation of calcium according to claim 13 or 15, wherein the aqueous preparation of calcium maintains and contains all the constituents present in steps (1) and (2).

18. A solid preparation of calcium produced by the method according to claim 11.

19. A solid preparation of calcium produced by drying the aqueous preparation of calcium obtained by the method according to claims 7 or 8, wherein adding water to the solid preparation leads to an aqueous preparation of calcium comprising water, calcium, a compound of a Formula I, and a compound of a Formula II as constituent elements,
wherein 98% or more of the calcium is in a non-ionic calcium form and forms a complex, wherein in the complex, the calcium binds to the compound of the Formula I and/or the compound of the Formula II in a state that basic structures of these compounds are kept, and at least a part of the complex forms colloidal particles having an average particle diameter of 100 nm or less, and
wherein the aqueous preparation of calcium is a transparent aqueous preparation having a pH value ranging from 4 to 13;

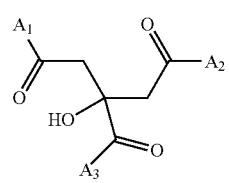

Formula I

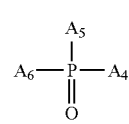

Formula II wherein, A1, A2, A3, A4, A5 and A6 are independently O— or OX, X represents a monovalent or polyvalent cation, and the Xs are the same or different when multiple OXs exist.

20. A method of preventing the formation of precipitates derived from calcium in a calcium solution comprising:
(a) mixing calcium ionized in water with a compound of a Formula I and a compound of a Formula II to form a non-colloidal liquid; and
(b) aging to convert said non-colloidal liquid to a colloidal liquid thereby converting from an opaque liquid to a transparent liquid under a condition where the pH of a final solution has a value ranging from 4 to 13;

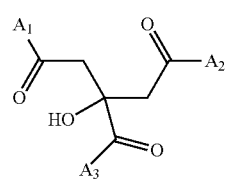

Formula I

-continued

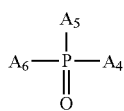

Formula II wherein, A1, A2, A3, A4, A5 and A6 are independently O— or OX, X represents a monovalent or polyvalent cation, and the Xs are the same or different when multiple OXs exist.

21. A method of preventing the formation of precipitates derived from calcium in a calcium solution comprising:

(1) ionizing calcium in water;

(2) mixing the calcium ionized in (1) with a Compound of a Formula I and a compound of a Formula II to form a non-colloidal liquid;

(3) aging said non-colloidal liquid obtained in step (2) to convert said non-colloidal liquid to a colloidal liquid thereby converting from an opaque liquid to a transparent liquid; and (4) adjusting the pH so that a solution finally obtained in any of steps (1) to (3) has a pH value ranging from 4 to 13;

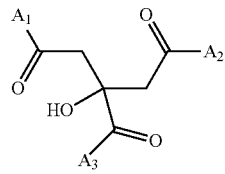

Formula I

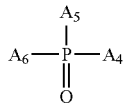

Formula II wherein, A1, A2, A3, A4, A5 and A6 are independently O— or OX, X represents a monovalent or polyvalent cation, and the Xs are the same or different when multiple OXs exist.

22. A solid preparation of calcium produced by drying the aqueous preparation of calcium obtained by the method according to claims 9 or 10, wherein adding water to the solid preparation leads to an aqueous preparation of calcium comprising water, calcium, a compound of a Formula I, a compound of a Formula II, and fluorine as constituent elements, wherein 98% or more of the calcium is in a non-ionic calcium form and forms a complex, wherein in the complex, the calcium binds to the compound of the Formula I and/or the compound of the Formula II in a state that basic structures of these compounds are kept, at least a part of the fluorine binds to the complex, and at least a part of the complex forms colloidal particles having an average particle diameter of 100 nm or less, and wherein the aqueous preparation of calcium is a transparent aqueous preparation having a pH value ranging from 4 to 13;

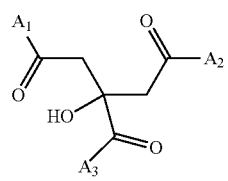

Formula I

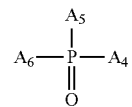

Formula II wherein, A1, A2, A3, A4, A5 and A6 are independently O— or OX, X represents a monovalent or polyvalent cation, and the Xs are the same or different when multiple OXs exist.

* * * * *